United States Patent
Pintor et al.

(10) Patent No.: US 11,471,279 B2
(45) Date of Patent: Oct. 18, 2022

(54) SYSTEMS FOR RAPIDLY DEPLOYABLE SURGICAL HEART VALVES

(71) Applicant: Edwards Lifesciences Corporation, Irvine, CA (US)

(72) Inventors: Rafael Pintor, Mission Viejo, CA (US); Michael J. Scott, San Diego, CA (US); Thomas Chien, Irvine, CA (US); Harvey H. Chen, Irvine, CA (US); August R. Yambao, Temecula, CA (US); Lawrence J. Farhat, Carlsbad, CA (US); Andrew Phung, Brea, CA (US); William C. Brunnett, Mission Viejo, CA (US); Carey L. Cristea, Lake Forest, CA (US); Sara M. Walls, Draper, UT (US); Kevin W. Zheng, Tustin, CA (US); Faisal Kalam, Corona, CA (US); Qinggang Zeng, Mission Viejo, CA (US)

(73) Assignee: Edwards Lifesciences Corporation, Irvine, CA (US)

( * ) Notice: Subject to any disclaimer, the term of this patent is extended or adjusted under 35 U.S.C. 154(b) by 175 days.

(21) Appl. No.: 16/938,142

(22) Filed: Jul. 24, 2020

(65) Prior Publication Data
US 2020/0352713 A1    Nov. 12, 2020

Related U.S. Application Data

(60) Continuation of application No. 16/056,252, filed on Aug. 6, 2018, now Pat. No. 10,722,358, which is a
(Continued)

(51) Int. Cl.
*A61F 2/24*    (2006.01)

(52) U.S. Cl.
CPC .......... *A61F 2/2433* (2013.01); *A61F 2/2409* (2013.01); *A61F 2/2412* (2013.01);
(Continued)

(58) Field of Classification Search
CPC .... A61F 2/2433; A61F 2/2409; A61F 2/2412; A61F 2/2418; A61F 2220/0008;
(Continued)

(56) References Cited

U.S. PATENT DOCUMENTS

| 3,143,742 A | 8/1964 | Cromie |
| 3,320,972 A | 5/1967 | High et al. |

(Continued)

FOREIGN PATENT DOCUMENTS

| EP | 0084395 A1 | 7/1983 |
| EP | 0125393 A1 | 11/1984 |

(Continued)

OTHER PUBLICATIONS

Krakow, "3F Therapeutics, Inc. Announces the First Clinical Implantation of the 3F Enable Aortic Heart Valve, a Patented, Sutureless Implantation, Replacement Heart Valve Intended to Save Valuable Surgery Time and Reduce Time Related Complications . . ." Healthcare Sales & Marketing Network News Feed, Jan. 18, 2005, pp. 1-2.

(Continued)

*Primary Examiner* — Paul B Prebilic
(74) *Attorney, Agent, or Firm* — Guy Cumberbatch

(57) ABSTRACT

A quick-connect heart valve prosthesis that can be quickly and easily implanted during a surgical procedure is provided. The heart valve includes a substantially non-expandable, non-compressible prosthetic valve and a plastically-expandable frame, thereby enabling attachment to the annulus without sutures. A small number of guide sutures may be provided for aortic valve orientation. The prosthetic (Continued)

valve may be a commercially available valve with a sewing ring with the frame attached thereto. The frame may expand from a conical deployment shape to a conical expanded shape, and may include web-like struts connected between axially-extending posts. A system and method for deployment includes an integrated handle shaft and balloon catheter. A valve holder is stored with the heart valve and the handle shaft easily attaches thereto to improve valve preparation steps.

20 Claims, 32 Drawing Sheets

Related U.S. Application Data continuation of application No. 15/360,483, filed on Nov. 23, 2016, now Pat. No. 10,039,641, which is a continuation of application No. 14/164,764, filed on Jan. 27, 2014, now Pat. No. 9,504,563, which is a division of application No. 13/167,639, filed on Jun. 23, 2011, now Pat. No. 8,641,757.

(60) Provisional application No. 61/381,931, filed on Sep. 10, 2010.

(52) U.S. Cl.
CPC ...... *A61F 2/2418* (2013.01); *A61F 2220/005* (2013.01); *A61F 2220/0008* (2013.01); *A61F 2220/0016* (2013.01); *A61F 2220/0025* (2013.01); *A61F 2220/0075* (2013.01); *A61F 2220/0083* (2013.01); *A61F 2230/0067* (2013.01); *A61F 2250/006* (2013.01); *A61F 2250/0018* (2013.01); *A61F 2250/0039* (2013.01); *A61F 2250/0048* (2013.01)

(58) Field of Classification Search
CPC ...... A61F 2220/0016; A61F 2220/0025; A61F 2220/0075; A61F 2220/0058; A61F 2250/0039; A61F 2250/001; A61F 2250/0073
See application file for complete search history.

(56) References Cited

U.S. PATENT DOCUMENTS

| | | | |
|---|---|---|---|
| 3,371,352 A | 3/1968 | Siposs et al. |
| 3,409,013 A | 11/1968 | Berry |
| 3,546,710 A | 12/1970 | Shumakov et al. |
| 3,574,865 A | 4/1971 | Hamaker |
| 3,628,535 A | 12/1971 | Ostrowsky et al. |
| 3,657,744 A | 4/1972 | Ersek |
| 3,686,740 A | 8/1972 | Shiley |
| 3,755,823 A | 9/1973 | Hancock |
| 3,839,741 A | 10/1974 | Haller |
| 4,035,849 A | 7/1977 | Angell et al. |
| 4,078,468 A | 3/1978 | Civitello |
| 4,079,468 A | 3/1978 | Liotta et al. |
| 4,084,268 A | 4/1978 | Ionescu et al. |
| 4,106,129 A | 8/1978 | Carpentier et al. |
| 4,172,295 A | 10/1979 | Batten |
| 4,211,325 A | 7/1980 | Wright |
| 4,217,665 A | 8/1980 | Bex et al. |
| 4,218,782 A | 8/1980 | Rygg |
| 4,259,753 A | 4/1981 | Liotta et al. |
| RE30,912 E | 4/1982 | Hancock |
| 4,340,091 A | 7/1982 | Skelton et al. |
| 4,343,048 A | 8/1982 | Ross et al. |
| 4,364,126 A | 12/1982 | Rosen et al. |
| 4,388,735 A | 6/1983 | Ionescu et al. |
| 4,441,216 A | 4/1984 | Ionescu et al. |
| 4,451,936 A | 6/1984 | Carpentier et al. |
| 4,470,157 A | 9/1984 | Love |
| 4,490,859 A | 1/1985 | Black et al. |
| 4,496,348 A | 1/1985 | Genese et al. |
| 4,501,030 A | 2/1985 | Lane |
| 4,506,394 A | 3/1985 | Bedard |
| 4,535,483 A | 8/1985 | Klawitter et al. |
| 4,605,407 A | 8/1986 | Black et al. |
| 4,626,255 A | 12/1986 | Reichart et al. |
| 4,629,459 A | 12/1986 | Ionescu et al. |
| 4,680,031 A | 7/1987 | Alonso |
| 4,687,483 A | 8/1987 | Fisher et al. |
| 4,702,250 A | 10/1987 | Ovil et al. |
| 4,705,516 A | 11/1987 | Barone et al. |
| 4,725,274 A | 2/1988 | Lane et al. |
| 4,731,074 A | 3/1988 | Rousseau et al. |
| 4,778,461 A | 10/1988 | Pietsch et al. |
| 4,790,843 A | 12/1988 | Carpentier et al. |
| 4,851,000 A | 7/1989 | Gupta |
| 4,865,600 A | 9/1989 | Carpentier et al. |
| 4,888,009 A | 12/1989 | Lederman et al. |
| 4,914,097 A | 4/1990 | Oda et al. |
| 4,960,424 A | 10/1990 | Grooters |
| 4,993,428 A | 2/1991 | Arms |
| 5,010,892 A | 4/1991 | Colvin et al. |
| 5,032,128 A | 7/1991 | Alonso |
| 5,037,434 A | 8/1991 | Lane |
| 5,147,391 A | 9/1992 | Lane |
| 5,163,953 A | 11/1992 | Vince |
| 5,163,955 A | 11/1992 | Love et al. |
| 5,258,023 A | 11/1993 | Reger |
| 5,290,300 A | 3/1994 | Cosgrove et al. |
| 5,316,016 A | 5/1994 | Adams et al. |
| 5,326,370 A | 7/1994 | Love et al. |
| 5,326,371 A | 7/1994 | Love et al. |
| 5,332,402 A | 7/1994 | Teitelbaum |
| 5,360,444 A | 11/1994 | Kusuhara |
| 5,370,685 A | 12/1994 | Stevens |
| 5,376,112 A | 12/1994 | Duran |
| 5,396,887 A | 3/1995 | Imran |
| 5,397,351 A | 3/1995 | Pavcnik et al. |
| 5,411,522 A | 5/1995 | Trott |
| 5,411,552 A | 5/1995 | Andersen et al. |
| 5,423,887 A | 6/1995 | Love et al. |
| 5,425,741 A | 6/1995 | Lemp et al. |
| 5,431,676 A | 7/1995 | Dubrul et al. |
| 5,449,384 A | 9/1995 | Johnson |
| 5,449,385 A | 9/1995 | Religa et al. |
| 5,469,868 A | 11/1995 | Reger |
| 5,476,510 A | 12/1995 | Eberhardt et al. |
| 5,488,789 A | 2/1996 | Religa et al. |
| 5,489,297 A | 2/1996 | Duran |
| 5,489,298 A | 2/1996 | Love et al. |
| 5,500,016 A | 3/1996 | Fisher |
| 5,522,884 A | 6/1996 | Wright |
| 5,531,785 A | 7/1996 | Love et al. |
| 5,533,515 A | 7/1996 | Coller et al. |
| 5,549,665 A | 8/1996 | Vesely et al. |
| 5,562,729 A | 10/1996 | Purdy et al. |
| 5,571,215 A | 11/1996 | Sterman et al. |
| 5,573,007 A | 11/1996 | Bobo, Sr. |
| 5,578,076 A | 11/1996 | Krueger et al. |
| 5,584,803 A | 12/1996 | Stevens et al. |
| 5,618,307 A | 4/1997 | Donlon et al. |
| 5,626,607 A | 5/1997 | Malecki et al. |
| 5,628,789 A | 5/1997 | Vanney et al. |
| 5,693,090 A | 12/1997 | Unsworth et al. |
| 5,695,503 A | 12/1997 | Krueger et al. |
| 5,713,952 A | 2/1998 | Vanney et al. |
| 5,716,370 A | 2/1998 | Williamson, IV et al. |
| 5,728,064 A | 3/1998 | Burns et al. |
| 5,728,151 A | 3/1998 | Garrison et al. |
| 5,735,894 A | 4/1998 | Krueger et al. |
| 5,752,522 A | 5/1998 | Murphy |
| 5,755,782 A | 5/1998 | Love et al. |
| 5,766,240 A | 6/1998 | Johnson |
| 5,776,187 A | 7/1998 | Krueger et al. |
| 5,776,188 A | 7/1998 | Shepherd et al. |
| 5,800,527 A | 9/1998 | Jansen et al. |

(56) References Cited

U.S. PATENT DOCUMENTS

| | | |
|---|---|---|
| 5,814,097 A | 9/1998 | Sterman et al. |
| 5,814,098 A | 9/1998 | Hinnenkamp et al. |
| 5,824,064 A | 10/1998 | Taheri |
| 5,824,068 A | 10/1998 | Bugge |
| 5,840,081 A | 11/1998 | Andersen et al. |
| 5,848,969 A | 12/1998 | Panescu et al. |
| 5,855,563 A | 1/1999 | Kaplan et al. |
| 5,855,601 A | 1/1999 | Bessler et al. |
| 5,865,801 A | 2/1999 | Houser |
| 5,891,160 A | 4/1999 | Williamson, IV et al. |
| 5,895,420 A | 4/1999 | Mirsch, II et al. |
| 5,902,308 A | 5/1999 | Murphy |
| 5,908,450 A | 6/1999 | Gross et al. |
| 5,919,147 A | 7/1999 | Jain |
| 5,921,934 A | 7/1999 | Teo |
| 5,921,935 A | 7/1999 | Hickey |
| 5,924,984 A | 7/1999 | Rao |
| 5,928,281 A | 7/1999 | Huynh et al. |
| 5,957,949 A | 9/1999 | Leonhardt et al. |
| 5,972,004 A | 10/1999 | Williamson, IV et al. |
| 5,984,959 A | 11/1999 | Robertson et al. |
| 5,984,973 A | 11/1999 | Girard et al. |
| 6,010,531 A | 1/2000 | Donlon et al. |
| 6,042,607 A | 3/2000 | Williamson, IV et al. |
| 6,059,827 A | 5/2000 | Fenton, Jr. |
| 6,066,160 A | 5/2000 | Colvin et al. |
| 6,074,418 A | 6/2000 | Buchanan et al. |
| 6,081,737 A | 6/2000 | Shah |
| 6,083,179 A | 7/2000 | Oredsson |
| 6,099,475 A | 8/2000 | Seward et al. |
| 6,106,550 A | 8/2000 | Magovern et al. |
| 6,110,200 A | 8/2000 | Hinnenkamp |
| 6,117,091 A | 9/2000 | Young et al. |
| 6,126,007 A | 10/2000 | Kari et al. |
| 6,162,233 A | 12/2000 | Williamson, IV et al. |
| 6,168,614 B1 | 1/2001 | Andersen et al. |
| 6,176,877 B1 | 1/2001 | Buchanan et al. |
| 6,197,054 B1 | 3/2001 | Hamblin, Jr. et al. |
| 6,200,306 B1 | 3/2001 | Klostermeyer et al. |
| 6,217,611 B1 | 4/2001 | Klostermeyer |
| 6,231,561 B1 | 5/2001 | Frazier et al. |
| 6,241,765 B1 | 6/2001 | Griffin et al. |
| 6,245,102 B1 | 6/2001 | Jayaraman |
| 6,264,611 B1 | 7/2001 | Ishikawa et al. |
| 6,264,691 B1 | 7/2001 | Gabbay |
| 6,283,127 B1 | 9/2001 | Sterman et al. |
| 6,287,339 B1 | 9/2001 | Vazquez et al. |
| 6,312,447 B1 | 11/2001 | Grimes |
| 6,312,465 B1 | 11/2001 | Griffin et al. |
| 6,322,526 B1 | 11/2001 | Rosenman et al. |
| 6,328,727 B1 | 12/2001 | Frazier et al. |
| 6,350,282 B1 | 2/2002 | Eberhardt |
| 6,358,240 B1 | 3/2002 | Campbell et al. |
| 6,371,983 B1 | 4/2002 | Lane |
| 6,402,780 B2 | 6/2002 | Williamson, IV et al. |
| 6,425,916 B1 | 7/2002 | Garrison et al. |
| 6,454,799 B1 | 9/2002 | Schreck |
| 6,458,100 B2 | 10/2002 | Roue et al. |
| 6,458,153 B1 | 10/2002 | Bailey et al. |
| 6,468,305 B1 | 10/2002 | Otte |
| 6,491,624 B1 | 12/2002 | Lotfi |
| 6,530,952 B2 | 3/2003 | Vesely |
| 6,558,429 B2 | 5/2003 | Taylor |
| 6,569,196 B1 | 5/2003 | Vesely |
| 6,582,462 B1 | 6/2003 | Andersen et al. |
| 6,585,766 B1 | 7/2003 | Huynh et al. |
| 6,682,559 B2 | 1/2004 | Myers et al. |
| 6,685,739 B2 | 2/2004 | DiMatteo et al. |
| 6,702,825 B2 | 3/2004 | Frazier et al. |
| 6,712,804 B2 | 3/2004 | Roue et al. |
| 6,719,789 B2 | 4/2004 | Cox |
| 6,730,118 B2 | 5/2004 | Spenser et al. |
| 6,733,525 B2 | 5/2004 | Yang et al. |
| 6,746,472 B2 | 6/2004 | Frazier et al. |
| 6,764,508 B1 | 7/2004 | Roehe et al. |
| 6,767,362 B2 | 7/2004 | Schreck |
| 6,773,457 B2 | 8/2004 | Ivancev et al. |
| 6,786,925 B1 | 9/2004 | Schoon et al. |
| 6,790,229 B1 | 9/2004 | Berreklouw |
| 6,790,230 B2 | 9/2004 | Beyersdorf et al. |
| 6,805,711 B2 | 10/2004 | Quijano et al. |
| 6,846,325 B2 | 1/2005 | Liddicoat |
| 6,893,459 B1 | 5/2005 | Macoviak |
| 6,893,460 B2 | 5/2005 | Spenser et al. |
| 6,936,067 B2 | 8/2005 | Buchanan |
| 6,939,365 B1 | 9/2005 | Fogarty et al. |
| 6,964,682 B2 | 11/2005 | Nguyen-Thien-Nhon et al. |
| 6,974,476 B2 | 12/2005 | McGuckin, Jr. et al. |
| 6,978,176 B2 | 12/2005 | Lattouf |
| 7,011,681 B2 | 3/2006 | Vesely |
| 7,018,404 B2 | 3/2006 | Holmberg et al. |
| 7,025,780 B2 | 4/2006 | Gabbay |
| 7,037,333 B2 | 5/2006 | Myers et al. |
| 7,070,616 B2 | 7/2006 | Majercak et al. |
| 7,081,131 B2 | 7/2006 | Thornton |
| 7,097,659 B2 | 8/2006 | Woolfson et al. |
| 7,101,396 B2 | 9/2006 | Artof et al. |
| 7,147,663 B1 | 12/2006 | Berg et al. |
| 7,153,324 B2 | 12/2006 | Case et al. |
| 7,160,320 B2 | 1/2007 | Duran |
| 7,172,625 B2 | 2/2007 | Shu et al. |
| 7,186,265 B2 | 3/2007 | Sharkawy et al. |
| 7,195,641 B2 | 3/2007 | Palmaz et al. |
| 7,201,771 B2 | 4/2007 | Lane |
| 7,201,772 B2 | 4/2007 | Schwammenthal et al. |
| 7,238,200 B2 | 7/2007 | Lee et al. |
| 7,252,682 B2 | 8/2007 | Seguin |
| 7,261,732 B2 | 8/2007 | Justino |
| 7,300,463 B2 | 11/2007 | Liddicoat |
| 7,311,730 B2 | 12/2007 | Gabbay |
| RE40,377 E | 6/2008 | Williamson, IV et al. |
| 7,393,360 B2 | 7/2008 | Spenser et al. |
| 7,422,603 B2 | 9/2008 | Lane |
| 7,429,269 B2 | 9/2008 | Schwammenthal et al. |
| 7,442,204 B2 | 10/2008 | Schwammenthal et al. |
| 7,445,630 B2 | 11/2008 | Lashinski et al. |
| 7,445,631 B2 | 11/2008 | Salahieh et al. |
| 7,468,073 B2 | 12/2008 | Johnson et al. |
| 7,470,285 B2 | 12/2008 | Nugent et al. |
| 7,510,575 B2 | 3/2009 | Spenser et al. |
| 7,513,909 B2 | 4/2009 | Lane et al. |
| 7,524,330 B2 | 4/2009 | Berreklouw |
| 7,534,261 B2 | 5/2009 | Friedman |
| 7,556,647 B2 | 7/2009 | Drews et al. |
| 7,569,072 B2 | 8/2009 | Berg et al. |
| 7,578,843 B2 | 8/2009 | Shu |
| 7,585,321 B2 | 9/2009 | Cribier |
| 7,591,848 B2 | 9/2009 | Allen |
| 7,597,711 B2 | 10/2009 | Drews et al. |
| 7,611,535 B2 | 11/2009 | Woolfson et al. |
| 7,618,446 B2 | 11/2009 | Andersen et al. |
| 7,618,447 B2 | 11/2009 | Case et al. |
| 7,622,276 B2 | 11/2009 | Cunanan et al. |
| 7,625,403 B2 | 12/2009 | Krivoruchko |
| 7,641,687 B2 | 1/2010 | Chinn et al. |
| 7,658,763 B2 | 2/2010 | Stable |
| 7,682,390 B2 | 3/2010 | Seguin |
| 7,704,277 B2 | 4/2010 | Zakay et al. |
| 7,708,775 B2 | 5/2010 | Rowe et al. |
| 7,727,276 B2 | 6/2010 | Machiraju |
| 7,740,655 B2 | 6/2010 | Birdsall |
| 7,799,069 B2 | 9/2010 | Bailey et al. |
| 7,822,414 B2 | 10/2010 | Bender et al. |
| 7,862,610 B2 | 1/2011 | Quintessenza |
| 7,887,583 B2 | 2/2011 | Macoviak |
| 7,896,913 B2 | 3/2011 | Damm et al. |
| 7,947,072 B2 | 5/2011 | Yang et al. |
| 7,951,197 B2 | 5/2011 | Lane et al. |
| 7,967,857 B2 | 6/2011 | Lane |
| 7,972,377 B2 | 7/2011 | Lane |
| 7,989,157 B2 | 8/2011 | Cunanan et al. |
| 7,998,151 B2 | 8/2011 | St. Goar et al. |
| 8,062,355 B2 | 11/2011 | Figulla et al. |
| 8,167,932 B2 | 5/2012 | Bourang |

(56) References Cited

U.S. PATENT DOCUMENTS

| | | |
|---|---|---|
| 8,246,675 B2 | 8/2012 | Zegdi |
| 8,246,678 B2 | 8/2012 | Salahieh et al. |
| 8,308,798 B2 | 11/2012 | Pintor et al. |
| 8,323,337 B2 | 12/2012 | Gurskis et al. |
| 8,348,998 B2 | 1/2013 | Pintor et al. |
| 8,353,953 B2 | 1/2013 | Giannetti et al. |
| 8,500,798 B2 | 8/2013 | Rowe et al. |
| 8,821,569 B2 | 9/2014 | Gurskis et al. |
| 2001/0007956 A1 | 7/2001 | Letac et al. |
| 2001/0021872 A1 | 9/2001 | Bailey et al. |
| 2001/0041914 A1 | 11/2001 | Frazier et al. |
| 2002/0026238 A1 | 2/2002 | Lane et al. |
| 2002/0032481 A1 | 3/2002 | Gabbay |
| 2002/0058995 A1 | 5/2002 | Stevens |
| 2002/0077698 A1 | 6/2002 | Peredo |
| 2002/0123802 A1 | 9/2002 | Snyders |
| 2002/0138138 A1 | 9/2002 | Yang |
| 2002/0151970 A1 | 10/2002 | Garrison et al. |
| 2002/0188348 A1 | 12/2002 | DiMatteo et al. |
| 2002/0198594 A1 | 12/2002 | Schreck |
| 2003/0014104 A1 | 1/2003 | Cribier |
| 2003/0023300 A1 | 1/2003 | Bailey et al. |
| 2003/0023303 A1 | 1/2003 | Palmaz et al. |
| 2003/0040792 A1 | 2/2003 | Gabbay |
| 2003/0055495 A1 | 3/2003 | Pease et al. |
| 2003/0105519 A1 | 6/2003 | Fasol et al. |
| 2003/0109924 A1 | 6/2003 | Cribier |
| 2003/0114913 A1 | 6/2003 | Spenser et al. |
| 2003/0130729 A1 | 7/2003 | Paniagua et al. |
| 2003/0149478 A1 | 8/2003 | Figulla et al. |
| 2003/0167089 A1 | 9/2003 | Lane |
| 2003/0236568 A1 | 12/2003 | Hojeibane et al. |
| 2004/0019374 A1 | 1/2004 | Hojeibane et al. |
| 2004/0034411 A1 | 2/2004 | Quijano et al. |
| 2004/0106976 A1 | 6/2004 | Bailey et al. |
| 2004/0122514 A1 | 6/2004 | Fogarty et al. |
| 2004/0122516 A1 | 6/2004 | Fogarty et al. |
| 2004/0167573 A1 | 8/2004 | Williamson et al. |
| 2004/0186563 A1 | 9/2004 | Iobbi |
| 2004/0186565 A1 | 9/2004 | Schreck |
| 2004/0206363 A1 | 10/2004 | McCarthy et al. |
| 2004/0210304 A1 | 10/2004 | Seguin et al. |
| 2004/0210305 A1 | 10/2004 | Shu et al. |
| 2004/0210307 A1 | 10/2004 | Khairkhahan |
| 2004/0225355 A1 | 11/2004 | Stevens |
| 2004/0236411 A1 | 11/2004 | Sarac et al. |
| 2004/0260390 A1 | 12/2004 | Sarac et al. |
| 2005/0010285 A1 | 1/2005 | Lambrecht et al. |
| 2005/0027348 A1 | 2/2005 | Case et al. |
| 2005/0033398 A1 | 2/2005 | Seguin |
| 2005/0043760 A1 | 2/2005 | Fogarty et al. |
| 2005/0043790 A1 | 2/2005 | Seguin |
| 2005/0060029 A1 | 3/2005 | Le et al. |
| 2005/0065594 A1 | 3/2005 | DiMatteo et al. |
| 2005/0065614 A1 | 3/2005 | Stinson |
| 2005/0075584 A1 | 4/2005 | Cali |
| 2005/0075713 A1 | 4/2005 | Biancucci et al. |
| 2005/0075717 A1 | 4/2005 | Nguyen et al. |
| 2005/0075718 A1 | 4/2005 | Nguyen et al. |
| 2005/0075719 A1 | 4/2005 | Bergheim |
| 2005/0075720 A1 | 4/2005 | Nguyen et al. |
| 2005/0075724 A1 | 4/2005 | Svanidze et al. |
| 2005/0080454 A1 | 4/2005 | Drews et al. |
| 2005/0096738 A1 | 5/2005 | Cali et al. |
| 2005/0137682 A1 | 6/2005 | Justino |
| 2005/0137686 A1 | 6/2005 | Salahieh et al. |
| 2005/0137687 A1 | 6/2005 | Salahieh et al. |
| 2005/0137688 A1 | 6/2005 | Salahieh et al. |
| 2005/0137689 A1 | 6/2005 | Salahieh et al. |
| 2005/0137690 A1 | 6/2005 | Salahieh et al. |
| 2005/0137691 A1 | 6/2005 | Salahieh et al. |
| 2005/0137692 A1 | 6/2005 | Haug et al. |
| 2005/0137694 A1 | 6/2005 | Haug et al. |
| 2005/0137695 A1 | 6/2005 | Salahieh et al. |
| 2005/0165477 A1 | 7/2005 | Anduiza et al. |
| 2005/0165479 A1 | 7/2005 | Drews et al. |
| 2005/0182483 A1 | 8/2005 | Osborne et al. |
| 2005/0182486 A1 | 8/2005 | Gabbay |
| 2005/0192665 A1 | 9/2005 | Spenser et al. |
| 2005/0203616 A1 | 9/2005 | Cribier |
| 2005/0203617 A1 | 9/2005 | Forster et al. |
| 2005/0222674 A1 | 10/2005 | Paine |
| 2005/0234546 A1 | 10/2005 | Nugent et al. |
| 2005/0240259 A1 | 10/2005 | Sisken et al. |
| 2005/0251252 A1 | 11/2005 | Stobie |
| 2005/0283231 A1 | 12/2005 | Haug et al. |
| 2006/0025857 A1 | 2/2006 | Bergheim et al. |
| 2006/0052867 A1 | 3/2006 | Revuelta et al. |
| 2006/0058872 A1 | 3/2006 | Salahieh et al. |
| 2006/0074484 A1 | 4/2006 | Huber |
| 2006/0085060 A1 | 4/2006 | Campbell |
| 2006/0122634 A1 | 6/2006 | Ino et al. |
| 2006/0122692 A1 | 6/2006 | Gilad et al. |
| 2006/0149360 A1 | 7/2006 | Schwammenthal et al. |
| 2006/0161249 A1 | 7/2006 | Realyvasquez et al. |
| 2006/0195183 A1 | 8/2006 | Navia et al. |
| 2006/0195184 A1 | 8/2006 | Lane et al. |
| 2006/0195185 A1 | 8/2006 | Lane et al. |
| 2006/0195186 A1 | 8/2006 | Drews et al. |
| 2006/0229708 A1 | 10/2006 | Powell et al. |
| 2006/0235508 A1 | 10/2006 | Lane et al. |
| 2006/0241745 A1 | 10/2006 | Solem |
| 2006/0253191 A1 | 11/2006 | Salahieh et al. |
| 2006/0259135 A1 | 11/2006 | Navia et al. |
| 2006/0259136 A1 | 11/2006 | Nguyen et al. |
| 2006/0259137 A1 | 11/2006 | Artof et al. |
| 2006/0265056 A1 | 11/2006 | Nguyen et al. |
| 2006/0271172 A1 | 11/2006 | Tehrani |
| 2006/0271175 A1 | 11/2006 | Woolfson et al. |
| 2006/0287717 A1 | 12/2006 | Rowe et al. |
| 2006/0293745 A1 | 12/2006 | Carpentier et al. |
| 2007/0010876 A1 | 1/2007 | Salahieh et al. |
| 2007/0010877 A1 | 1/2007 | Salahieh et al. |
| 2007/0016285 A1 | 1/2007 | Lane et al. |
| 2007/0016286 A1 | 1/2007 | Herrmann et al. |
| 2007/0016288 A1 | 1/2007 | Gurskis et al. |
| 2007/0043435 A1 | 2/2007 | Seguin et al. |
| 2007/0078509 A1 | 4/2007 | Lotfy |
| 2007/0078510 A1 | 4/2007 | Ryan |
| 2007/0100421 A1 | 5/2007 | Griffin |
| 2007/0100440 A1 | 5/2007 | Figulla et al. |
| 2007/0129794 A1 | 6/2007 | Realyvasquez |
| 2007/0142907 A1 | 6/2007 | Moaddeb et al. |
| 2007/0150053 A1 | 6/2007 | Gurskis et al. |
| 2007/0156233 A1 | 7/2007 | Kapadia et al. |
| 2007/0162103 A1 | 7/2007 | Case et al. |
| 2007/0162111 A1 | 7/2007 | Fukamachi et al. |
| 2007/0203575 A1 | 8/2007 | Forster et al. |
| 2007/0203576 A1 | 8/2007 | Lee et al. |
| 2007/0213813 A1 | 9/2007 | Von Segesser et al. |
| 2007/0225801 A1 | 9/2007 | Drews et al. |
| 2007/0239269 A1 | 10/2007 | Dolan et al. |
| 2007/0244546 A1 | 10/2007 | Francis |
| 2007/0260305 A1 | 11/2007 | Drews et al. |
| 2007/0265701 A1 | 11/2007 | Gurskis et al. |
| 2007/0270751 A1 | 11/2007 | Stangenes et al. |
| 2007/0270944 A1 | 11/2007 | Bergheim et al. |
| 2007/0282436 A1 | 12/2007 | Pinchuk |
| 2008/0021546 A1 | 1/2008 | Patz et al. |
| 2008/0033543 A1 | 2/2008 | Gurskis et al. |
| 2008/0033570 A1 | 2/2008 | Blitz et al. |
| 2008/0065011 A1 | 3/2008 | Marchand et al. |
| 2008/0082161 A1 | 4/2008 | Woo |
| 2008/0119875 A1 | 5/2008 | Ino et al. |
| 2008/0154356 A1 | 6/2008 | Obermiller et al. |
| 2008/0281411 A1 | 11/2008 | Berreklouw |
| 2009/0036903 A1 | 2/2009 | Ino et al. |
| 2009/0138079 A1 | 5/2009 | Tuval et al. |
| 2009/0192518 A1 | 7/2009 | Golden et al. |
| 2009/0192602 A1 | 7/2009 | Kuehn |
| 2009/0192603 A1 | 7/2009 | Kuehn |
| 2009/0192604 A1 | 7/2009 | Gloss |
| 2009/0192605 A1 | 7/2009 | Gloss et al. |
| 2009/0192606 A1 | 7/2009 | Gloss et al. |

(56) References Cited

U.S. PATENT DOCUMENTS

| | | |
|---|---|---|
| 2010/0161036 A1 | 6/2010 | Pintor et al. |
| 2010/0234940 A1 | 9/2010 | Dolan |
| 2010/0249894 A1 | 9/2010 | Oba et al. |
| 2010/0249908 A1 | 9/2010 | Chau et al. |
| 2010/0268226 A1* | 10/2010 | Epp .................... A61B 18/1492 606/45 |
| 2010/0292784 A1 | 11/2010 | Giannetti et al. |
| 2010/0331972 A1 | 12/2010 | Pintor et al. |
| 2011/0022165 A1 | 1/2011 | Oba et al. |
| 2011/0066234 A1 | 3/2011 | Gordon et al. |
| 2011/0098804 A1 | 4/2011 | Yeung et al. |
| 2011/0147251 A1 | 6/2011 | Hodshon et al. |
| 2011/0245917 A1 | 10/2011 | Savage et al. |
| 2012/0022633 A1 | 1/2012 | Olson et al. |
| 2012/0065729 A1 | 3/2012 | Pintor et al. |
| 2012/0078357 A1 | 3/2012 | Conklin |
| 2012/0083875 A1 | 4/2012 | Johnson et al. |
| 2012/0150288 A1 | 6/2012 | Hodshon et al. |
| 2013/0018449 A1 | 1/2013 | Bailey et al. |
| 2013/0053949 A1 | 2/2013 | Pintor et al. |
| 2013/0116777 A1 | 5/2013 | Pintor et al. |
| 2013/0190862 A1 | 7/2013 | Pintor et al. |

FOREIGN PATENT DOCUMENTS

| | | |
|---|---|---|
| EP | 0143246 A2 | 6/1985 |
| EP | 0179562 A1 | 4/1986 |
| EP | 1171059 A1 | 1/2002 |
| EP | 2250976 A1 | 11/2010 |
| GB | 414443 A | 8/1934 |
| GB | 2056023 A | 3/1981 |
| GB | 2 069 843 A | 9/1981 |
| GB | 2254254 A | 10/1992 |
| GB | 2 279 134 A | 12/1994 |
| WO | 8900840 A1 | 2/1989 |
| WO | 9115167 A1 | 10/1991 |
| WO | 9212690 A1 | 8/1992 |
| WO | 9213502 A1 | 8/1992 |
| WO | 9219184 A1 | 11/1992 |
| WO | 9219185 A1 | 11/1992 |
| WO | 9517139 A1 | 6/1995 |
| WO | 9528899 A1 | 11/1995 |
| WO | 9640006 A1 | 12/1996 |
| WO | 9709933 A1 | 3/1997 |
| WO | 9709944 A1 | 3/1997 |
| WO | 9727799 A1 | 8/1997 |
| WO | 9741801 A1 | 11/1997 |
| WO | 9742871 A1 | 11/1997 |
| WO | 9806329 A1 | 2/1998 |
| WO | 9911201 A2 | 3/1999 |
| WO | 9915112 A1 | 4/1999 |
| WO | 9951169 A1 | 10/1999 |
| WO | 0032105 A1 | 6/2000 |
| WO | 0040176 A1 | 7/2000 |
| WO | 0060995 A2 | 10/2000 |
| WO | 0154624 A1 | 8/2001 |
| WO | 0154625 A1 | 8/2001 |
| WO | 02076347 | 10/2002 |
| WO | 2006086135 A2 | 8/2006 |
| WO | 2006127756 A2 | 11/2006 |
| WO | 2013028387 A2 | 2/2013 |

OTHER PUBLICATIONS

Sadowski, Jerzy; Kapelak, Boguslaw; Bartus, Krzysztof, "Sutureless Heart Valve Implantation—A Case Study," Touch Briefings, 2005, pp. 48-50.

* cited by examiner

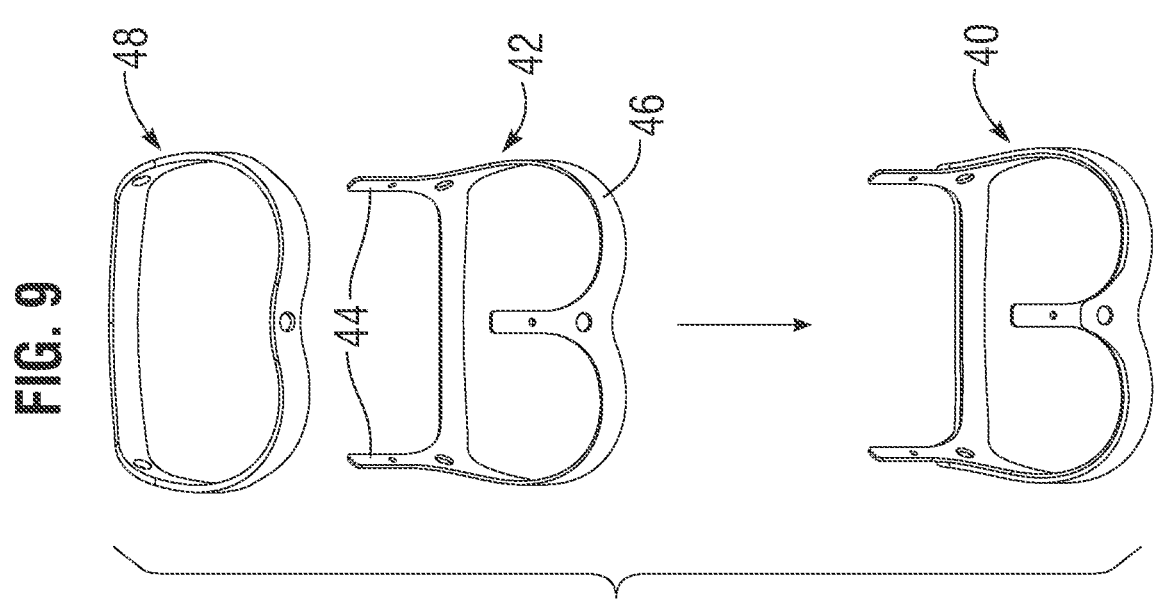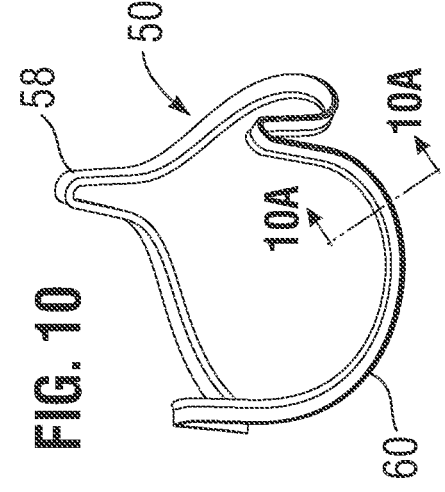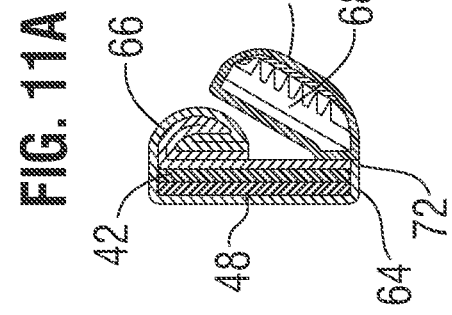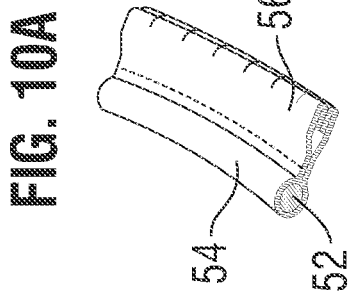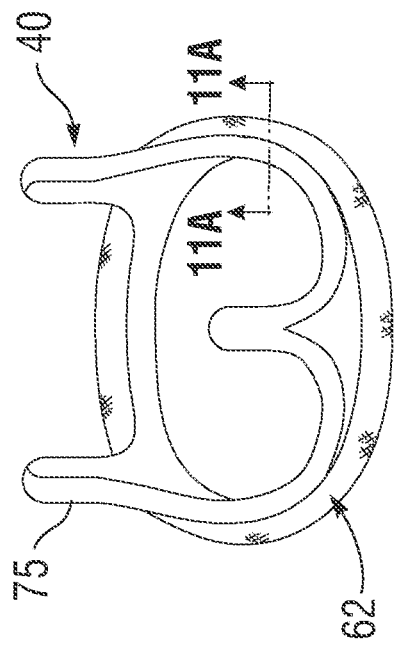

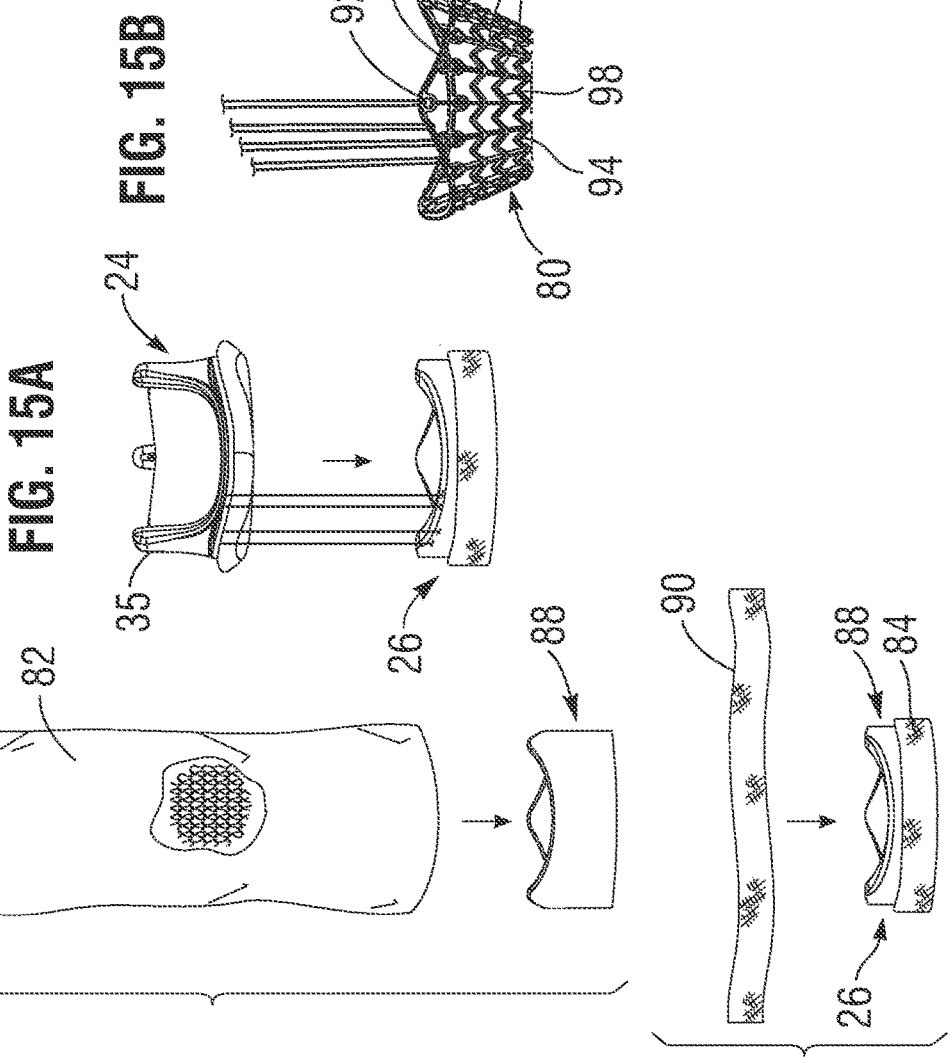

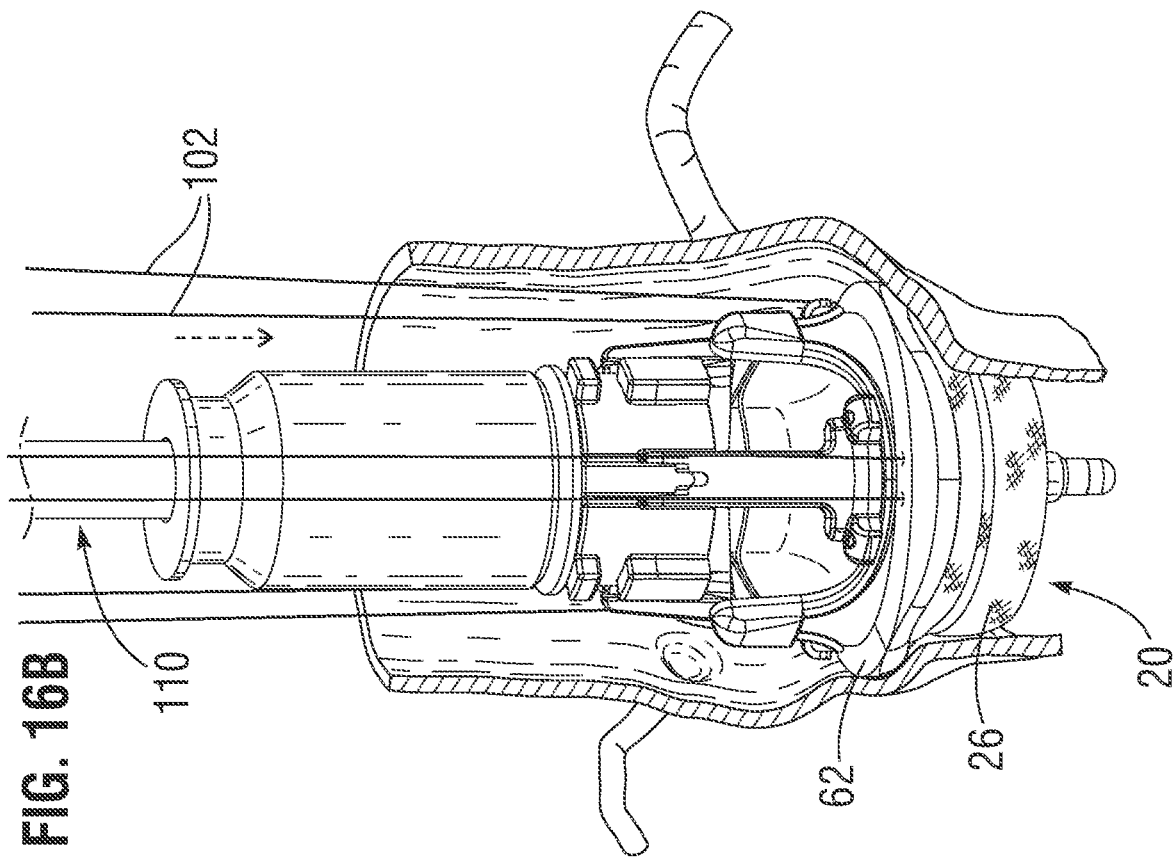
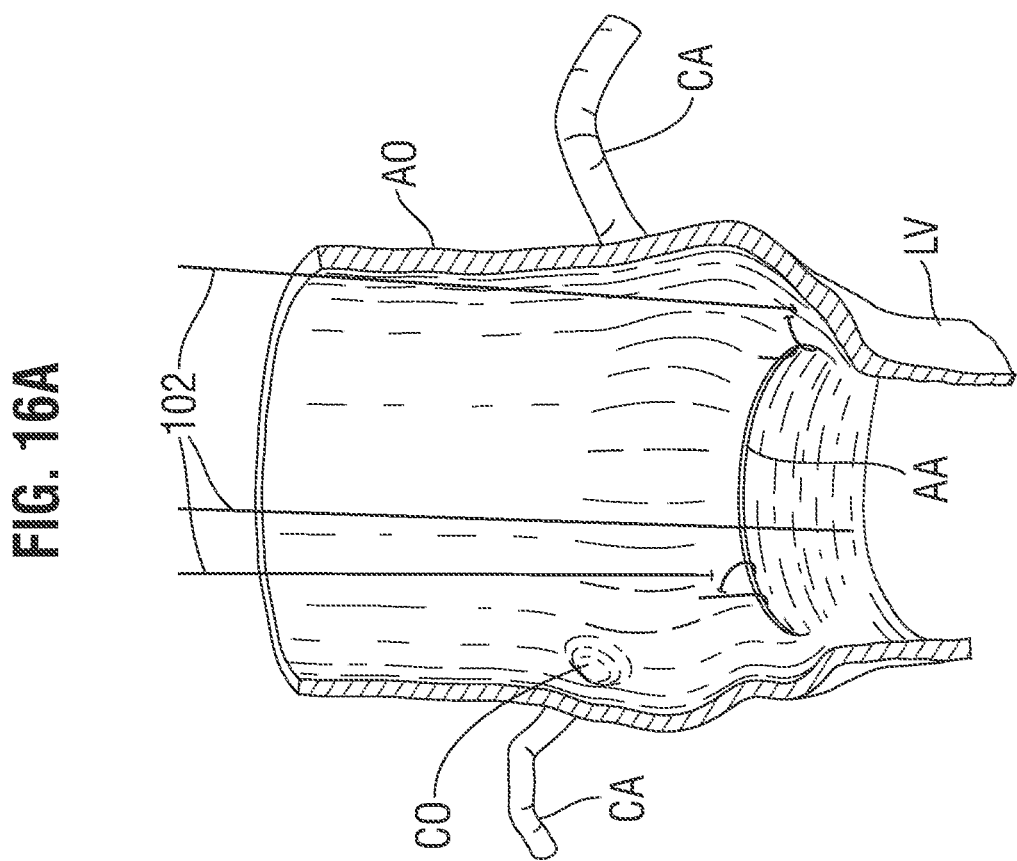

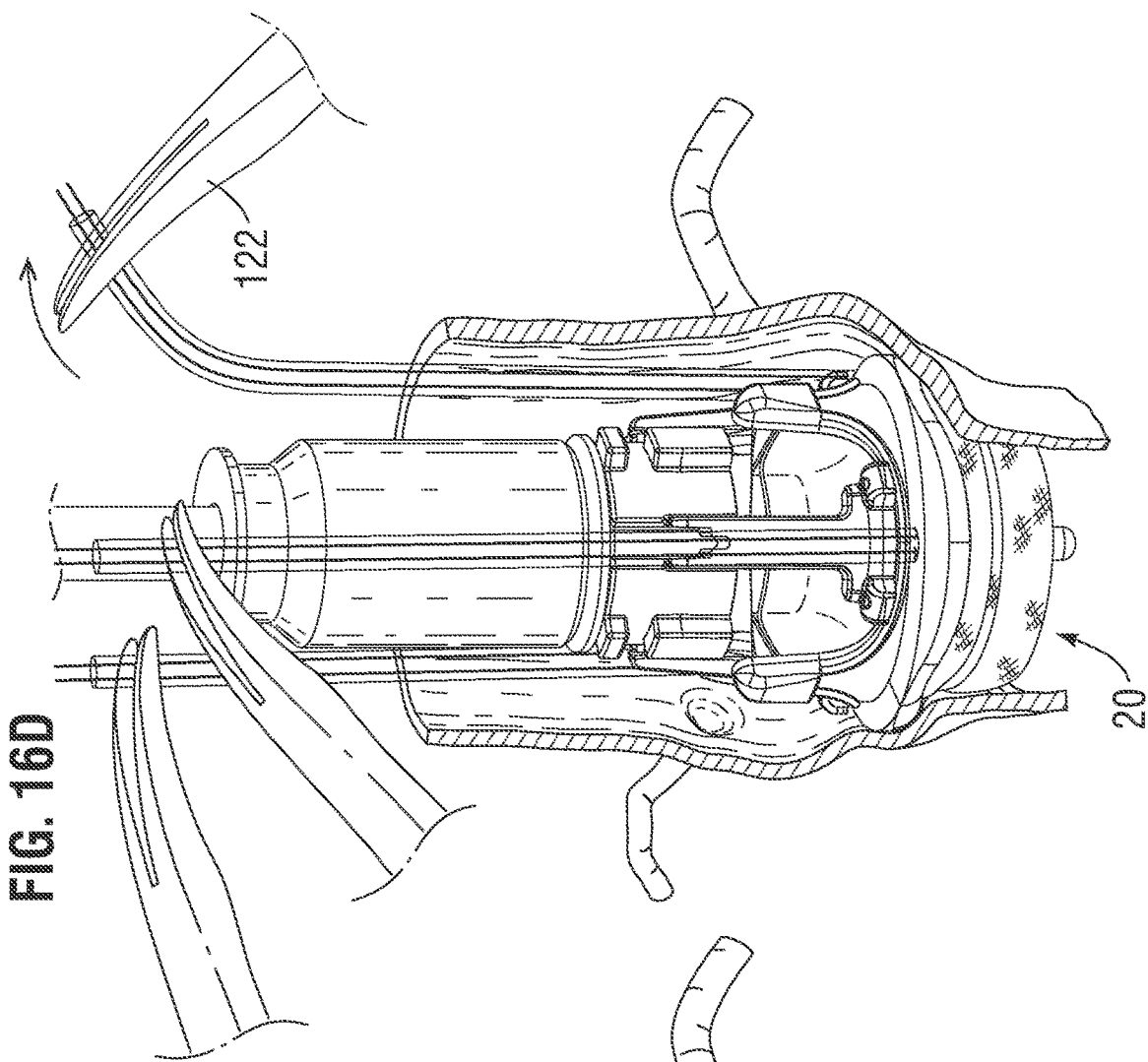
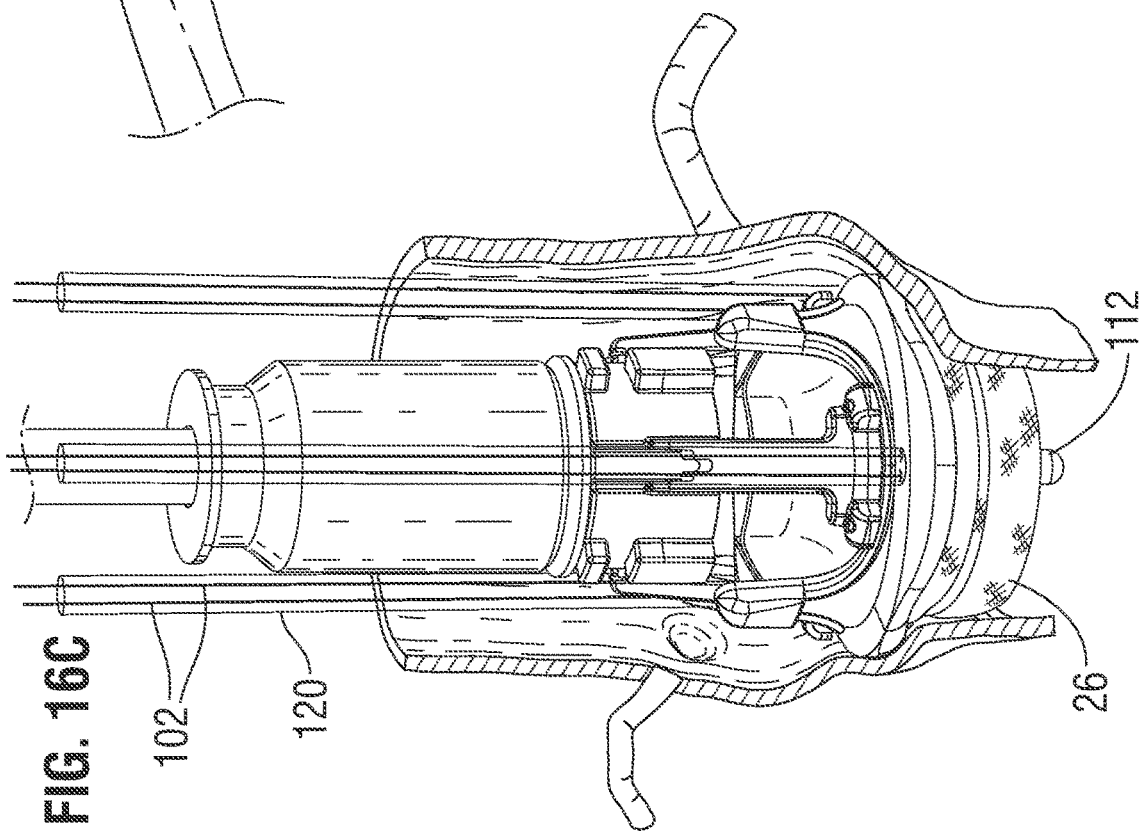

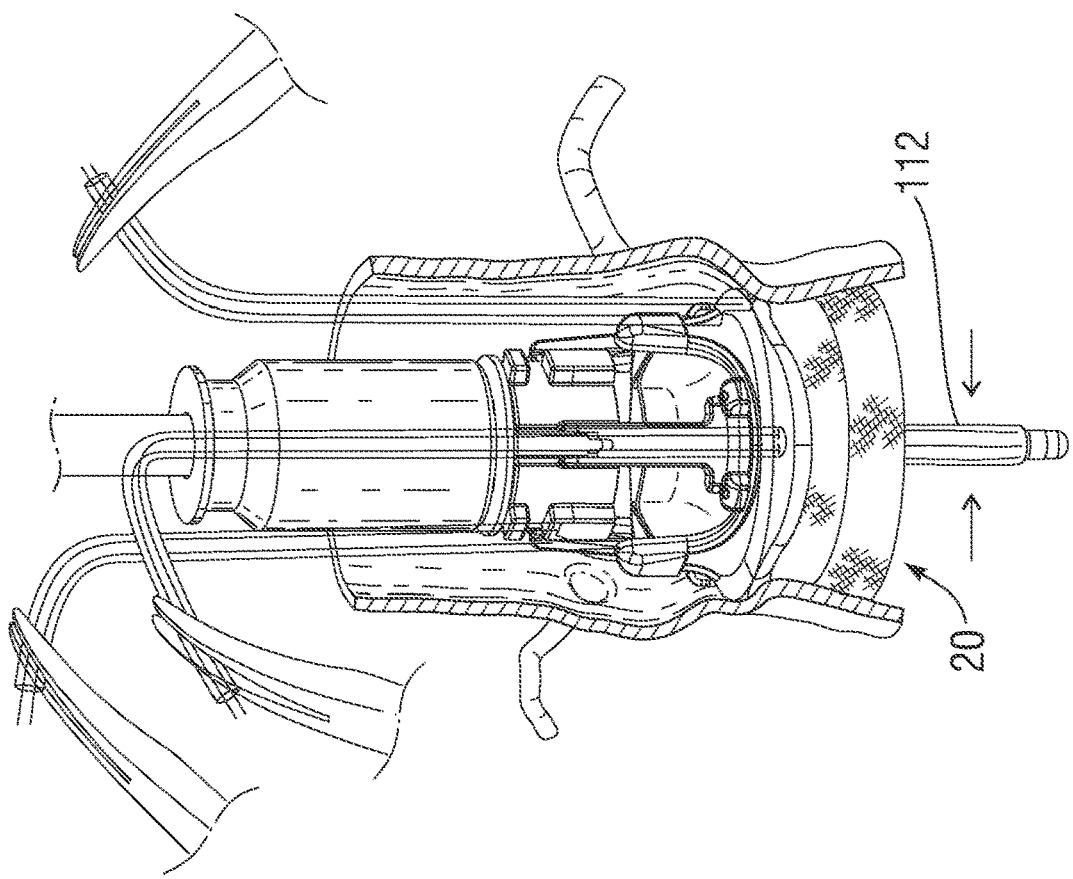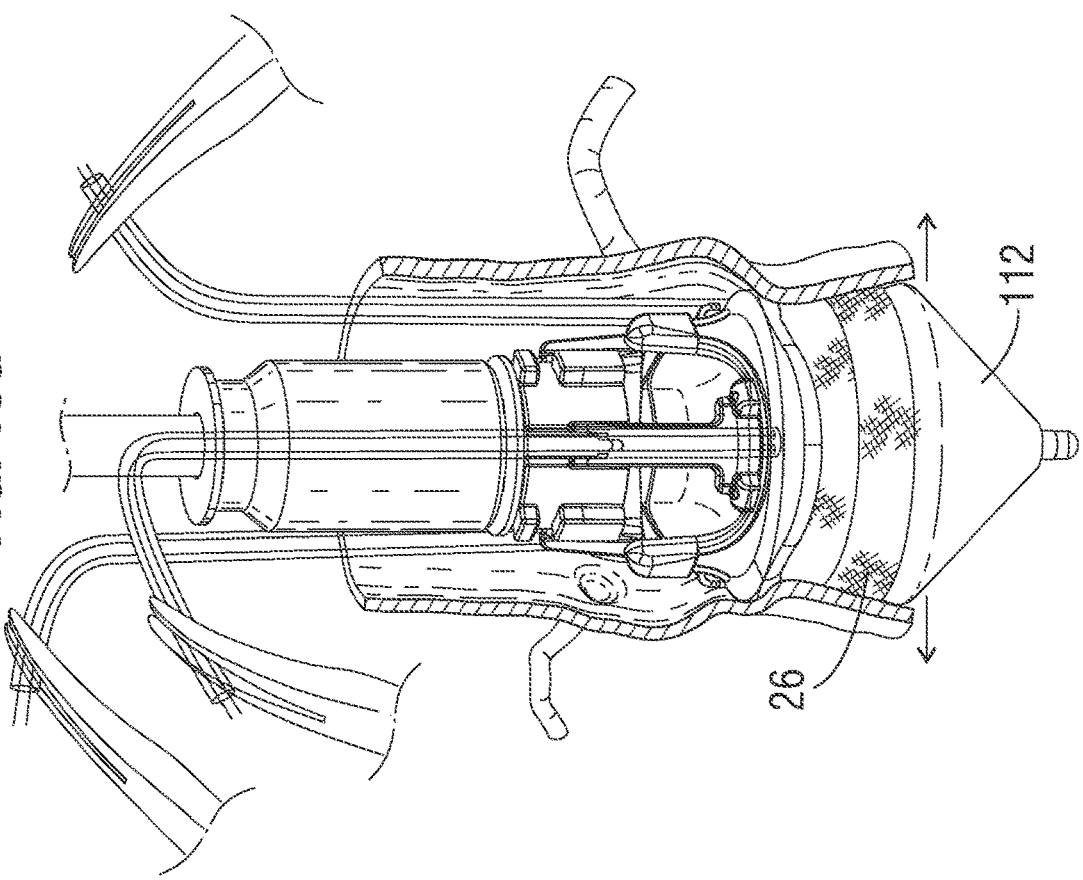

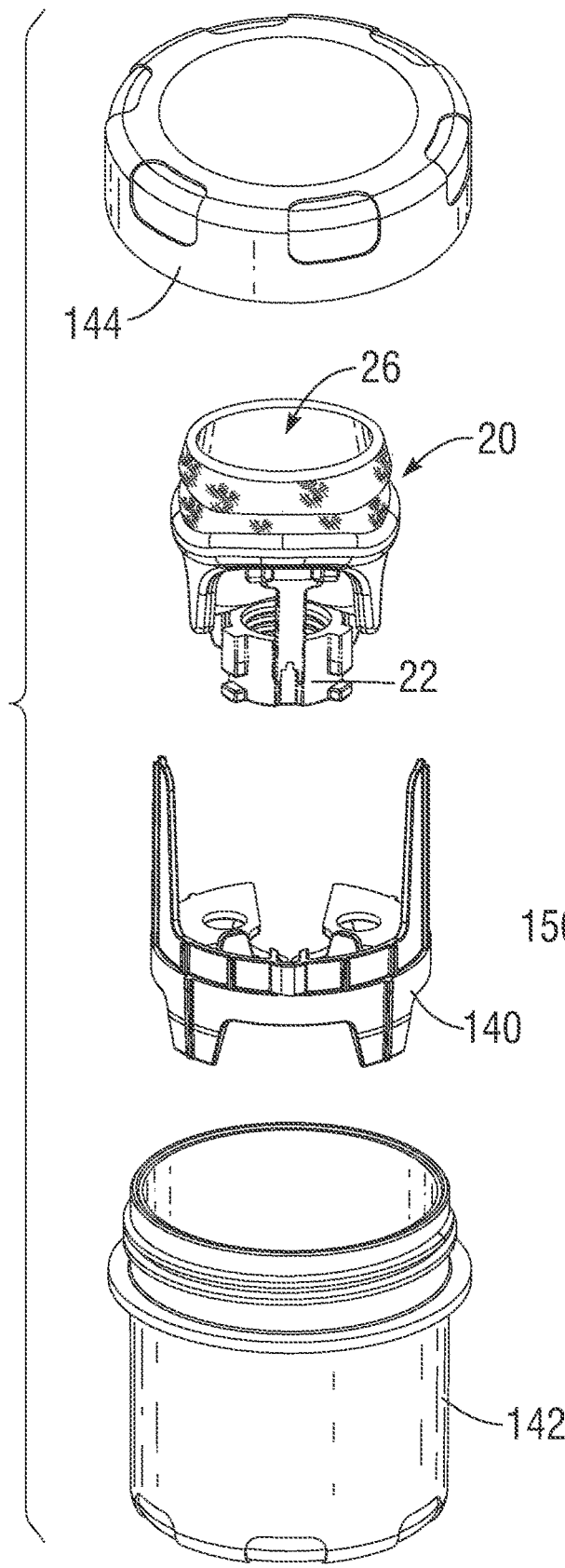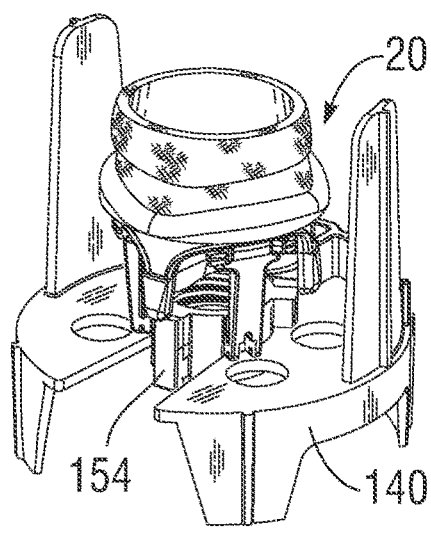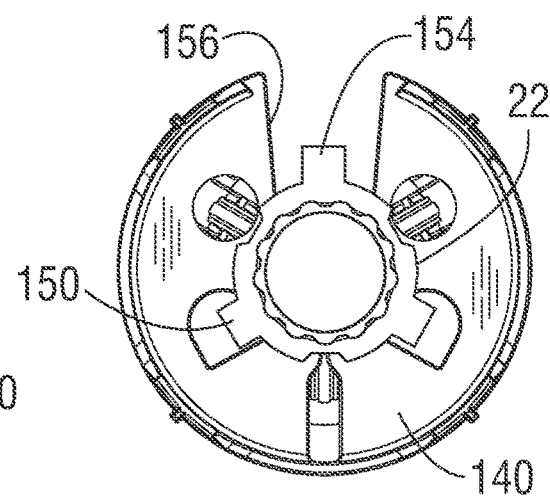

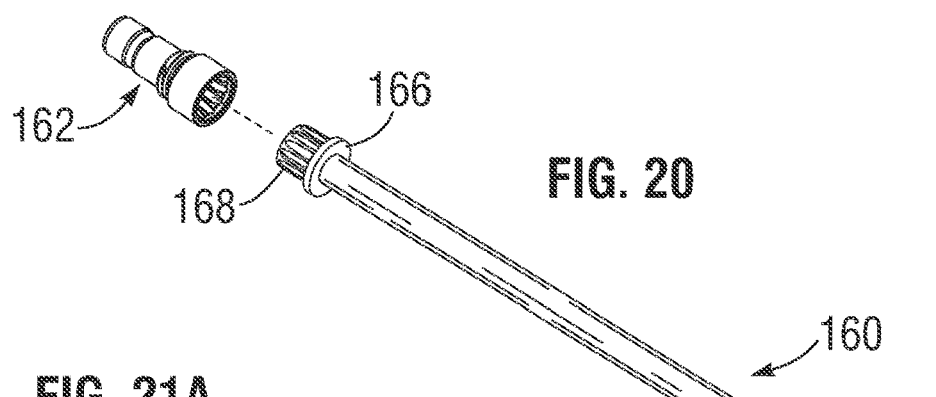
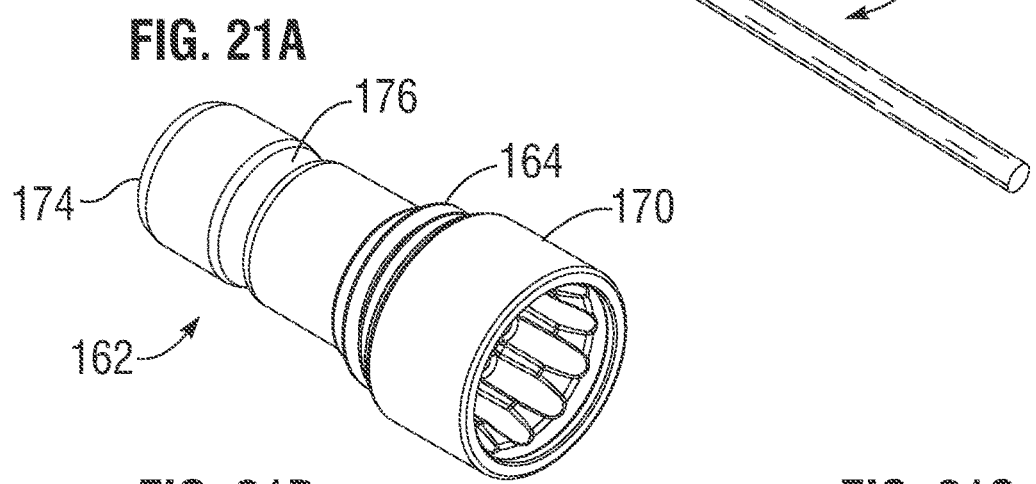
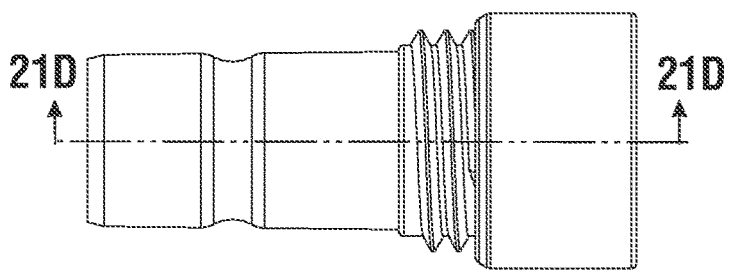
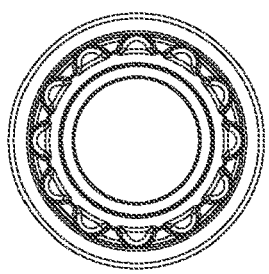
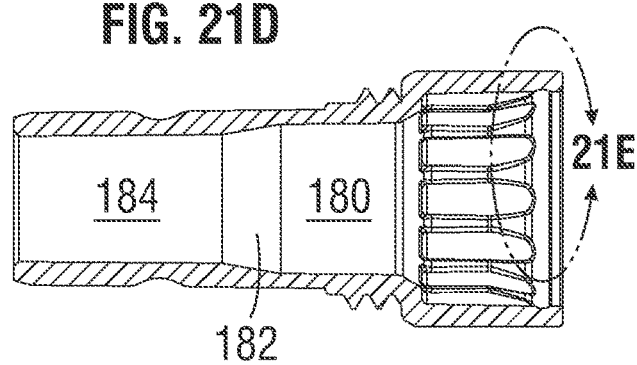
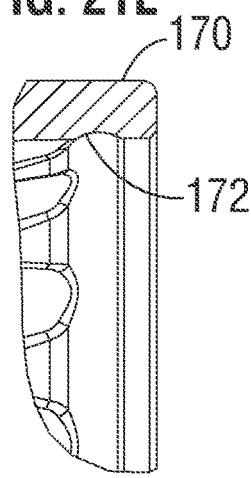

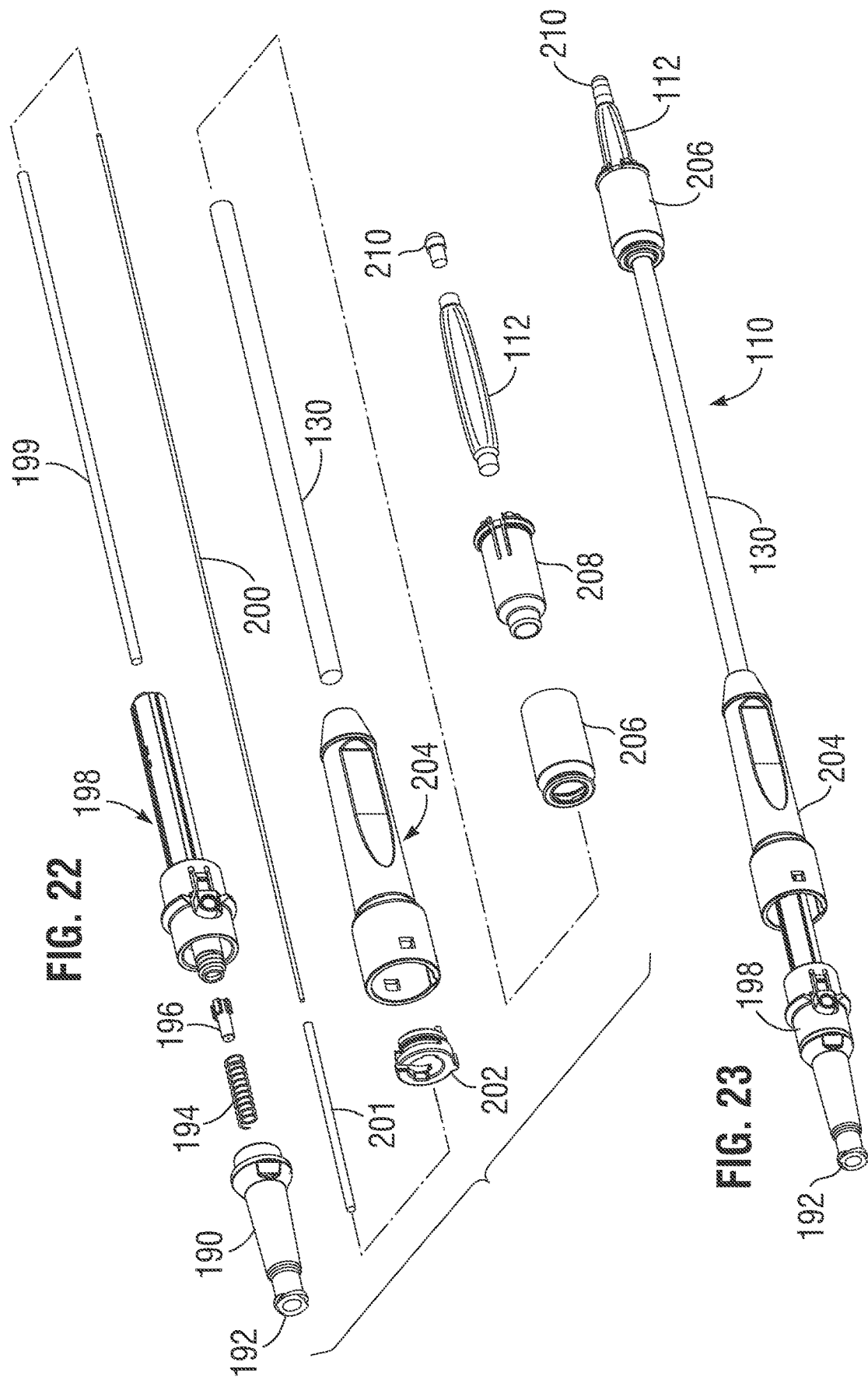

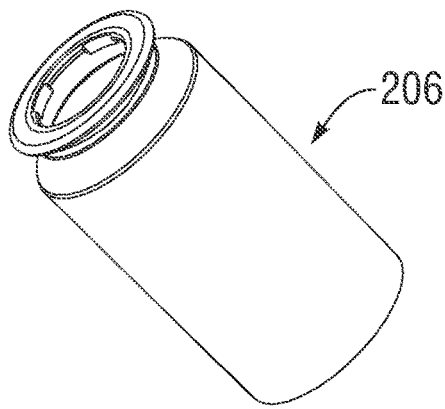
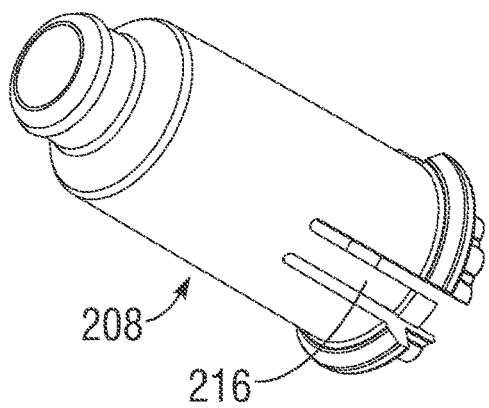
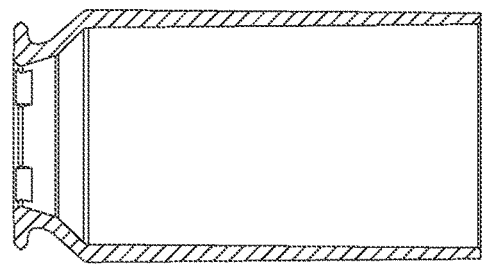
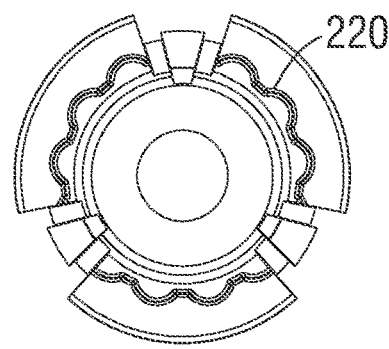
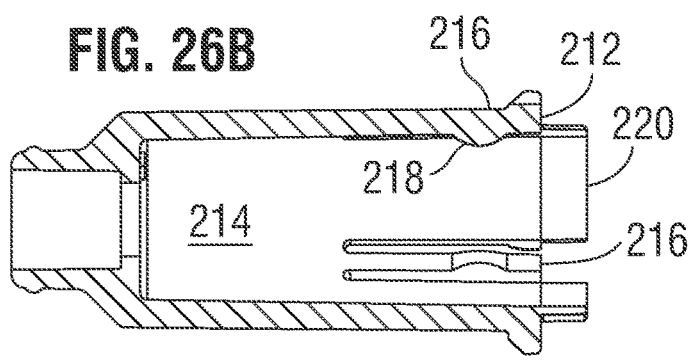
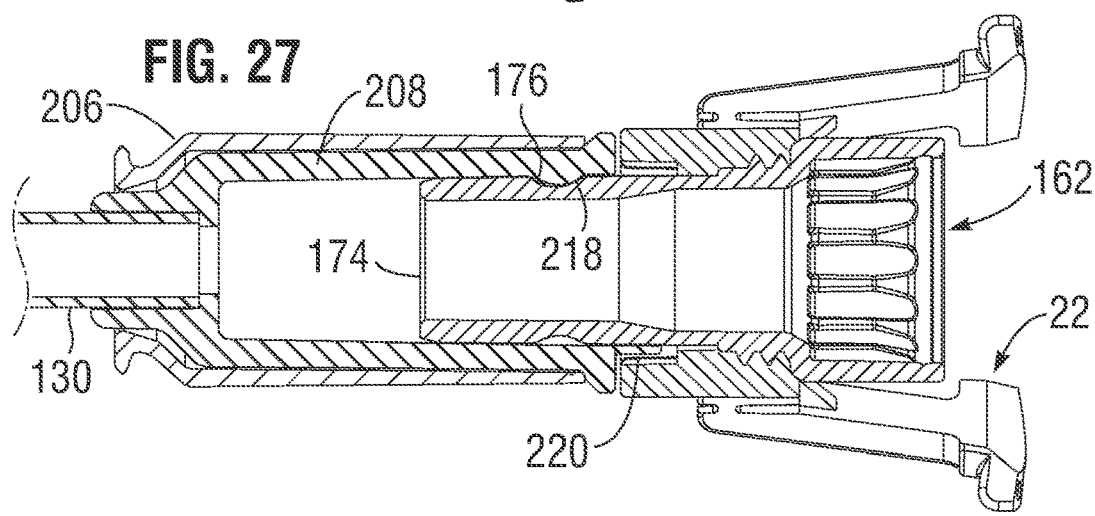

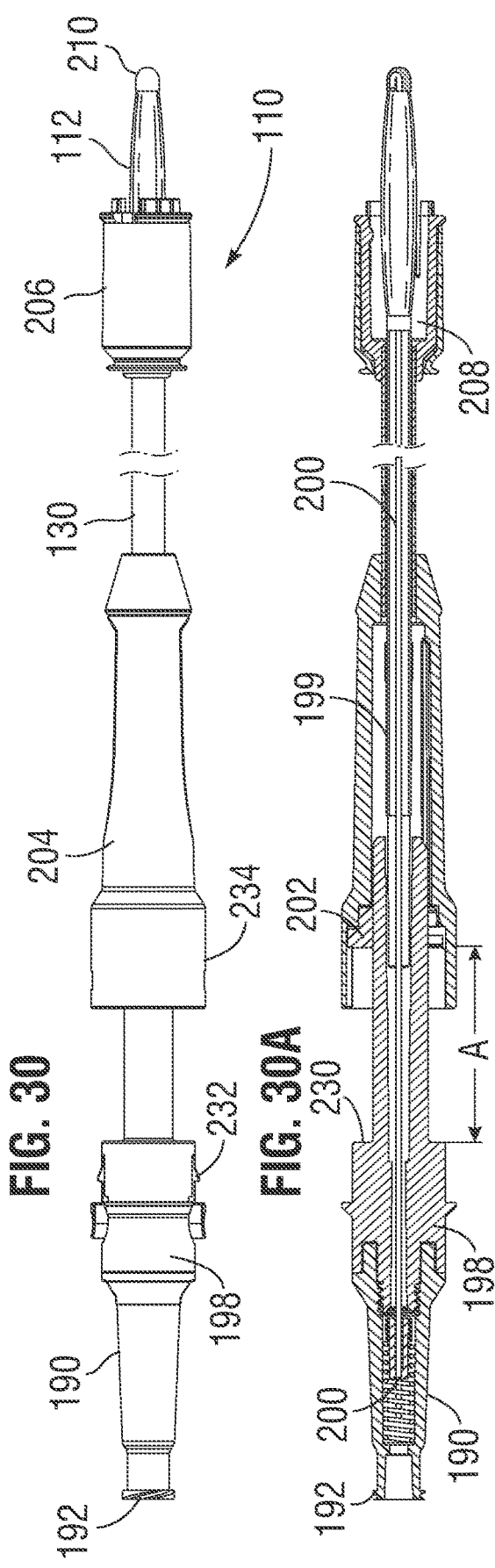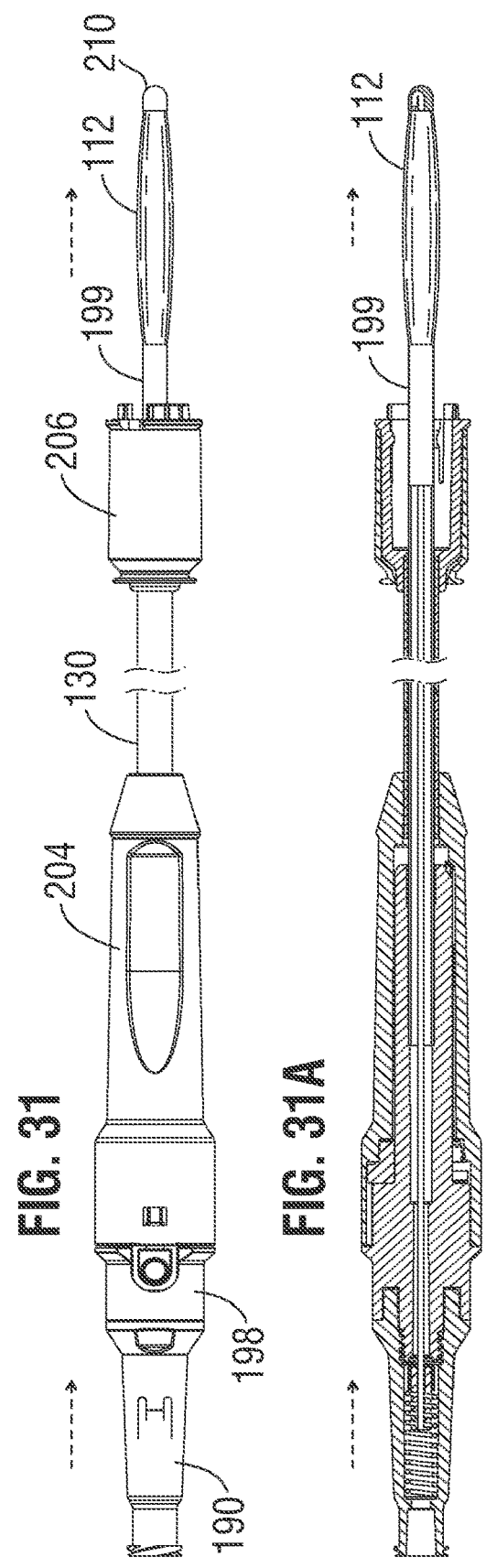

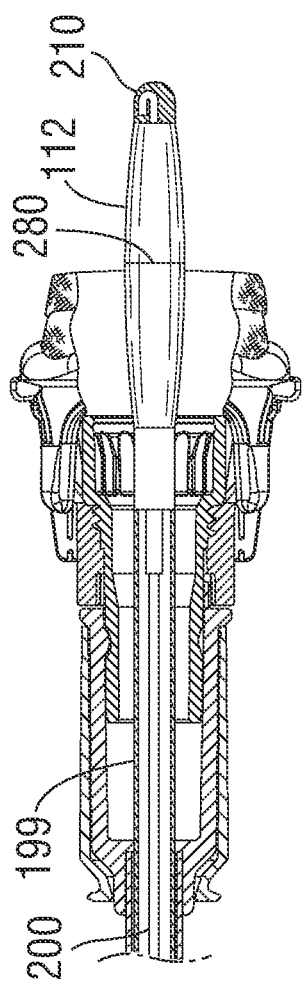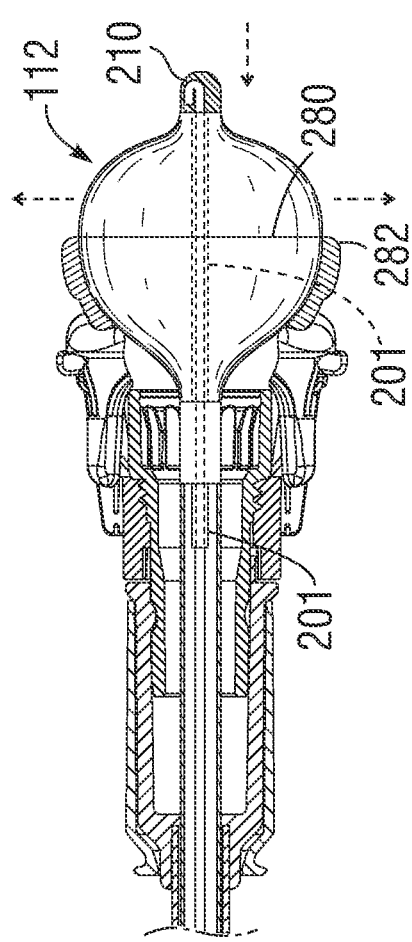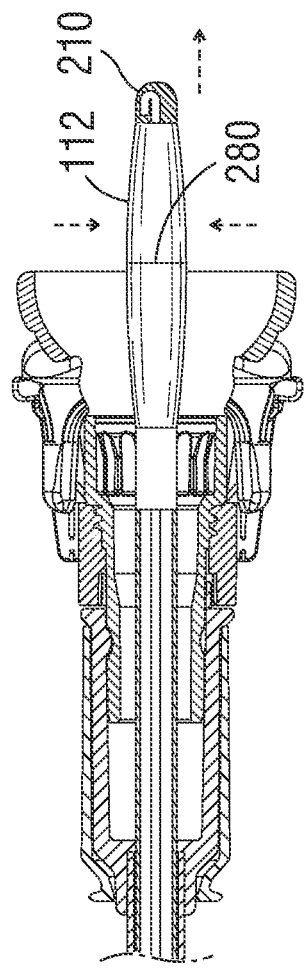
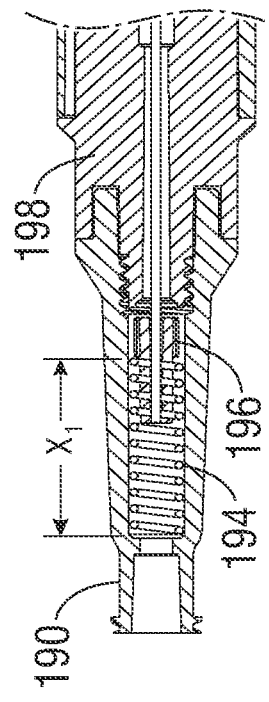
FIG. 38
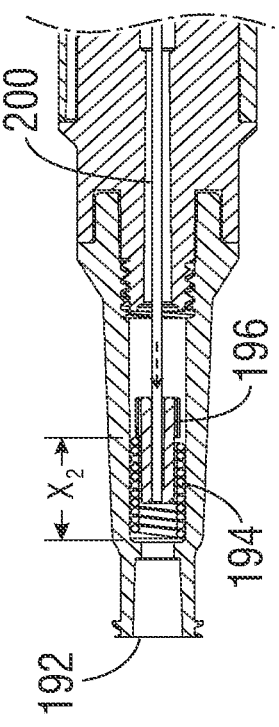
FIG. 39
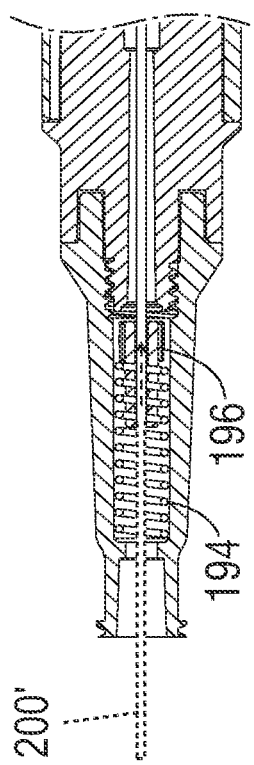
FIG. 40

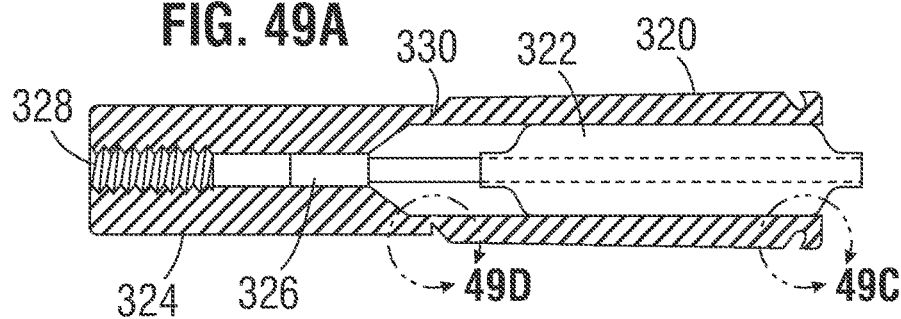
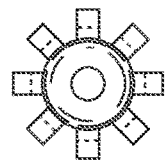
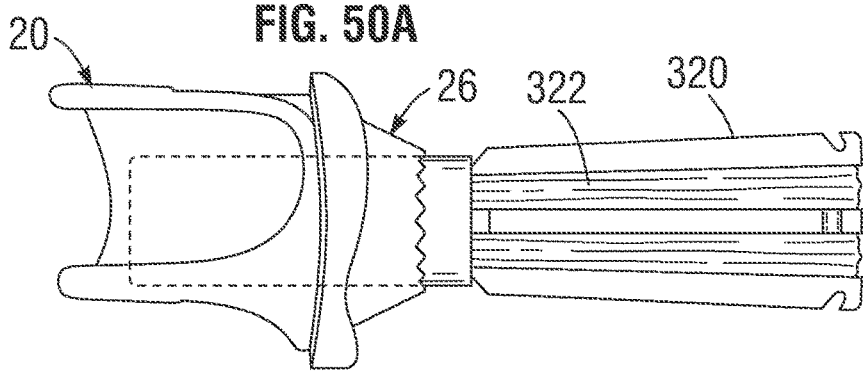
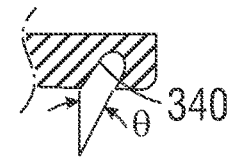
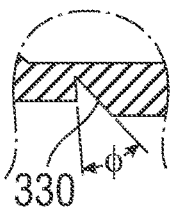
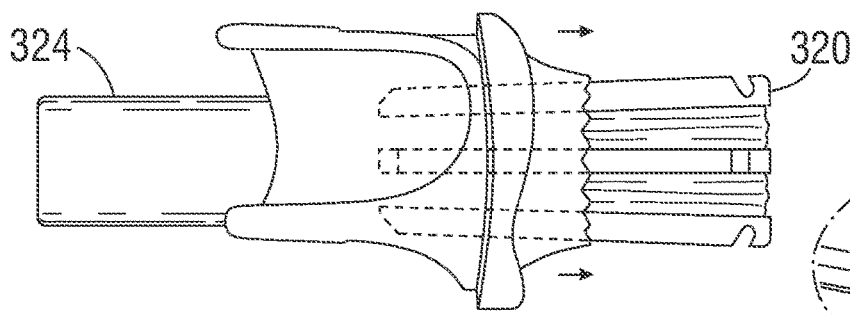
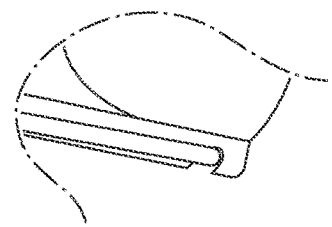
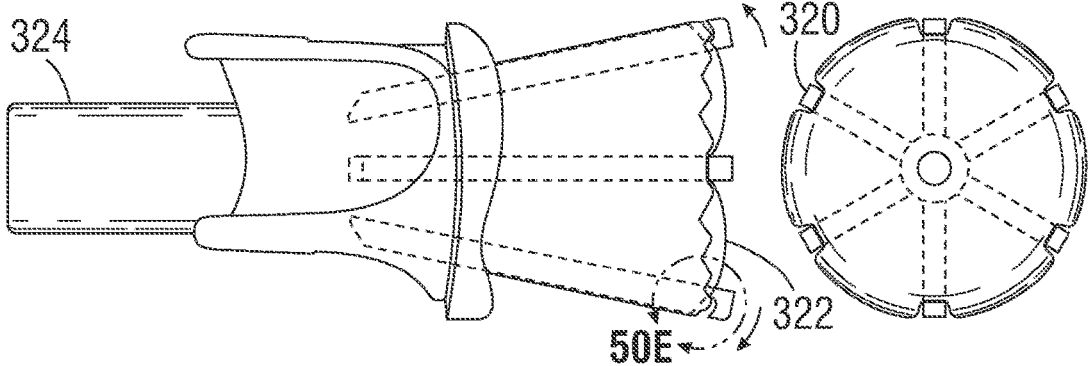
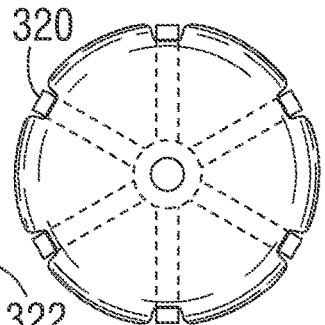

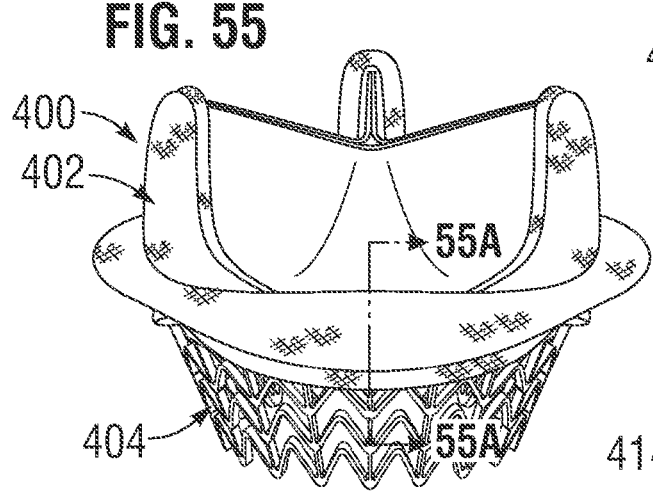
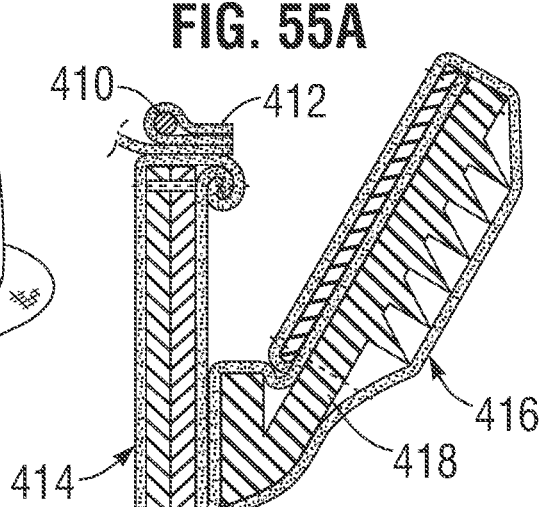
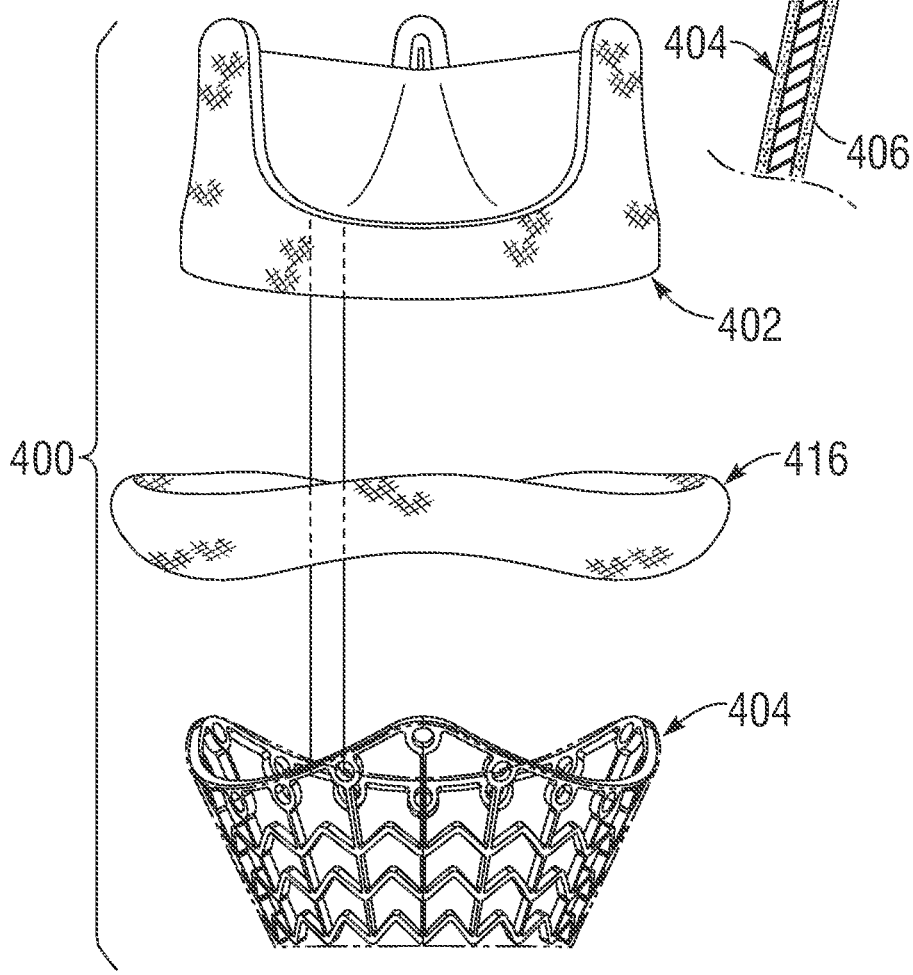

SYSTEMS FOR RAPIDLY DEPLOYABLE SURGICAL HEART VALVES

CROSS REFERENCE TO RELATED APPLICATIONS

This application is a continuation of U.S. patent application Ser. No. 16/056,252, filed Aug. 6, 2018, now U.S. Pat. No. 10,722,358, which is a continuation of U.S. patent application Ser. No. 15/360,483, filed Nov. 23, 2016, now U.S. Pat. No. 10,039,641, which is a continuation of U.S. patent application Ser. No. 14/164,764, filed Jan. 27, 2014, now U.S. Pat. No. 9,504,563, which is a divisional of U.S. patent application Ser. No. 13/167,639, filed Jun. 23, 2011, now U.S. Pat. No. 8,641,757, which claims the benefit of U.S. Patent Application No. 61/381,931 filed Sep. 10, 2010, the entire disclosures all of which are incorporated by reference herein for all purposes.

FIELD OF THE INVENTION

The present invention generally relates to prosthetic valves for implantation in body channels. More particularly, the present invention relates to unitary surgical prosthetic heart valves configured to be surgically implanted in less time than current valves, and associated valve delivery systems and methods.

BACKGROUND OF THE INVENTION

In vertebrate animals, the heart is a hollow muscular organ having four pumping chambers as seen in FIG. 1—the left and right atria and the left and right ventricles, each provided with its own one-way valve. The natural heart valves are identified as the aortic, mitral (or bicuspid), tricuspid and pulmonary, and are each mounted in an annulus comprising dense fibrous rings attached either directly or indirectly to the atrial and ventricular muscle fibers. Each annulus defines a flow orifice.

The atria are the blood-receiving chambers, which pump blood into the ventricles. The ventricles are the blood-discharging chambers. A wall composed of fibrous and muscular parts, called the interatrial septum separates the right and left atria (see FIGS. 2 to 4). The fibrous interatrial septum is a materially stronger tissue structure compared to the more friable muscle tissue of the heart. An anatomic landmark on the interatrial septum is an oval, thumbprint sized depression called the oval fossa, or fossa ovalis (shown in FIG. 4).

The synchronous pumping actions of the left and right sides of the heart constitute the cardiac cycle. The cycle begins with a period of ventricular relaxation, called ventricular diastole. The cycle ends with a period of ventricular contraction, called ventricular systole. The four valves (see FIGS. 2 and 3) ensure that blood does not flow in the wrong direction during the cardiac cycle; that is, to ensure that the blood does not back flow from the ventricles into the corresponding atria, or back flow from the arteries into the corresponding ventricles. The mitral valve is between the left atrium and the left ventricle, the tricuspid valve between the right atrium and the right ventricle, the pulmonary valve is at the opening of the pulmonary artery, and the aortic valve is at the opening of the aorta.

FIGS. 2 and 3 show the anterior (A) portion of the mitral valve annulus abutting the non-coronary leaflet of the aortic valve. The mitral valve annulus is in the vicinity of the circumflex branch of the left coronary artery, and the posterior (P) side is near the coronary sinus and its tributaries.

Various surgical techniques may be used to repair a diseased or damaged valve. In a valve replacement operation, the damaged leaflets are excised and the annulus sculpted to receive a replacement valve. Due to aortic stenosis and other heart valve diseases, thousands of patients undergo surgery each year wherein the defective native heart valve is replaced by a prosthetic valve, either bioprosthetic or mechanical. Another less drastic method for treating defective valves is through repair or reconstruction, which is typically used on minimally calcified valves. The problem with surgical therapy is the significant insult it imposes on these chronically ill patients with high morbidity and mortality rates associated with surgical repair.

When the valve is replaced, surgical implantation of the prosthetic valve typically requires an open-chest surgery during which the heart is stopped and patient placed on cardiopulmonary bypass (a so-called "heart-lung machine"). In one common surgical procedure, the diseased native valve leaflets are excised and a prosthetic valve is sutured to the surrounding tissue at the valve annulus. Because of the trauma associated with the procedure and the attendant duration of extracorporeal blood circulation, some patients do not survive the surgical procedure or die shortly thereafter. It is well known that the risk to the patient increases with the amount of time required on extracorporeal circulation. Due to these risks, a substantial number of patients with defective valves are deemed inoperable because their condition is too frail to withstand the procedure. By some estimates, about 30 to 50% of the subjects suffering from aortic stenosis who are older than 80 years cannot be operated on for aortic valve replacement.

Because of the drawbacks associated with conventional open-heart surgery, percutaneous and minimally-invasive surgical approaches are garnering intense attention. In one technique, a prosthetic valve is configured to be implanted in a much less invasive procedure by way of catheterization. For instance, U.S. Pat. No. 5,411,552 to Andersen et al. describes a collapsible valve percutaneously introduced in a compressed state through a catheter and expanded in the desired position by balloon inflation. Although these remote implantation techniques have shown great promise for treating certain patients, replacing a valve via surgical intervention is still the preferred treatment procedure. One hurdle to the acceptance of remote implantation is resistance from doctors who are understandably anxious about converting from an effective, if imperfect, regimen to a novel approach that promises great outcomes but is relatively foreign. In conjunction with the understandable caution exercised by surgeons in switching to new techniques of heart valve replacement, regulatory bodies around the world are moving slowly as well. Numerous successful clinical trials and follow-up studies are in process, but much more experience with these new technologies will be required before they are completely accepted.

Accordingly, there is a need for an improved device and associated method of use wherein a prosthetic valve can be surgically implanted in a body channel in a more efficient procedure that reduces the time required on extracorporeal circulation. It is desirable that such a device and method be capable of helping patients with defective valves that are deemed inoperable because their condition is too frail to withstand a lengthy conventional surgical procedure.

Furthermore, surgeons relate that one of the most difficult tasks when attempting minimally invasive heart valve implantation or implantation through a small incision is tying the suture knots that hold the valve in position. A typical aortic valve implant utilizes 12-24 sutures (commonly 15) distributed evenly around and manually tied on one side of the sewing ring. The knots directly behind the commissure posts of a prosthetic aortic valve are particularly challenging because of space constraints. Eliminating the need to tie suture knots or even reducing the number of knots to those that are more accessible would greatly facilitate the use of smaller incisions that reduces infection risk, reduces the need for blood transfusions and allows more rapid recovery compared to patients whose valves are implanted through the full sternotomy commonly used for heart valve implantation.

The present invention addresses these needs and others.

SUMMARY OF THE INVENTION

Various embodiments of the present application provide prosthetic valves and methods of use for replacing a defective native valve in a human heart. Certain embodiments are particularly well adapted for use in a surgical procedure for quickly and easily replacing a heart valve while minimizing time using extracorporeal circulation (i.e., bypass pump).

In one embodiment, a method for treating a native aortic valve in a human heart to replace the function of the aortic valve, comprises: 1) accessing a native valve through an opening in a chest; 2) placing guiding sutures in the annulus 3) advancing a heart valve within a lumen of the annulus; and 4) plastically expanding a metallic anchoring skirt on the heart valve to mechanically couple to the annulus in a quick and efficient manner.

The native valve leaflets may be removed before delivering the prosthetic valve. Alternatively, the native leaflets may be left in place to reduce surgery time and to provide a stable base for fixing the anchoring skirt within the native valve. In one advantage of this method, the native leaflets recoil inward to enhance the fixation of the metallic anchoring skirt in the body channel. When the native leaflets are left in place, a balloon or other expansion member may be used to push the valve leaflets out of the way and thereby dilate the native valve before implantation of the anchoring skirt. The native annulus may be dilated between 1.0-5 mm from their initial orifice size to accommodate a larger sized prosthetic valve.

In accordance with a preferred aspect, a heart valve includes a prosthetic valve defining therein a non-expandable, non-collapsible orifice, and an expandable anchoring skirt extending from an inflow end thereof. The anchoring skirt has a contracted state for delivery to an implant position and an expanded state configured for outward connection to the surrounding annulus. Desirably, the anchoring skirt is plastically expandable.

In another aspect, a prosthetic heart valve for implant at a heart valve annulus, comprises:

a non-expandable, non-collapsible annular support structure defining a flow orifice and having an inflow end;

valve leaflets attached to the support structure and mounted to alternately open and close across the flow orifice;

a plastically-expandable frame having a first end extending around the flow orifice and connected to the valve at the inflow end of the support structure, the frame having a second end projecting in the inflow direction away from the support structure and being capable of assuming a contracted state for delivery to an implant position and a wider expanded state for outward contact with an annulus; and a fabric covering around the plastically-expandable frame including an enlarged sealing flange surrounding the second end.

Preferably, the support structure includes a plurality of commissure posts projecting in an outflow direction, and the valve leaflets are flexible and attached to the support structure and commissure posts and mounted to alternately open and close across the flow orifice. Also, a sealing ring desirably circumscribes an inflow end of the support structure. The enlarged sealing flange surrounding the second end of the plastically-expandable frame is spaced from the suture permeable ring to help conform the frame to the aortic annulus.

In one embodiment, the heart valve comprises a commercially available prosthetic valve having a sewing ring, and the anchoring skirt attaches to the sewing ring. The contracted state of the anchoring skirt may be conical, tapering inward from the first end toward the second end, while in the expanded state the frame is conical but tapering outward from the first end toward the second end. The anchoring skirt preferably comprises a plurality of radially expandable struts at least some of which are arranged in rows, wherein the distalmost row has the greatest capacity for expansion from the contracted state to the expanded state. The sewing ring may comprise a solid yet compressible material that is relatively stiff so as to provide a seal against the annulus and has a concave inflow shape that conforms to the annulus.

A method of delivery and implant of a prosthetic heart valve system is also disclosed herein, comprising the steps of:

providing a heart valve including a prosthetic valve having an expandable frame, the frame having a contracted state for delivery to an implant position and an expanded state configured for outward connection to the annulus, the heart valve being mounted on a holder having a proximal hub and lumen therethrough, the proximal hub connected to the distal end of a handle shaft having a lumen therethrough, advancing the heart valve with the frame in its contracted state to an implant position adjacent the annulus;

passing a first balloon catheter through the lumens of the handle shaft and the holder and within the heart valve, and inflating a balloon on the first balloon catheter;

deflating the balloon and retracting the first balloon catheter from within the heart valve, and removing the first balloon catheter from the handle shaft;

inserting a second balloon catheter into the handle shaft and passing the second balloon catheter through the lumens of the handle shaft and the holder to within the heart valve, and inflating a balloon on the second balloon catheter to expand the frame.

The method may involve increasing the orifice size of the heart valve annulus by 1.0-5.0 mm by plastically expanding the frame. In one embodiment, the prosthetic valve of the valve component is selected to have an orifice size that matches the increased orifice size of the heart valve annulus.

The heart valve in the aforementioned method may include a non-expandable, non-collapsible orifice, with the expandable frame comprising an anchoring skirt extending from an inflow end thereof. The anchoring skirt may have a plurality of radially expandable struts, wherein a row farthest from the prosthetic valve has alternating peaks and valleys. The distal end of the anchoring skirt desirably has the greatest capacity for expansion from the contracted state to the expanded state so that the peaks in the row farthest from the prosthetic valve project outward into the surrounding left ventricular outflow tract.

One embodiment of the method further includes mounting the heart valve on a holder having a proximal hub and lumen therethrough. The holder mounts on the distal end of a handle shaft having a lumen therethrough, and the method includes passing a balloon catheter through the lumen of the handle shaft and the holder and within the heart valve, and inflating a balloon on the balloon catheter to expand the anchoring skirt. The heart valve mounted on the holder may be packaged separately from the handle shaft and the balloon catheter. Desirably, the contracted state of the expandable frame/anchoring skirt is conical, and the balloon on the balloon catheter has a larger distal expanded end than its proximal expanded end so as to apply expansion deflection to the anchoring skirt and not to the prosthetic valve. In a preferred embodiment, the balloon distal and proximal diameters are essentially the same, the balloon being generally symmetric across an axial midline, and the balloon midline is positioned near the distal end of the frame prior to inflation. The delivery system including the valve holder is designed to position the balloon within the heart valve so that it inflates within the anchoring skirt, and not within the actual valve components.

Preferably, a valve delivery system includes an integrated balloon catheter and tubular handle shaft through which the catheter extends. A distal end of the handle shaft includes an adapter which mates with a holder of the heart valve, and a locking sleeve for rapidly connecting the delivery system to the heart valve holder. A balloon of the balloon catheter resides within the adapter and may be advanced distally into position for expanding the anchoring skirt. A tubular balloon introducer sleeve attached when removing the heart valve from a storage jar facilitates passage of the balloon through the heart valve.

Another aspect described herein is a system for delivering a heart valve including a prosthetic valve having a non-expandable, non-collapsible orifice, and an expandable frame extending from an inflow end thereof, the frame having a contracted state for delivery to an implant position and an expanded state. The delivery system includes a valve holder connected to a proximal end of the heart valve, a balloon catheter having a balloon, and a malleable handle shaft configured to attach to a proximal end of the valve holder and having a lumen for passage of the catheter, the balloon extending distally through the handle shaft, past the holder and through the heart valve.

The balloon catheter desirably has an inflation tube that extends through the lumen of the handle shaft and the OD of the inflation tube is more than 90% the ID of the handle shaft lumen. The prosthetic valve may be a commercially available valve having a sewing ring, and wherein the frame attaches to the sewing ring. The contracted state of the frame is preferably conical, tapering down in a distal direction. Further, the balloon may include a visible midline that is positioned near the distal end of the frame prior to inflation. In a preferred embodiment, the heart valve mounted on the holder is packaged separately from the handle shaft and the balloon catheter. The malleable handle shaft may be made of aluminum.

In one embodiment, the expandable frame is an expandable anchoring skirt formed of plastically-deformable struts surrounded by a fabric cover, and an enlarged sealing flange surrounds the second end of the plastically-expandable frame spaced from a sewing permeable ring on the valve to help conform the frame to the aortic annulus.

A further understanding of the nature and advantages of the present invention are set forth in the following description and claims, particularly when considered in conjunction with the accompanying drawings in which like parts bear like reference numerals.

BRIEF DESCRIPTION OF THE DRAWINGS

The invention will now be explained and other advantages and features will appear with reference to the accompanying schematic drawings wherein:

FIG. 9 is an exploded view of an inner structural band subassembly of the exemplary prosthetic heart valve;

FIG. 10 is a perspective view of a further valve subassembly of an undulating cloth-covered wireform, and FIG. 10A is a detailed sectional view of a cusp portion thereof;

FIG. 11 is a perspective view of the band subassembly and a suture-permeable sewing ring joined together, and FIG. 11A is a radial sectional view through a cusp portion thereof;

FIGS. 12A and 12B are inflow and outflow perspective views, respectively, of a surgical heart valve before coupling with an inflow anchoring skirt to form the prosthetic heart valve of the present application;

FIG. 13 is an exploded assembly view of a portion of a cloth-covered anchoring skirt for coupling to the surgical heart valve;

FIG. 14 is an exploded assembly view of the portion of the cloth-covered anchoring skirt shown in FIG. 13 and a lower sealing flange secured thereto to form the inflow anchoring skirt;

FIG. 15A shows the surgical heart valve above the cloth-covered anchoring skirt and schematically shows one method of coupling the two elements, while FIG. 15B illustrates an inner plastically-expandable stent frame of the anchoring skirt and the pattern of coupling sutures passed therethrough;

FIGS. 16A-16J are perspective cutaway views of an aortic annulus showing a portion of the adjacent left ventricle below the ascending aorta, and illustrating a number of steps in deployment of an exemplary prosthetic heart valve disclosed herein, namely:

FIG. 16A shows a preliminary step in preparing an aortic annulus for receiving the heart valve including installation of guide sutures;

FIG. 16B shows the heart valve mounted on a distal section of a delivery handle advancing into position within the aortic annulus along the guide sutures;

FIG. 16C shows the heart valve in a desired implant position at the aortic annulus, and during placement of suture snares;

FIG. 16D shows forceps bending outward upper ends of the suture snares to improve access to the heart valve and implant site;

FIG. 16E shows a delivery system prior to advancement of a dilatation balloon;

FIG. 16F shows the delivery system after advancement of a dilatation balloon therefrom;

FIG. 16G shows the balloon of the balloon catheter inflated to expand the anchoring skirt;

FIG. 16H shows the balloon deflated and stretched;

FIG. 16I shows decoupling and removal of the balloon catheter from the valve holder after removal of the snares;

FIG. 16J shows the fully implanted prosthetic heart valve with the guide sutures knotted on the proximal face of a sewing ring;

FIG. 17 is a perspective view showing the exemplary prosthetic heart valve coupled to the valve holder along with components of a storage jar;

FIG. 18 is a perspective view of the heart valve and holder assembled to a storage clip that fits within the storage jar;

FIG. 18A is a bottom plan view of the valve holder mounted within the storage clip;

FIG. 20 is a perspective exploded view of the balloon introducer sleeve and handling rod;

FIGS. 21A-21E are various views showing details of the balloon introducer sleeve;

FIG. 22 is an exploded perspective view of components of a prosthetic heart valve delivery system of the present application;

FIG. 23 is an assembled perspective view of the prosthetic heart valve delivery system of FIG. 22;

FIGS. 25 and 25A are perspective and longitudinal sectional views of a locking sleeve of the exemplary heart valve delivery system;

FIGS. 26 and 26A-26B are perspective, end, and longitudinal sectional views of an adapter of the heart valve delivery system that couples to the heart valve holder;

FIG. 27 is a longitudinal sectional view taken along line 27-27 of FIG. 24C showing the manner in which the adapter and locking sleeve couple to the heart valve holder and balloon introducer sleeve;

FIGS. 30 and 30A are elevational and broken longitudinal sectional views, respectively, of the heart valve delivery system with a balloon catheter in a retracted position;

FIGS. 31 and 31A are elevational and broken longitudinal sectional views, respectively, of the heart valve delivery system with the balloon catheter in an extended position;

FIG. 32 is a perspective view of the proximal end of the exemplary heart valve delivery system of the present application showing a locking clip exploded therefrom, while

FIG. 38 is a partial sectional view of the heart valve delivery system having the prosthetic heart valve and valve holder thereon and in the balloon advanced configuration of FIG. 31A;

FIG. 39 is a partial sectional view similar to FIG. 38 and showing movement of a balloon extension wire to compress a spring upon balloon inflation;

FIG. 40 is similar to FIG. 38 and shows return movement of the balloon extension wire and spring upon balloon deflation;

FIGS. 49A-49D and 50A-50E schematically illustrate an alternative system including mechanical fingers for expanding the skirt stent of the prosthetic heart valve disclosed herein;

FIG. 55 is a perspective view of an exemplary prosthetic heart valve having a commercially available valve components coupled with a skirt stent minus a surrounding fabric cover, and FIG. 55A is a radial sectional view through a cusp portion of the heart valve with the fabric cover of the skirt stent shown;

FIG. 56 is an exploded elevational view of the prosthetic heart valve of FIG. 55;

DETAILED DESCRIPTION OF THE PREFERRED EMBODIMENTS

Figure 1:
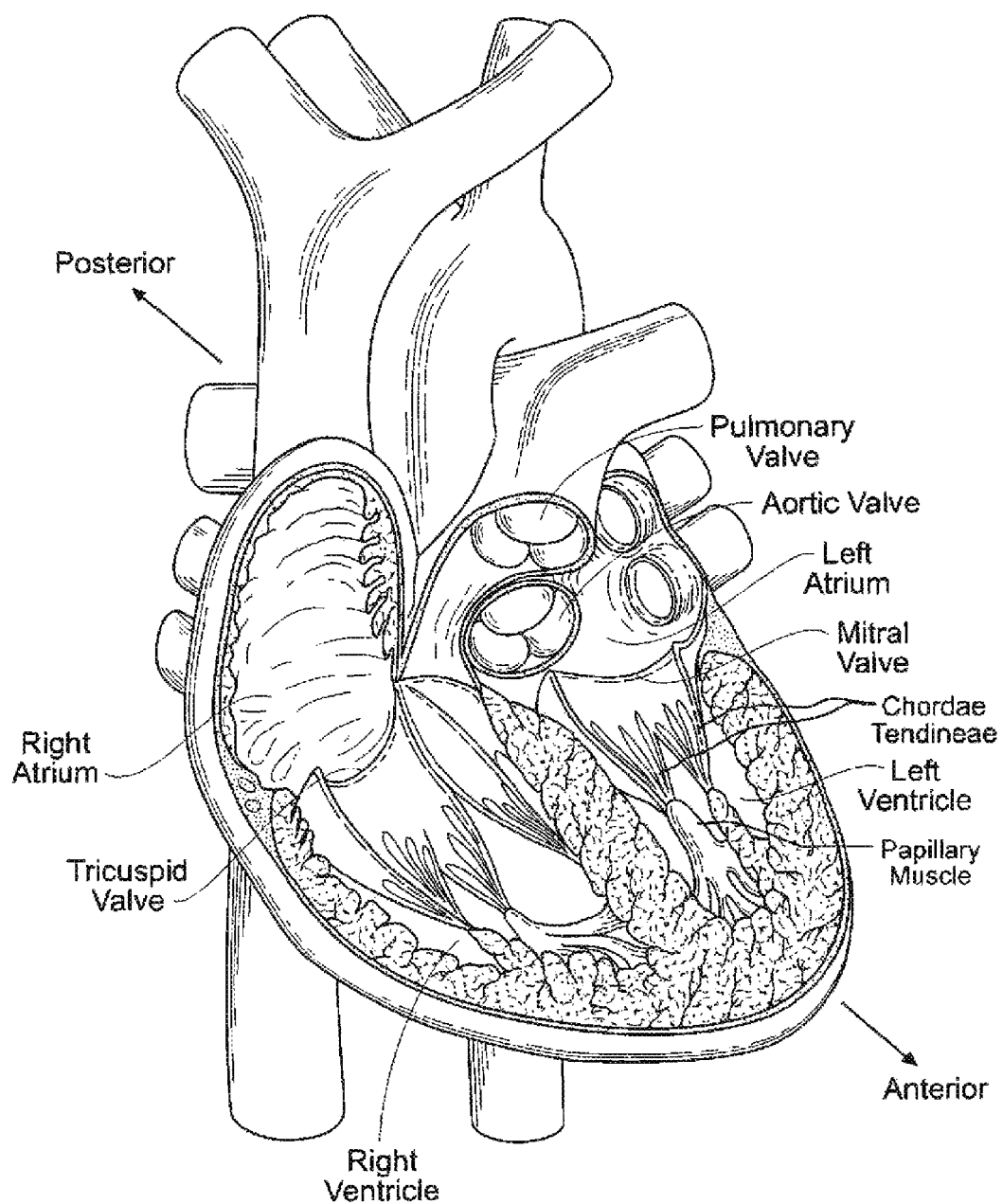
FIG. 1 is an anatomic anterior view of a human heart, with portions broken away and in section to view the interior heart chambers and adjacent structures.
Figure 2:
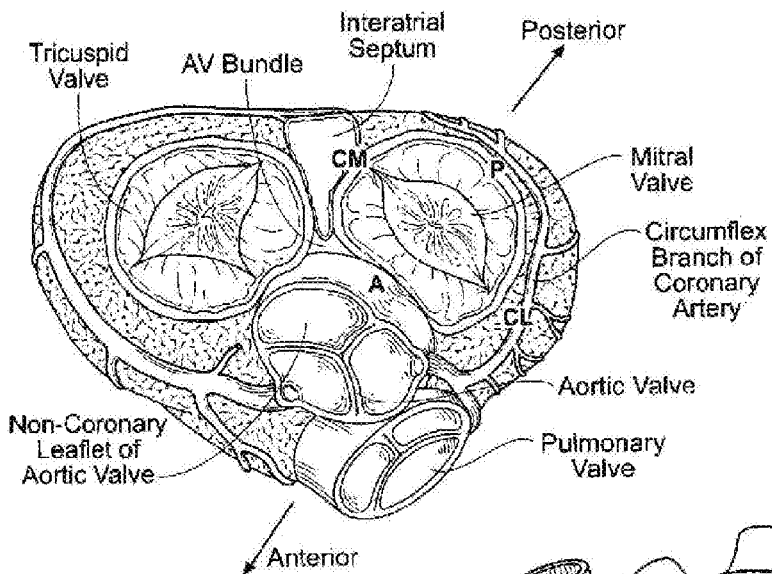
FIG. 2 is an anatomic superior view of a section of the human heart showing the tricuspid valve in the right atrium, the mitral valve in the left atrium, and the aortic valve in between, with the tricuspid and mitral valves open and the aortic and pulmonary valves closed during ventricular diastole (ventricular filling) of the cardiac cycle.
Figure 4:
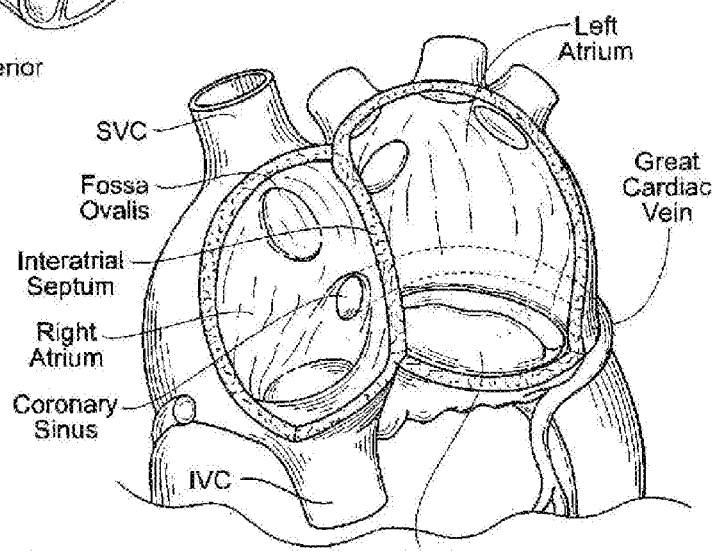
FIG. 4 is an anatomic anterior perspective view of the left and right atria, with portions broken away and in section to show the interior of the heart chambers and associated structures, such as the fossa ovalis, coronary sinus, and the great cardiac vein.
Figure 3:
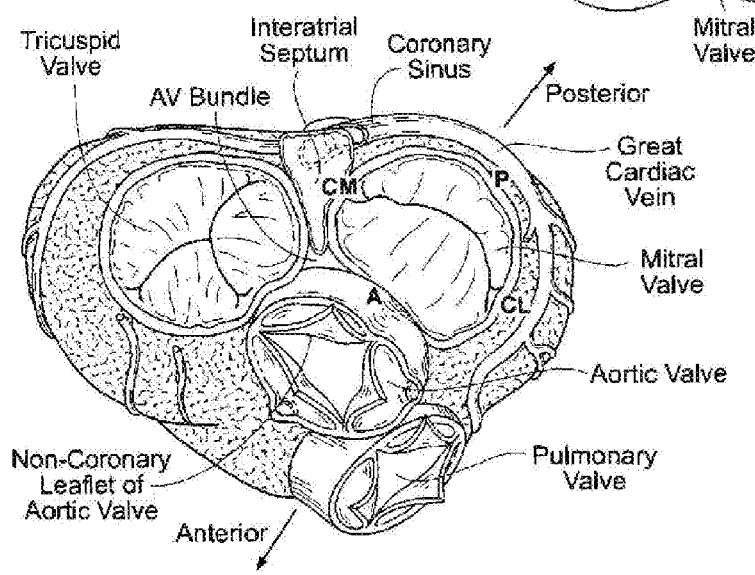
FIG. 3 is an anatomic superior view of a section of the human heart shown in FIG. 2, with the tricuspid and mitral valves closed and the aortic and pulmonary valves opened during ventricular systole (ventricular emptying) of the cardiac cycle.

The present invention attempts to overcome drawbacks associated with conventional, open-heart surgery, while also adopting some of the techniques of newer technologies which decrease the duration of the treatment procedure. The prosthetic heart valves of the present invention are primarily intended to be delivered and implanted using conventional surgical techniques, including the aforementioned open-heart surgery. There are a number of approaches in such surgeries, all of which result in the formation of a direct access pathway to the particular heart valve annulus. For clarification, a direct access pathway is one that permits direct (i.e., naked eye) visualization of the heart valve annulus. In addition, it will be recognized that embodiments of the prosthetic heart valves described herein may also be configured for delivery using percutaneous approaches, and those minimally-invasive surgical approaches that require remote implantation of the valve using indirect visualization. However, the latter two approaches—percutaneous and minimally-invasive—invariably rely on collapsible/expandable valve constructs. And, while certain aspects described herein could be useful for such valves and techniques, the primary focus and main advantages of the present application is in the realm of non-expandable "surgical" valves introduced in conventional manners.

One primary aspect of the present invention is a "unitary" prosthetic heart valve in which a tissue anchor is implanted at the same time as a valve member resulting in certain advantages. The exemplary unitary prosthetic heart valve of the present invention is a hybrid valve member, if you will, with both non-expandable and expandable portions. By utilizing an expandable anchoring skirt or stent coupled to a non-expandable valve member, the duration of the anchoring operation is greatly reduced as compared with a conventional sewing procedure utilizing an array of sutures. The expandable anchoring skirt may simply be radially expanded outward into contact with the implantation site, or may be provided with additional anchoring means, such as barbs. As stated, conventional open-heart approach and cardiopulmonary bypass familiar to cardiac surgeons are used. However, due to the expandable anchoring skirt, the time on bypass is greatly reduced by the relative speed of implant in contrast to the previous time-consuming knot-tying process.

For definitional purposes, the terms "stent" or "coupling stent" refer to a structural component that is capable of anchoring to tissue of a heart valve annulus. The coupling stents described herein are most typically tubular stents, or stents having varying shapes or diameters. A stent is normally formed of a biocompatible metal frame, such as stainless steel or Nitinol. More preferably, in the context of the present invention the stents are made from laser-cut tubing of a plastically-expandable metal. Other coupling stents that could be used with valves of the present invention include rigid rings, spirally-wound tubes, and other such tubes that fit tightly within a valve annulus and define an orifice therethrough for the passage of blood. It is entirely conceivable, however, that the coupling stent could be separate clamps or hooks that do not define a continuous periphery. Although such devices sacrifice some contact uniformity, and speed and ease of deployment, they could be configured to work in conjunction with a particular valve member.

A distinction between self-expanding and balloon-expanding stents exists in the field. A self-expanding stent may be crimped or otherwise compressed into a small tube and possesses sufficient elasticity to spring outward by itself when a restraint such as an outer sheath is removed. In contrast, a balloon-expanding stent is made of a material that is substantially less elastic, and indeed must be plastically expanded from the inside out when converting from a contracted to an expanded diameter. It should be understood that the term balloon-expanding stents encompasses plastically-expandable stents, whether or not a balloon is used to actually expand it (e.g., a device with mechanical fingers could expand the stent). The material of the stent plastically deforms after application of a deformation force such as an inflating balloon or expanding mechanical fingers. Consequently, the term "balloon-expandable stent" should be understood as referring to the material or type of the stent as opposed to the specific expansion means.

The term "valve member" refers to that component of a heart valve that possesses the fluid occluding surfaces to prevent blood flow in one direction while permitting it in another. As mentioned above, various constructions of valve members are available, including those with flexible leaflets and those with rigid leaflets, or even a ball and cage arrangement. The leaflets may be bioprosthetic, synthetic, metallic, or other suitable expedients. In a preferred embodiment, the non-expandable valve member is an "off-the-shelf" standard surgical valve of the type that has been successfully implanted using sutures for many years, such as the Carpentier-Edwards PERIMOUNT Magna® Aortic Heart Valve available from Edwards Lifesciences of Irvine, Calif., though the autonomous nature of the valve member is not absolutely required. In this sense, a "off-the-shelf" prosthetic heart valve is suitable for stand-alone sale and use, typically including a non-expandable, non-collapsible support structure having a sewing ring capable of being implanted using sutures through the sewing ring in an open-heart, surgical procedure.

A primary focus of the present invention is a prosthetic heart valve having a single stage implantation in which a surgeon secures a hybrid valve having an anchoring skirt and valve member to a valve annulus as one unit or piece (e.g., a "unitary" valve). Certain features of the hybrid anchoring skirt and valve member are described in co-pending U.S. Patent Publication No. 2010-0161036, filed Dec. 10, 2009, the contents of which are expressly incorporated herein. It should be noted that "two-stage" prosthetic valve delivery disclosed in the aforementioned publication refers to the two primary steps of a) anchoring structure to the annulus, and then b) connecting a valve member, which does not necessarily limit the valve to just two parts. Likewise, the valve described herein is especially beneficial in a single stage implant procedure, but that does not necessarily limit the overall system to just one part. For instance, the heart valve disclosed herein could also use an expanding base stent which is then reinforced by the subsequently implanted heart valve. Because the heart valve has a non-expandable and non-collapsible annular support structure, and a plastically-expandable anchoring skirt, it effectively resists recoil of a self-expanded base stent. That said, various claims appended hereto may exclude more than one part.

As a point of further definition, the term "expandable" is used herein to refer to a component of the heart valve capable of expanding from a first, delivery diameter to a second, implantation diameter. An expandable structure, therefore, does not mean one that might undergo slight expansion from a rise in temperature, or other such incidental cause such as fluid dynamics acting on leaflets or commissures. Conversely, "non-expandable" should not be interpreted to mean completely rigid or a dimensionally stable, as some slight expansion of conventional "non-expandable" heart valves, for example, may be observed.

In the description that follows, the term "body channel" is used to define a blood conduit or vessel within the body. Of course, the particular application of the prosthetic heart valve determines the body channel at issue. An aortic valve replacement, for example, would be implanted in, or adjacent to, the aortic annulus. Likewise, a mitral valve replacement will be implanted at the mitral annulus. Certain features of the present invention are particularly advantageous for one implantation site or the other, in particular the aortic annulus. However, unless the combination is structurally impossible, or excluded by claim language, any of the heart valve embodiments described herein could be implanted in any body channel.

A "quick-connect" aortic valve bio-prosthesis described herein is a surgically-implanted medical device for the treatment of aortic valve stenosis. The exemplary quick-connect device comprises an implantable bio-prosthesis and a delivery system for its deployment. The device, delivery system and method of use take advantage of the proven hemodynamic performance and durability of existing commercially available, non-expandable prosthetic heart valves, while improving ease of use and reducing total procedure time. This is mainly accomplished by eliminating the need to suture the bio-prosthesis onto the native annulus as is currently done per standard surgical practice, and typically requires 12-24 manually-tied sutures around the valve perimeter. Also, the technique may obviate the need to excise the leaflets of the calcified valve and debride or smooth the valve annulus.

Figure 5A:
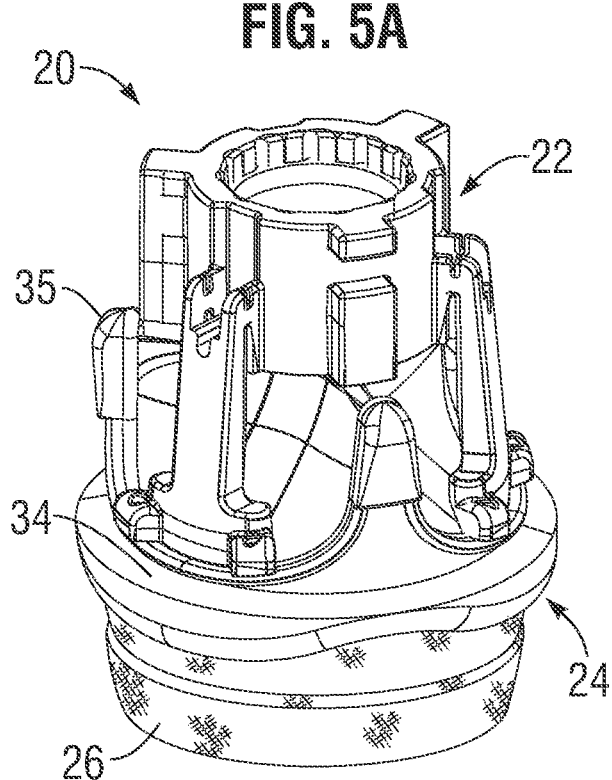
FIGS. 5A and 5B are perspective views of an exemplary prosthetic heart valve of the present application assembled on a valve holder.
Figure 5B:
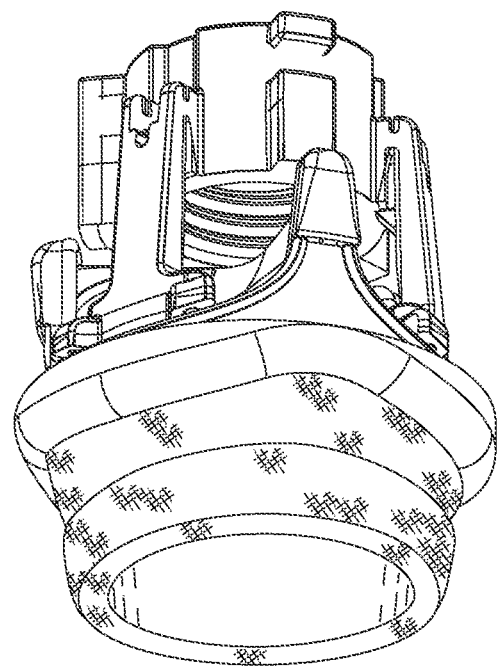
Figure 6A:
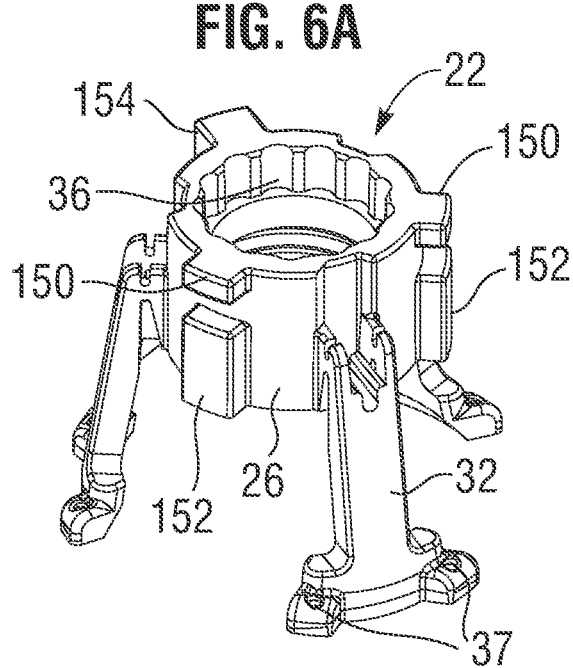
FIGS. 6A and 6B are perspective view of the valve holder of FIGS. 5A and 5B separated from the heart valve.
Figure 6B:
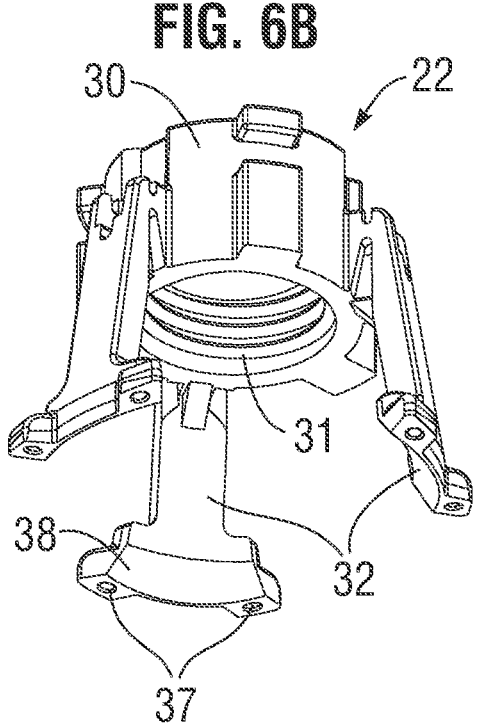

FIGS. 5A and 5B show an exemplary hybrid prosthetic heart valve 20 of the present application assembled on a valve holder 22, while FIGS. 6A and 6B show the valve holder 22 separated from the heart valve 20. As mentioned, the prosthetic heart valve 20 desirably includes a valve member 24 having an anchoring skirt 26 attached to an inflow end thereof. The valve member 24 is desirably non-collapsible and non-expandable, while the anchoring skirt 26 may expand from the contracted state shown into an expanded state, as will be described. In one embodiment, the valve member 24 comprises a Carpentier-Edwards PERIMOUNT Magna® Aortic Heart Valve available from Edwards Lifesciences of Irvine, Calif., while the anchoring skirt 26 includes an inner plastically-expandable frame or stent covered with fabric.

The valve holder 22, as seen in the details of FIGS. 6A and 6B, and also in FIGS. 7A-7D and 8A-8C, includes a central tubular hub portion 30 having internal threads 31, and a plurality of stabilizing legs 32 projecting axially and radially outward therefrom. Each of the three stabilizing legs 32 contacts and attaches to a cusp portion 34 of the valve member 24 between commissure posts 35 (see FIG. 5A). An upper end of the hub portion 30 also has an internal star-shaped bore 36 that provides a valve-size-specific keyed engagement with a delivery system, as will be explained. Details of both the valve holder 22 and valve member 24, and their interaction, will be provided below. Suffice it to say at this point, that the valve holder 22 secures with sutures to the valve member 24 from the time of manufacture to the time of implant, and is stored with the valve member.

Figure 8B:
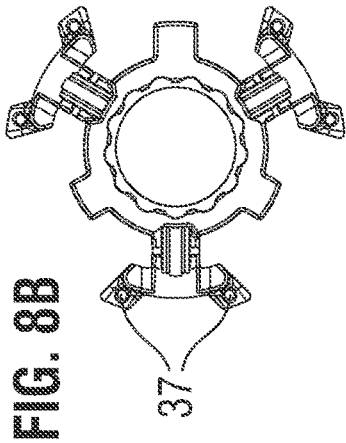
FIGS. 8A-8C are elevational, plan, and sectional views of the exemplary valve holder.
Figure 8A:
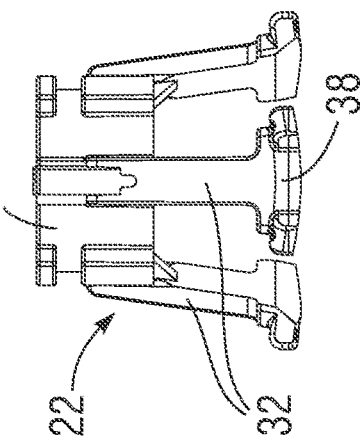
Figure 8C:
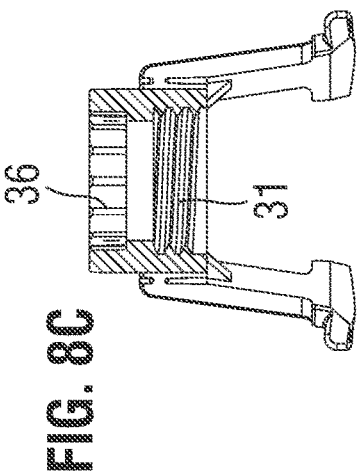
Figure 7B:
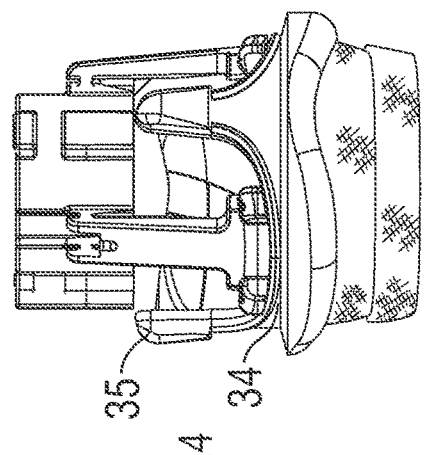
FIGS. 7A-7D are orthogonal views of the exemplary prosthetic heart valve and valve holder.
Figure 7C:
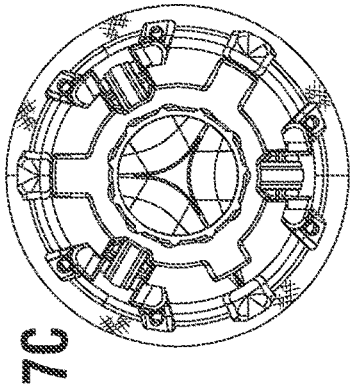
Figure 7A:
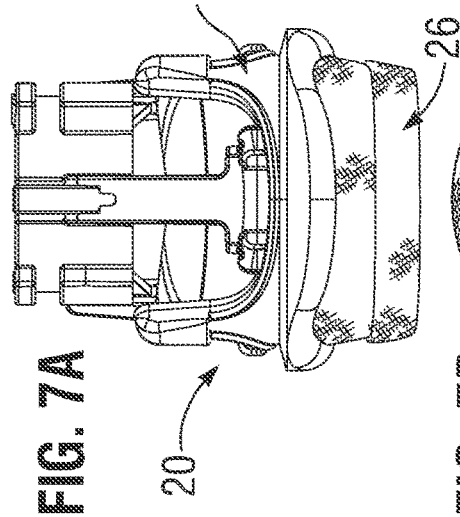
Figure 7D:
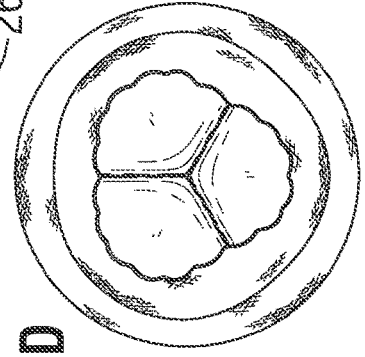

In one embodiment, the holder 22 is formed of a rigid polymer such as Delrin polypropylene that is transparent to increase visibility of an implant procedure. As best seen in FIG. 8B, the holder 22 exhibits openings between the stabilizing legs 32 to provide a surgeon good visibility of the valve leaflets, and the transparency of the legs further facilitates visibility and permits transmission of light therethrough to minimize shadows.

FIGS. 7-8 also illustrate a series of through holes 37 in the legs 32 permitting connecting sutures to be passed through fabric at the cusps 34 of the prosthetic valve member 24 and across a cutting guide in each leg. As is known in the art, severing a middle length of a suture that is connected to the holder 22 and passes through the valve permits the holder to be pulled free from the valve when desired. Each leg 32 extends radially outward and downward from the portion 30 in a substantially constant thickness until a distal foot 38 which is substantially wider. The distal foot 38 may be twice as wide as the upper portion of the respective leg 32. The through holes 37 pass through circumferentially outer points of each distal foot 38, and are thus spaced significantly apart for each leg 32. This provides six total attachment points between the holder 22 and the valve member 24, all in the cusp regions 34. Moreover, each leg 32 extends down to the center or nadir of each cusp portion 34, which allows the surgeon better access behind and adjacent to the commissure posts. Furthermore, the spread out nature of the feet 38 and dual attachment points thereon provides an extremely robust holding force between the holder and bow. The configuration of the wide feet 38 and through holes 37 thereon forms an inverted Y-shape of sorts. Prior holders either attached to the top of the commissure posts, or to a single point in the nadir of each cusp. Such holders left the valve prone to twisting or deforming from contact with operating room or anatomical surfaces.

FIGS. 9-15 illustrate a number of steps in the construction of the prosthetic heart valve 20.

FIG. 9 illustrates an inner structural band subassembly 40 including an inner polymer band 42 having three upstanding posts 44 and a scalloped lower ring 46, and an outer more rigid band 48 having a scalloped shape to conform to the lower ring 46. The band subassembly 40 is formed by positioning the polymer band 42 within the rigid band 48 and securing them together with sutures through aligned holes, for example.

FIG. 10 is a perspective view of a further subassembly of an undulating cloth-covered wireform 50. FIG. 10A is a detailed sectional view of a cusp portion of the wireform 50 showing an inner wire member 52 covered with fabric that defines a tubular portion 54 and an outwardly projecting flap 56. The wireform 50 defines three upstanding commissure posts 58 and three downwardly convex cusps 60. This is a standard shape for tri-leaflet heart valves and mimics the peripheral edges of the three native aortic leaflets. The shape of the wireform 50 coincides with the upper edge of the band subassembly 40, and defines the outflow edge of the prosthetic valve 20. The band subassembly 40 and wireform 50 are then joined together with a cloth interface and outer sewing ring, and then with flexible leaflets as will be shown.

FIG. 11 is a perspective view of the assembled band subassembly 40 and sewing ring 62, while FIG. 11A shows details through a cusp portion thereof. The two structural bands 42, 48 are the same heights in the cusp region and encompassed by a fabric cover 64 that is rolled into a peripheral tab 66. The sewing ring 62 comprises an inner suture permeable member 68 having a frustoconical form and encompassed by a second fabric cover 70. The two fabric covers 64, 70 are sewn together at a lower junction point 72.

FIGS. 12A and 12B are inflow and outflow perspective views, respectively, of the surgical heart valve member 24 before coupling with an inflow anchoring skirt to form the prosthetic heart valve 20. Although construction details are not shown, three flexible leaflets 74 are secured along the undulating wireform 50 and then to the combination of the band subassembly 40 and sewing ring 62 shown in FIG. 11. In a preferred embodiment, each of the three leaflets includes outwardly projecting tabs that pass through the inverted U-shaped commissure posts 58 and wrap around the cloth-covered commissure posts 75 (see FIG. 11) of the band subassembly 40. The entire structure at the commissures is covered with a secondary fabric to form the valve commissures 35 as seen in FIG. 15A.

As stated previously, the completed valve member 24 shown in FIGS. 12A and 12B provides the occluding surfaces for the prosthetic heart valve 20 described herein. Although an autonomous (i.e., capable of stand-alone surgical implant) flexible leaflet valve member 24 is described and illustrated, alternative valve members that have rigid leaflets, or are not fully autonomous may be substituted. In various preferred embodiments, the valve leaflets may be taken from another human heart (cadaver), a cow (bovine), a pig (porcine valve) or a horse (equine). In other preferred variations, the valve member may comprise mechanical components rather than biological tissue.

One feature of the valve member 24 that is considered particularly important is the sewing ring 62 that surrounds the inflow end thereof. As will be seen, the sewing ring 62 is used to attach the anchoring skirt 26 to the valve member 24. Moreover, the sewing ring 62 presents an outward flange that contacts and outflow side of the part of annulus, while the anchoring skirt 26 expands and contracts the opposite, ventricular side of the annulus, therefore securing the heart valve 20 to the annulus from both sides. Furthermore, the presence of the sewing ring 62 provides an opportunity for the surgeon to use conventional sutures to secure the heart valve 20 to the annulus as a contingency.

The preferred sewing ring 62 defines a relatively planar upper or outflow face and an undulating lower face. Cusps of the valve structure abut the sewing ring upper face opposite locations where the lower face defines peaks. Conversely, the valve commissure posts align with locations where the sewing ring lower face defines troughs. The undulating shape of the lower face advantageously matches the anatomical contours of the aortic side of the annulus AA, that is, the supra-annular shelf. The ring 62 preferably comprises a suture-permeable material such as rolled synthetic fabric or a silicone inner core covered by a synthetic fabric. In the latter case, the silicone may be molded to define the contour of the lower face and the fabric cover conforms thereover.

Now with reference to FIGS. 13 and 14, assembly of the cloth-covered anchoring skirt 26 will be described. It should first be noted that the size of the anchoring skirt 26 will vary depending on the overall size of the heart valve 20. Therefore the following discussion applies to all sizes of valve components, with the dimensions scaled accordingly.

The general function of the anchoring skirt 26 is to provide the means to attach the prosthetic valve member 24 to the native aortic root. This attachment method is intended as an alternative to the present standard surgical method of suturing aortic valve bio-prostheses to the aortic valve annulus, and is accomplished in much less time. Further, this attachment method improves ease of use by eliminating most of not all suturing. The anchoring skirt 26 may be a pre-crimped, tapered, 316L stainless steel balloon-expandable stent, desirably covered by a polyester fabric to help seal against paravalvular leakage and promote tissue ingrowth once implanted within the annulus. The anchoring skirt 26 transitions between the tapered constricted shape of FIGS. 5A-5B to its flared expanded shape shown in FIG. 16J below.

The anchoring skirt 26 comprises an inner stent frame 80, a fabric covering 82, and a band-like lower sealing flange 84. The inner stent frame 80 will be described in greater detail below, but preferably comprises a tubular plastically-expandable member having an undulating or scalloped upper end 86. The stent frame 80 assembles within a tubular section of fabric 82 which is then drawn taut around the stent frame, inside and out, and sewn thereto to form the intermediate cloth-covered frame 88 in FIG. 13. During this assembly process, the stent frame 80 is desirably tubular, though later the frame will be crimped to a conical shape as see in FIG. 15B for example. A particular sequence for attaching the tubular section of fabric 82 around the stent frame 80 includes providing longitudinal suture markers (not shown) at 120° locations around the fabric to enable registration with similarly circumferentially-spaced, commissure features on the stent frame. After surrounding the stent frame 80 with the fabric 82, a series of longitudinal sutures at each of the three 120° locations secure the two components together. Furthermore, a series of stitches are provided along the undulating upper end 86 of the stent frame 80 to complete the fabric enclosure. In one embodiment, the tubular section of fabric 82 comprises PTFE cloth, although other biocompatible fabrics may be used.

Subsequently, the lower sealing flange 84 shown in FIG. 14 is attached circumferentially around a lower edge of the intermediate cloth-covered frame 88. First, a linear band 90 of a single layer of fabric, preferably knitted, is formed into a ring and its ends sutured together using a butt joint (not shown). The ring is placed around the intermediate cloth-covered frame 88, aligned with a lower edge thereof, and sewn thereto. Preferably, a series of stitches are formed at and adjacent to the commissure markers previously described. Alternatively, two circumferential lines of stitches may be provided around the lower sealing flange 84 to provide greater anchoring.

The material of the lower sealing flange 84 may vary, but preferably provides a compressible flange about the lower edge of the anchoring skirt 26. For example, the lower sealing flange 84 may be a knitted PTFE fabric in a single layer or multiple layers, Teflon, a silicone ring covered by fabric, or other similar expedients. Furthermore, the sealing flange 84 may not comprise fabric at all, but may be a hydrophilic coating, fibrin glue, or other such substance that helps prevent leakage around the outside of the anchoring skirt 26. The main functions of the fabric layers covering the frame 88 are to help prevent paravalvular leaks and provide means to securely encapsulate any Calcium nodules on the aortic valve leaflets (if left in place) and/or the aortic valve annulus. Covering the entire anchoring skirt 26 eliminates exposed metal and decreases the risk of thromboembolic events and abrasion. In a preferred embodiment, the sealing flange 84 has an axial dimension of between about 2-5 mm, and is spaced from the upper end 86 of the frame 80 by a distance that varies between 2-5 mm. The lower end of the frame may also be scalloped to follow the upper end 86, in which case the sealing flange 84 may also undulate to maintain an even distance with the upper end 86. If a knitted PTFE fabric, the sealing flange 84 desirably has a radial thickness of at least twice the thickness of the tubular fabric 82.

FIG. 15A shows the surgical heart valve member 24 above the cloth-covered anchoring skirt 26 and one way to couple the two elements using sutures. FIG. 15B illustrates the inner stent frame 80 with cloth covering removed to indicate a preferred pattern of coupling sutures passed therethrough.

The anchoring skirt 26 preferably attaches to the sewing ring 62 during the manufacturing process in a way that preserves the integrity of the ring and prevents reduction of the valve's effective orifice area (EOA). Desirably, the anchoring skirt 26 will be continuously sutured to the ring 62 in a manner that maintains the contours of the ring. In this regard, sutures may be passed through apertures or eyelets 92 arrayed along the upper or first end 86 of the inner stent frame 80. Other connection solutions include prongs or hooks extending inward from the stent, ties, Velcro, snaps, adhesives, etc. Alternatively, the anchoring skirt 26 may be more rigidly connected to rigid components within the prosthetic valve member 24.

The inner stent frame 80 is seen in greater detail in FIGS. 13 and 15B. The inner stent frame 80 may be similar to an expandable Stainless Steel stent used in the Edwards SAPIEN Transcatheter Heart Valve. However, the material is not limited to Stainless Steel, and other materials such as Co—Cr alloys, etc. may be used. Ultimately, the inner stent frame 80 assumes a crimped, tapered configuration that facilitates insertion through the calcified native aortic valve (see FIG. 7A). In the tapered configuration, a lower edge 94 of the frame 80 describes a circle having a smaller diameter than a circle described by the upper end 86. The upper end 86 follows an undulating path with alternating arcuate troughs and pointed peaks that generally corresponds to the undulating contour of the underside of the sewing ring 62 (see FIG. 5B). The mid-section of the frame 80 has three rows of expandable struts 98 in a sawtooth pattern between axially-extending struts 100. The axially-extending struts 100 are out-of-phase with the peaks and troughs of the upper end 86 of the stent. The reinforcing ring defined by the thicker wire upper end 86 is continuous around its periphery and has a substantially constant thickness or wire diameter interrupted by the aforementioned eyelets 92. Note that the attachment sutures ensure that the peaks of the upper end 86 of the skirt 26 fit closely to the troughs of the sewing ring 62, which are located under the commissures of the valve.

The minimum I.D. of the upper end 86 of the covered skirt 26 will always be bigger than the I.D. of the prosthetic valve member 24 to which it attaches. For instance, if the upper end 86 secures to the underside of the sewing ring 62, which surrounds the support structure of the valve, it will by definition be larger than the I.D. of the support structure (which defines the valve orifice and corresponding labeled valve size).

An exemplary implant procedure for the prosthetic heart valve 20 will now be described with reference to FIGS. 16A-16J, which are sectional views through an isolated aortic annulus AA showing a portion of the adjacent left ventricle LV and ascending aorta AO with sinus cavities. The two coronary arteries CA are also shown. As will be explained, the anchoring skirt 26 is deployed against the native leaflets or, if the leaflets are excised, against the debrided aortic annulus AA as shown.

In the ensuing procedure drawings, the heart valve 20 is oriented with an inflow end down and an outflow end up. Therefore, the terms inflow and down may be used interchangeably at times, as well as the terms outflow and up. Furthermore, the terms proximal and distal are defined from the perspective of the surgeon delivering the valve inflow end first, and thus proximal is synonymous with up or outflow, and distal with down or inflow.

An implant procedure involves delivering the heart valve 20 and expanding the anchoring skirt 26 at the aortic annulus. Because the valve member 24 is non-expandable, the entire procedure is typically done using the conventional open-heart technique. However, because the anchoring skirt 26 is implanted by simple expansion, with reduced suturing, the entire operation takes less time. This hybrid approach will also be much more comfortable to surgeons familiar with the open-heart procedures and commercially available heart valves.

Moreover, the relatively small change in procedure coupled with the use of proven heart valves should create a much easier regulatory path than strictly expandable, remote procedures. Even if the system must be validated through clinical testing to satisfy the Pre-Market Approval (PMA) process with the FDA (as opposed to a 510 k submission), at least the surgeon acceptance of the quick-connect heart valve 20 will be greatly streamlined with a commercial heart valve that is already proven, such as the Magna® Aortic Heart Valve.

FIG. 16A shows a preliminary step in preparing an aortic annulus AA for receiving the heart valve 20, including installation of guide sutures 102. The aortic annulus AA is shown schematically isolated and it should be understood that various anatomical structures are not shown for clarity. The annulus AA includes a fibrous ring of tissue that projects inward from surrounding heart walls. The annulus AA defines an orifice between the ascending aorta AO and the left ventricle LV. Although not shown, native leaflets project inward at the annulus AA to form a one-way valve at the orifice. The leaflets may be removed prior to the procedure, or left in place as mentioned above. If the leaflets are removed, some of the calcified annulus may also be removed, such as with a rongeur. The ascending aorta AO commences at the annulus AA with three outward bulges or sinuses, two of which are centered at coronary ostia (openings) CO leading to coronary arteries CA. As will be seen below, it is important to orient the prosthetic valve member 24 so that its commissure posts are not aligned with and thus not blocking the coronary ostia CO.

The surgeon attaches the guide sutures 102 at three evenly spaced locations around the aortic annulus AA. In the illustrated embodiment, the guide sutures 102 attach to locations below or corresponding to the coronary ostia CO (that is, two guide sutures are aligned with the ostia, and the third centered below the non-coronary sinus). The guide sutures 102 are shown looped twice through the annulus AA from the outflow or ascending aorta side to the inflow or ventricular side. Of course, other suturing methods or pledgets may be used depending on surgeon preference.

FIG. 16B shows the guide sutures 102 having been secured so that each extends in pairs of free lengths from the annulus AA and out of the operating site. The heart valve 20 mounts on a distal section of a delivery system 110 and the surgeon advances the valve into position within the aortic annulus AA along the guide sutures 102. That is, the surgeon threads the three pairs of guide sutures 102 through evenly spaced locations around the sewing ring 62. If the guide sutures 102, as illustrated, anchor to the annulus AA below the aortic sinuses, they thread through the ring 62 mid-way between the valve commissure posts. Thus, the guide sutures 102 pass through the sewing ring 62 at the cusps of the valve and are less likely to become tangled with the valve commissure posts. Furthermore, the exemplary ring 62 has an undulating inflow side such that the cusp locations are axially thicker than the commissure locations, which provides more material for securing the guide sutures 102.

FIG. 16C shows the heart valve in a desired implant position at the aortic annulus AA, and during placement of tubular suture snares. The sewing ring 62 is positioned supra-annularly, or above the narrowest point of the aortic annulus AA, so as to allow selection of a larger orifice size than a valve placed intra-annularly. Furthermore, with annulus expansion using the anchoring skirt 26, and the supra-annular placement, the surgeon may select a valve having a size one or two increments larger than previously conceivable. A dilatation balloon 112 on the delivery system 110 can be seen just beyond the distal end of the anchoring skirt 26.

The surgeon delivers a plurality of suture snares 120 down each free length of the guide sutures 102 into contact with the upper or outflow side of the sewing ring 62. The snares 120 enable downward pressure to be applied to the ring 62 and thus the valve 20 during the implant procedure, which helps insure good seating of the ring 62 on the annulus AA. The snares 120 also provide rigid enclosures around each of the flexible guide sutures 102 which helps avoid entanglement with other moving surgical instruments, as will be appreciated. As there are three pairs of guide sutures 102 (six free lengths) three snares 120 are utilized, though more or less is possible. The snares 120 are typically tubular straw-like members of medical grade plastic.

FIG. 16D shows forceps 122 clamping upper ends of the suture snares 120, and bending one pair outward to improve access to the heart valve 20 and implant site.

Figure 16E:
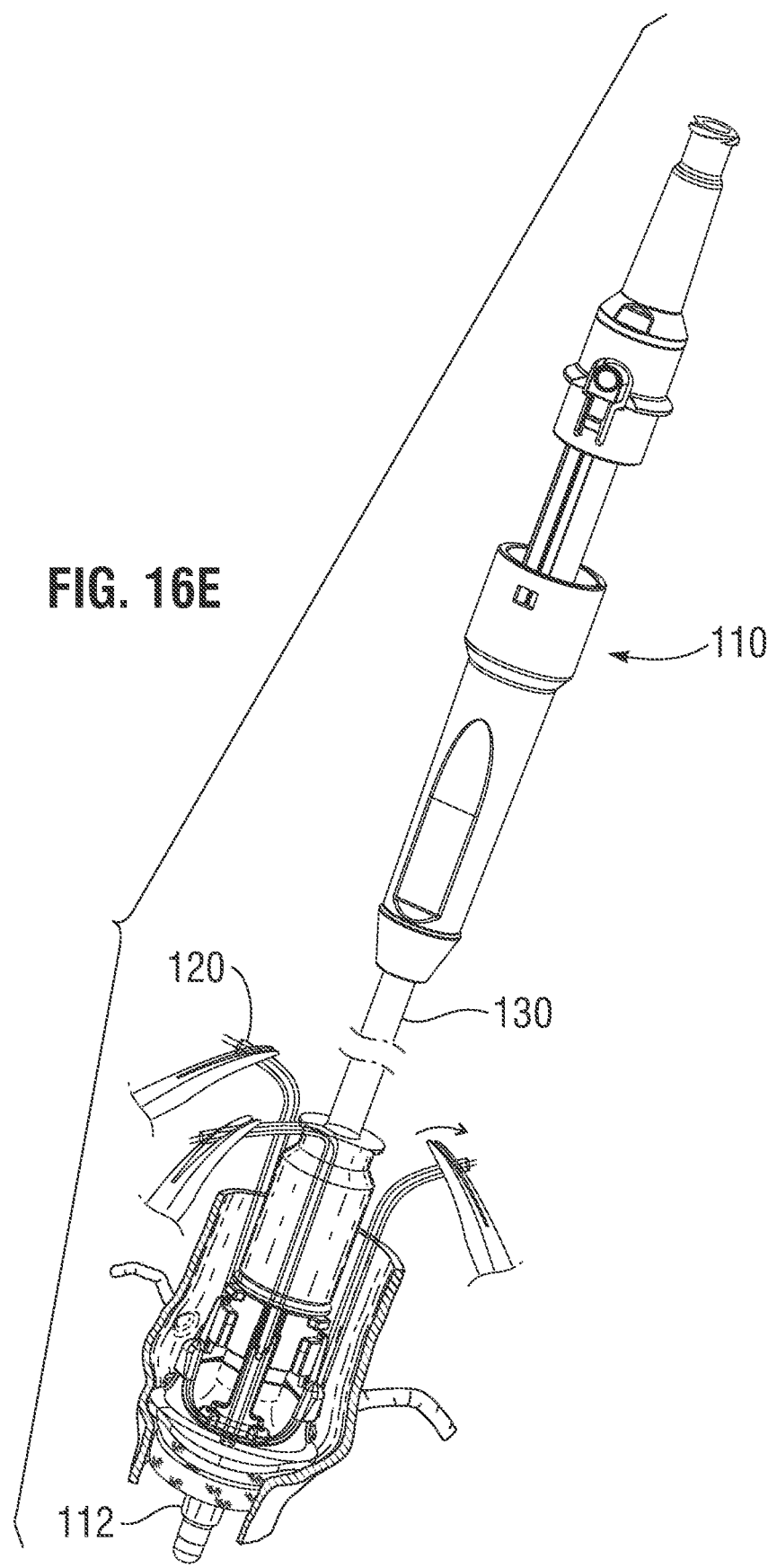

FIG. 16E shows all of the pairs of suture snares 120 bent outward and a majority of the delivery system 110. Although it will be described in greater detail below, the delivery system 110 includes a malleable handle shaft 130 for manipulating the heart valve 20 on the holder 22. The delivery system 110 is in a configuration prior to advancement of the dilatation balloon 112.

Figure 16F:
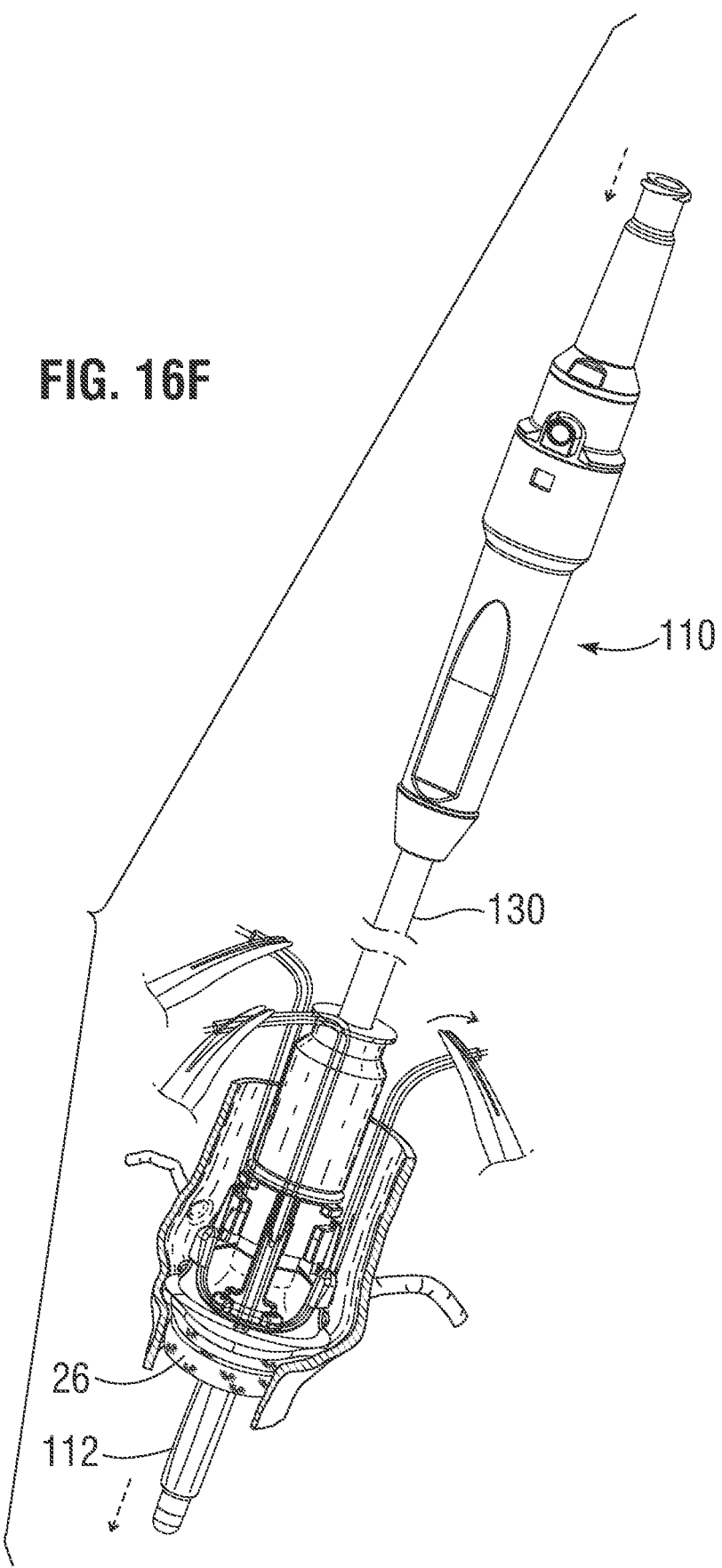

FIG. 16F shows the delivery system after advancement of the dilatation balloon 112. The balloon 112 projects downward through the valve 20, and into the left ventricle. As will be explained below, the delivery system 110 provides binary position displacement of the balloon 112, either retracted substantially within the handle shaft 130 or advanced precisely as far as necessary to expand the anchoring skirt 26 of the prosthetic heart valve 20.

FIG. 16G shows the dilatation balloon 112 inflated to expand the anchoring skirt 26 against the ventricular side of the aortic annulus. The balloon 112 desirably has a frusto-conical profile that expands the anchoring skirt 26 into a frustoconical expanded state. Not only does this conform better to the subannular contours but over expands somewhat the annulus that a larger valve maybe utilized then without the expansion. One advantage of using a plastically-expandable stent is the ability to expand the native annulus to receive a larger valve size than would otherwise be possible with conventional surgery. Desirably, the left ventricular outflow tract (LVOT) is significantly expanded by at least 10%, or for example by 1-5 mm, and the surgeon can select a heart valve 20 with a larger orifice diameter relative to an unexpanded annulus. Even a 1 mm increase in annulus size is significant since the gradient is considered to be proportional to the radius raised to the 4th power.

The balloon 112 desirably is tapered to have an angle between about 0-45°, and more preferably is about 38° (0° being a cylindrical expansion). Alternatively, the balloon 112 may include curves or non-axe-symmetric contours to deform the anchoring skirt 26 to various desired shapes to fit better within the particular annulus. Indeed, various potential shapes are described in U.S. Patent Publication 2008-0021546, entitled System for Deploying Balloon-Expandable Heart Valves, published Jan. 24, 2008, the disclosure of which is expressly incorporated herein.

FIG. 16H then illustrates the balloon 112 deflated and rewrapped. A spring mechanism within the delivery system 110 along with longitudinal pleats in the balloon 112 facilitate rewrapping of the balloon when deflated into an extremely narrow configuration which makes removal easier.

Figure 16I:
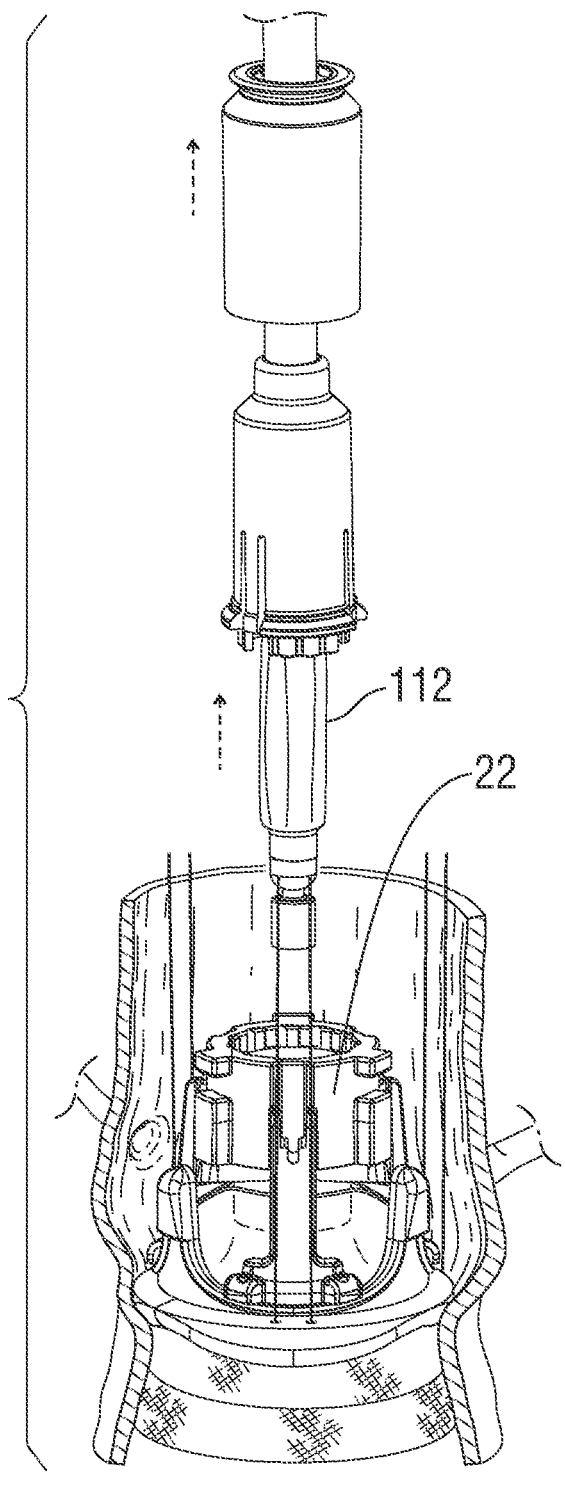

FIG. 16I shows retraction of the balloon 112 and entire delivery system 110 from the valve holder 22 before or after removal of the snares 120, which happens only as a contingency. Although not shown, the most common procedure after expansion of the balloon and skirt 26 involves the surgeon severing the connecting sutures between the valve holder 22 and the prosthetic valve member 24, and removing the entire delivery system. Severing a middle length of each suture that connects the holder 22 to the valve member 24 permits the delivery system 110 with the holder at the distal end to be pulled free from the valve 20. However, the delivery system 110 also features a simple engagement and detachment mechanism explained below that enables the surgeon to easily remove the system 110 from the holder 22 which remains attached to the valve 20, as seen in FIG. 16I. This detachment may be needed to replace the balloon catheter, such as if the original balloon develops a leak or for some reason does not deploy properly. This "quick-release" arrangement permits the surgeon to rapidly exchange catheters while leaving the valve 20 in place.

Figure 16J:
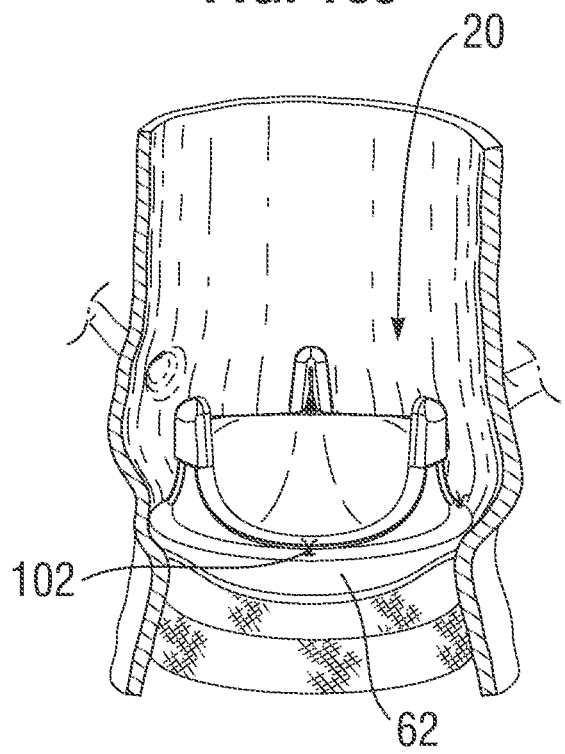

Finally, FIG. 16J shows the fully implanted prosthetic heart valve 20 with the guide sutures 102 knotted on the proximal face of a sewing ring 62. The guide sutures 102 are primarily for rotationally orienting the heart valve 20 as it seats against the aortic annulus and to define a plane for axial positioning. As such, the guide sutures 102 are not believed strictly necessary for securing the heart valve 20 at the annulus. Moreover, although knots are shown for securing the guide sutures 102, other devices such as clips or cinches could be used to speed up the process Placement of the guide sutures 102 at the cusps of the native valve and prosthesis separates the knots from the commissures, thus increasing accessibility. Also, the number of knots are reduced to three between the commissure posts, rather than multiple knots (12-24) as before, some of which were behind the commissure posts. The use of three sutures correctly positions the valve 20 and centering the sutures between the commissure posts is the most accessible for tying knots because the cusps are the lowest points in the annulus. Placement of knots (or clips) at the lowest point in the annulus also helps minimize the risk of coronary occlusion.

FIG. 17 illustrates an exemplary arrangement of components for storing the prosthetic heart valve 20 after manufacture and prior to use. This "wet" storage arrangement applies to the illustrated heart valve 20 shown, which includes conventional bioprosthetic leaflets, but could also be used for bioprosthetic leaflets that have been dried and also for mechanical valves.

The heart valve 20 is shown attached to the aforementioned holder 22 and above a storage clip 140 that fits within a storage jar 142 having a lid 144. FIG. 18 illustrates the heart valve 20 and holder 22 mounted to the storage clip 140. The inflow end of the heart valve 20, and in particular the expandable anchoring skirt 26, faces upward in this mounting arrangements. This orientation enables a technician to insert a handling rod and leaflet parting sleeve described below through the center of the heart valve 20 from the inflow to the outflow side. Typically, prosthetic aortic valves are stored with the outflow side and commissures pointed upward so that a handle may be attached to an upstanding holder, as this is the standard delivery orientation.

If the prosthetic heart valve 20 has conventional bioprosthetic leaflets, they require a liquid preservative for long-term storage. Therefore, a preservative such as glutaraldehyde is provided within the jar 142.

FIG. 18A is a bottom view of the valve holder 22 mounted within the storage clip 140 which illustrates, along with FIG. 18, structure that indicates to an assembler that the two components are not properly engaged. More particularly, with reference back to FIG. 6A, the central tubular hub portion 30 of the holder 22 features a plurality of outwardly projecting tabs or lugs on three evenly-spaced sides for engaging the storage clip 140. On two of the sides, as shown, these include a small lug 150 on the outflow end of the holder spaced from a longer lug 152 across a gap. On the third side, as best seen in FIG. 18, a single elongated lug 154 extends the length of the central hub portion 30. The gaps between the lugs 150, 152 receive the inner edges of a central aperture of the storage clip 140, while the elongated lug 154 extends out through a lateral exit slot 156. Because the elongated lug 154 is uninterrupted, if an assembler inserts the holder 22 into the central aperture of the storage clip 140 in other than the orientation shown, the lug 154 will wedge apart the two semi-circular side of the storage clip 140 and prevent the clip from fitting within the storage jar 142.

Figure 19A:
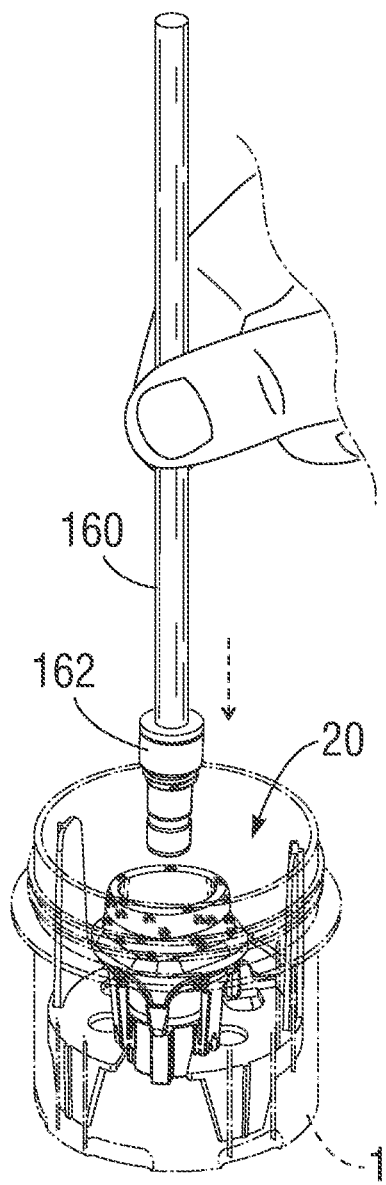
FIG. 19A is a perspective view showing a balloon introducer sleeve on the end of a handling rod being inserted through an inflow end of the prosthetic heart valve mounted in the storage clip within the storage jar (in phantom)
Figure 19B:
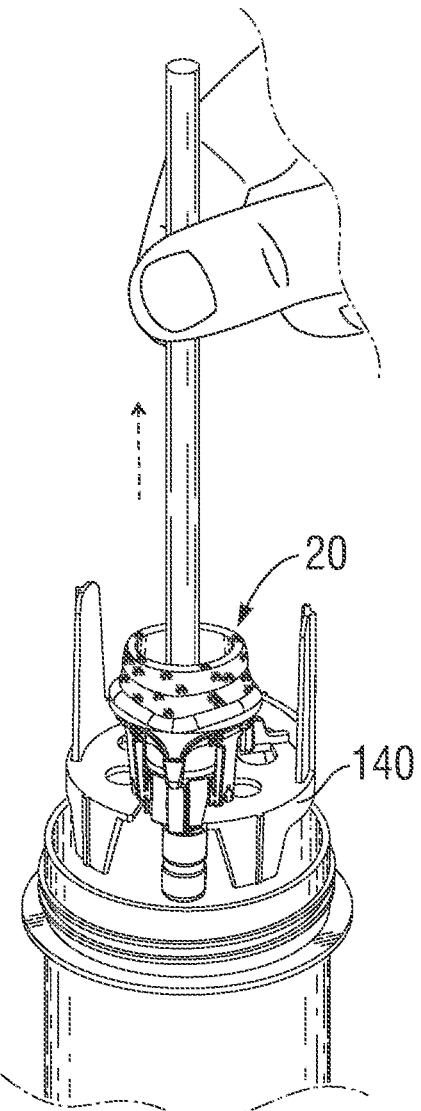
FIG. 19B shows the assembly of the heart valve/holder and storage clip being removed from the storage jar using the handling rod after coupling the balloon introducer sleeve to the valve holder.
Figure 19C:
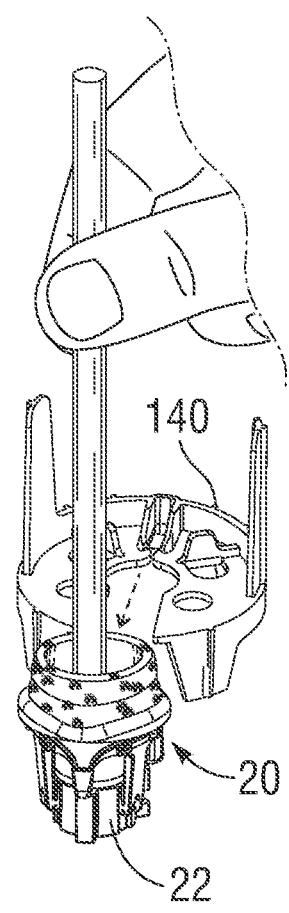
FIG. 19C shows the heart valve and holder being removed laterally from within the storage clip.

FIGS. 19A-19C illustrate several steps in removal of the prosthetic heart valve 20 from the storage jar 142. A user grasps a handling rod 160 having a balloon introducer sleeve 162 mounted on a distal end thereof. The balloon introducer sleeve 162, shown in more detail in FIGS. 21A-21E, includes external threads 164 that engage the internal threads 31 on the valve holder 22. Inserting the sleeve 162 through the valve 20 from the inflow side, the user screws the sleeve into the holder 22. The prosthetic heart valve 20 attached to the holder 22 can then be removed from the jar 142, which also removes the storage clip 140, as seen in FIG. 19B. FIG. 19C shows the user detaching the valve holder 22 from the storage clip 140 by pulling it laterally through the exit slot 156 (FIG. 18A).

Attachment of the introducer sleeve 162 in this manner provides several benefits. First and foremost, the sleeve 162 defines a throughbore at the level of the valve leaflets 74 for passage of a balloon catheter from the outflow side. Typically three valve leaflets 74 span the orifice defined by the valve support structure and have free edges that come together or "coapt" generally along three line segments oriented 120° apart that intersect at the centerline. This configuration mimics a native valve and performs well in permitting blood flow in one direction but not the other. Though extremely durable in use, the valve leaflets 74 are relatively fragile and susceptible to damage from contact with solid objects during the implant procedure, especially if they are made from bioprosthetic tissue such as bovine pericardium or a porcine xenograft. Consequently, the introducer sleeve 162 parts the leaflets 74 and provides a protective barrier between them and a balloon catheter that passes through the valve, as will be seen below. Without the sleeve 162 a balloon catheter would have to force its way backward past the coapted leaflet free edges. A further benefit of the parting sleeve 162 is the ease with which it is assembled to the holder 22. Attachment through the valve 20 to the holder 22 is intuitive, and removal of the handling rod 160 simple. The valve 20 and holder 22 assembly are stored together prior to use, often in a storage solution of glutaraldehyde or other preservative. The introducer sleeve 162 is preferably not pre-attached to the holder 22 to avoid causing any indentations in the leaflets 74 from long-term contact therewith. That is, the leaflets 74 are stored in their relaxed or coapted state.

At this stage, the user can easily rinse off the storage solution from the prosthetic heart valve 20 while it remains on the end of handling rod 160. Furthermore, and as will be explained below, handling rod 160 provides a convenient tool for positioning the heart valve 20 and holder 22 for engagement with the delivery system 110. Prior to a detailed explanation of this engagement, and the delivery system components, better understanding of the configuration and function of the balloon introducer sleeve 162 is necessary.

FIG. 20 shows the balloon introducer sleeve 162 exploded from the handling rod 160. The handling rod 160 includes an elongated preferably tubular linear handle terminating in a circular flange 166 just before a distal end 168 having a substantially star-shaped outer profile.

The balloon introducer sleeve 162 as seen in FIG. 21A-21E is substantially tubular and includes an enlarged first end 170 having an internal bore with a star-shaped profile that matches the external star-shaped profile of the distal end 168 of the handling rod 160. Indeed, the distal end 168 of handling rod 160 fits snugly within the first end 170 of the sleeve 162 up to the circular flange 166. FIGS. 21D and 21E illustrate a circular groove 172 formed just within the mouth of the first end 170 that is sized to receive a similarly shaped rib (not shown) provided on the distal end 168 of handling rod 160. Engagement between the rib and the circular groove 172 provides a suitable interference between the two components that prevents their detachment up until application of a threshold longitudinal separating force. This separating force is larger than the combined weight of the heart valve 20, holder 22, and storage clip 140, but small enough so that a user can easily pull them apart. It should be noted that the alternating ribs and channels of the respective star-shaped male and female components are tapered toward their engaging ends so that they can be rapidly connected even with some misalignment.

The tubular sleeve 162 includes the aforementioned external threads 164 adjacent to the enlarged first end 170, and has a substantially constant outer diameter to a second end 174 except for a circular groove 176. The inner lumen of the sleeve 162 extends away from the first end 170 for a short distance in a constant diameter portion 180, and then includes a narrowing taper 182 leading to a second constant diameter portion 184 that extends to the second end 174. The functional advantages of these surfaces, along with the overall purpose of the sleeve 162 will be described below.

FIG. 22 is an exploded view of the prosthetic heart valve delivery system 110, while FIG. 23 shows the system assembled. Although not shown, a balloon protector sleeve will be place around the balloon 112 for protection during shipping. The protector sleeve is a tubular component with a flared distal end, the diameter of which is larger than the ID of the introducer lumen to ensure the balloon protector is removed prior to connection of the two components. On its proximal end, the system 110 includes an end cap 190 having a luer adapter 192, a balloon extension spring 194, a spring compression pin 196, a balloon displacer 198, an inflation tube 199, and a balloon extension wire 200. In mid-portion of the system 110 includes a centering washer 202, a handpiece 204, and the aforementioned malleable handle shaft 130. Finally, distal components of the system 110 include a tubular locking sleeve 206, a valve holder adapter 208, the dilatation balloon 112, and an insert molded tip 210. The entire system preferably has a length from the proximal end of the luer adapter 192 to the balloon wire tip 210 of between about 100 and 500 mm.

FIG. 23 shows the end cap 190 and balloon displacer 198 joined together, preferably with adhesive or other such coupling means. The assembly of the end cap 190 and balloon displacer 198 may be displaced linearly with respect to the handpiece 204. The malleable handle shaft 130 extends distally from the handpiece 204 and is preferably secured thereto with adhesive or the like. The valve holder adapter 208 fixes to a distal end of the handle shaft 130, but the locking sleeve 206 slides over the handle.

One aspect of the present application that is quite significant is the integration of a balloon catheter per se within the delivery system 110. Namely, previous systems for delivering prosthetic heart valves in this manner have included separate introducer and balloon catheter elements, where the balloon catheter inserts through the tubular introducer. Although such a system may work suitably for its intended purpose, an integrated balloon catheter within the delivery system 110 provides distinct advantages. First of all, if there is a problem with the balloon, such as a puncture, the surgeon need not retract the entire balloon catheter through the introducer and introduce another one, which is time consuming. Instead, the delivery system 110 is merely decoupled from the valve holder 22, and a replacement delivery system 110 engaged to the holder. Secondly, and perhaps more evident, a single delivery system 110 replacing multiple parts speeds up the entire process and facilitate ease-of-use. The surgeon no longer has to couple multiple parts together prior to attaching to the heart valve holder, or manipulate a separate balloon catheter relative to an introducer tube. Sliding a balloon catheter through an elongated introducer opens up the risk of snags and balloon tears. Finally, the amount of packaging is reduced accordingly.

Figure 24A:
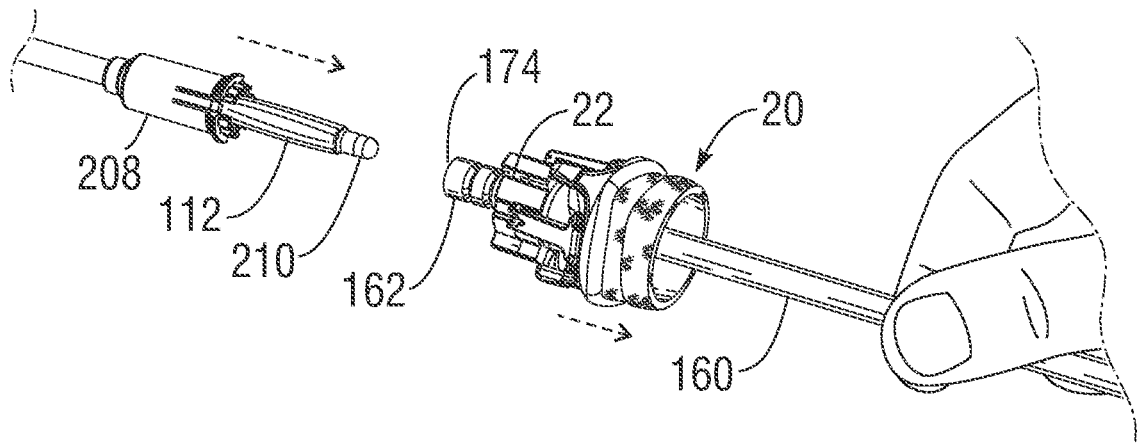
FIGS. 24A-24C illustrate several steps in coupling the delivery system of FIG. 23 to the prosthetic heart valve/holder assembly mounted on the end of the handling rod shown in FIG. 19C.
Figure 24B:
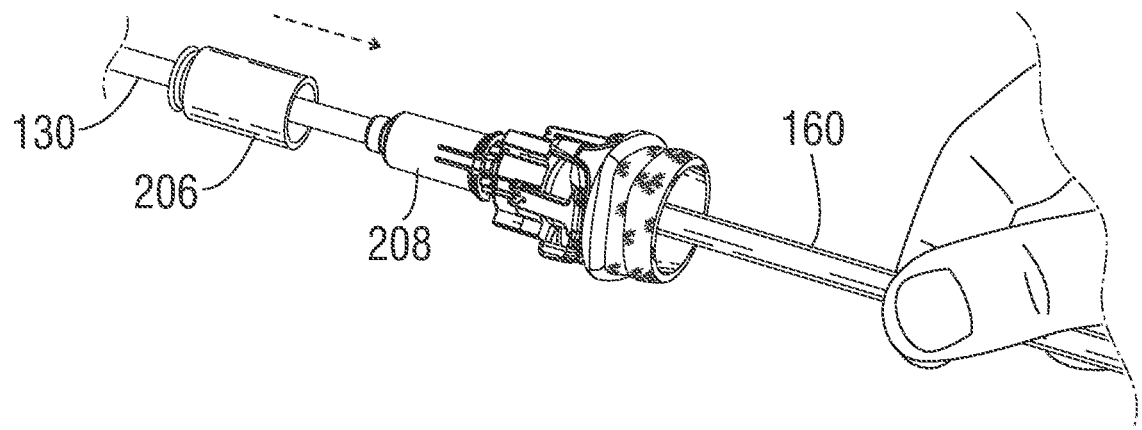
Figure 24C:
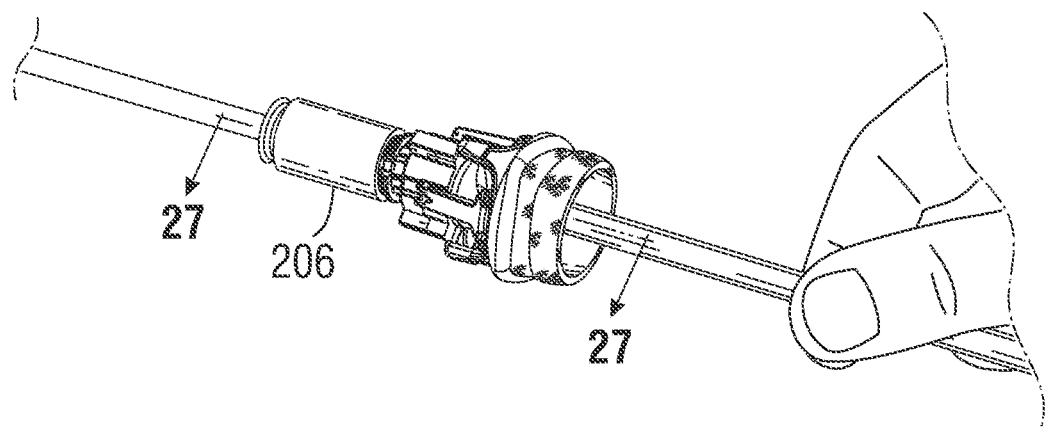

FIGS. 24A-24C illustrate several steps in coupling the delivery system 110 to the prosthetic heart valve 20 and holder 22 assembly that is held on the end of the handling rod 160. As explained above, the balloon introducer sleeve 162 threads within the holder 22. A portion of the sleeve 162 terminating in the second end 174 projects out from within the holder 22 and presents a tubular entryway for the balloon wire tip 210 and balloon 112, as seen in FIG. 24A. The user inserts the delivery system 110 through the introducer sleeve 162 until a distal shoulder 212 of the valve holder adapter 208 contacts the holder 22.

FIGS. 25 and 25A show details of the locking sleeve 206, and FIGS. 26 and 26A-26B illustrate the holder adapter 208. With reference in particular to FIG. 26B, the adapter 208 includes an elongated through bore 214 which receives the second end 174 of the introducer sleeve 162. A plurality of cantilevered fingers 216 extent longitudinally along the adapter 208, terminating at the distal end 212. Each of the fingers 216 includes an inwardly directed bump 218. Sliding the adapter 208 over the introducer sleeve 162 such that the distal shoulder 212 contacts a proximal face of the holder 22 brings the bumps 218 over the external groove 176 (see FIG. 21A).

FIGS. 24B and 24C show advancement of the locking sleeve 206 along the elongated handle shaft 130 and over the holder adapter 208. The final configuration of FIG. 24C is also shown in section view in FIG. 27. Because the inner bore of the locking sleeve 206 fits closely around the adapter 208, the cantilevered fingers 216 are retained in their aligned orientation with the bumps 218 in the groove 176 of the sleeve 162. The locking sleeve 206 desirably frictionally engages the exterior of the adapter 208 to prevent two parts from easily coming apart. Alternatively, a separate detent or latch may be provided for more security. Ultimately, when the locking sleeve 206 is in the position of FIG. 24C, the delivery system 110 is securely coupled to the valve holder 22. Moreover, the balloon 112 extends through the balloon introducer sleeve 162 and slightly out the inflow end of the expandable skirt 26.

Another advantageous feature of the present application is a keyed engagement between delivery systems 110 and holders 22 for the same size of heart valves. As seen previously in FIG. 6A, the hub portion 30 of the holder 22 has an internal star-shaped bore 36 which is sized and patterned to be keyed to an external star-shaped rim 220 provided on the holder adapter 208 (see FIGS. 26A and 26B). Because the balloon catheter is integrated with the delivery system 110, and each balloon catheter is sized for a particular valve, only the delivery system 110 which is designed for that particular valve should be coupled to its holder. That is, each expansion skirt 26 must be expanded to a particular diameter, which requires different sizes of balloons 112. Consequently, each differently sized valve holder and a delivery system combination has a unique star-shaped pattern which prevents mating with a different size.

Typically, the delivery system is packaged separately from the heart valve and holder, and this keying arrangement prevents misuse of the wrong delivery system. Additionally, if the balloon breaks and another delivery system must be rapidly obtained and utilized, the keying arrangement prevents the wrong delivery system from being substituted. There are typically 6-8 valve sizes in 2 millimeter increments, and thus a similar number of unique keyed couplings will be provided. Furthermore, the star-shaped pattern disclosed permits engagement at a plurality of rotational orientations. In a preferred embodiment, the user must rotate the delivery system 110 no more than 30° before the star-shaped rim 220 of the adapter 208 mates with the internal star-shaped bore 36 of the holder 22. This is extremely beneficial if changing out the delivery system 110, because the original elongated handle shaft 130 may be bent into a particular orientation (see below) which is much easier to replicate if the keyed features do not have to be oriented in only one or two angular relations.

Figure 28:
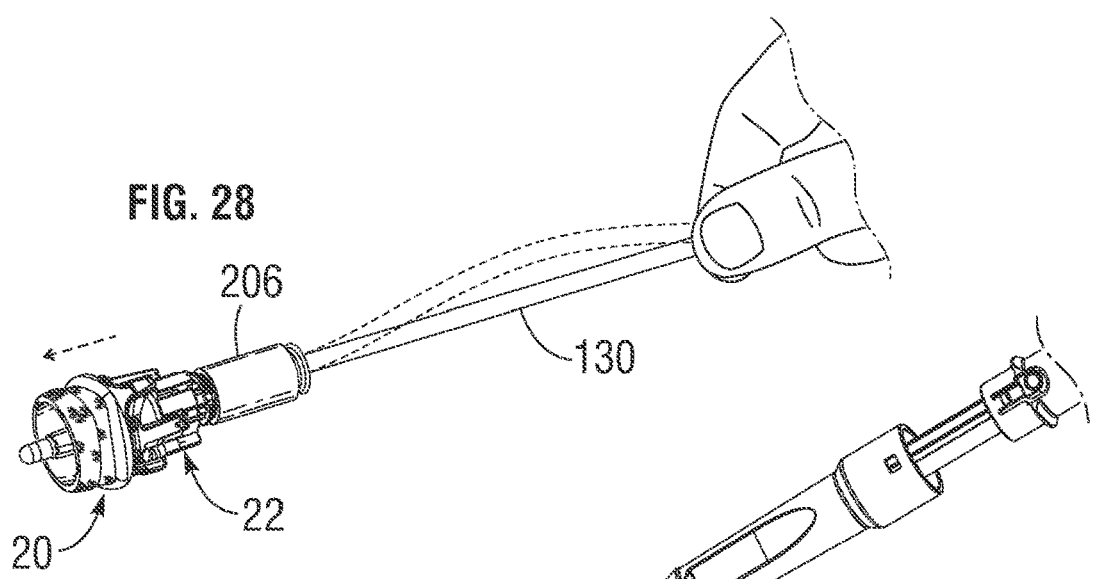
FIG. 28 is a perspective view showing the heart valve/holder assembly mounted on the end of the delivery system with the handling rod removed, and illustrating the malleable nature of an elongated handle shaft of the delivery system.
Figure 29:
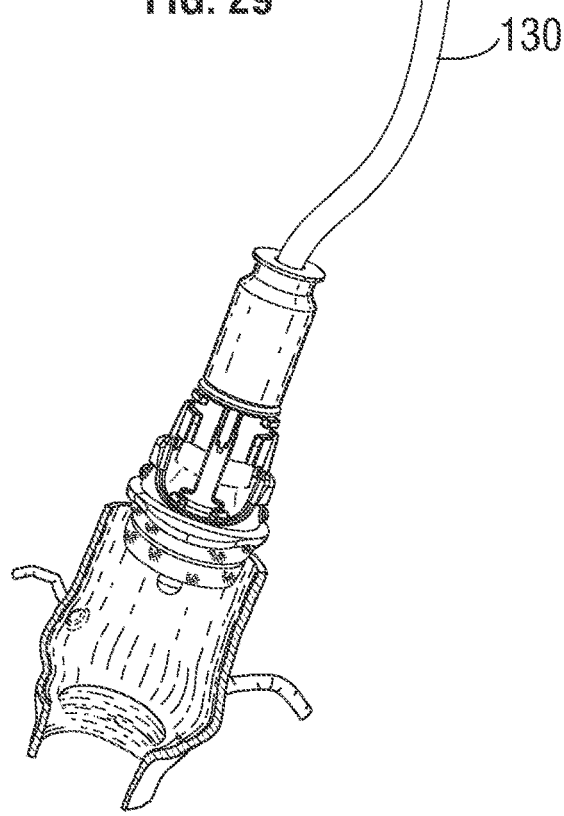
FIG. 29 is a schematic perspective view of advancement of the heart valve/holder assembly on the end of the delivery system toward a target aortic annulus, again illustrating the advantageous malleability of the elongated delivery system handle shaft.

FIG. 28 is a perspective view showing the assembly of the heart valve 20 and holder 22 mounted on the end of the delivery system 110 with the handling rod 160 removed. In a preferred embodiment, the elongated handle shaft 130 is malleable or bendable into various shapes. FIG. 29 also shows the advantageous malleability of the elongated delivery system handle shaft 130. This bendability of the handle shaft 130 significantly enhances the ability of a surgeon to correctly position the heart valve 20 as it advances toward the annulus. Often, access passageways into the heart during a surgical procedure are somewhat confined, and may not provide a linear approach to the annulus. Accordingly, the surgeon bends the handle shaft 130 to suit the particular surgery.

Various materials and constructions may be utilized to provide a malleable tube for use as the handle shaft 130. For example, a plurality of Loc-Line connectors should be used which provide axial rigidity with bending flexibility. The handle shaft 130 must be axially rigid so that it can position the heart valve in the annulus with confidence. Another example is a plastic tube having a metal coil embedded therein to prevent kinking. In a preferred embodiment, an aluminum tube having a chromate (e.g., Iridite) coating is used. Aluminum is particularly well-suited for forming small tubes that can be bent without kinking, but should be coated with Iridite or the like to prevent deterioration in and reaction with the body. A highly desirable feature of the handle shaft 130 is its resistance to recoil. Aluminum provides an insignificant level of recoil that permits the surgeon to bend the shaft 130 to conform to a particular patient's anatomy without worry that the handle shaft will change its shape once bent. On the other hand, though stainless steel will be sufficient if it remains straight, any bending will be followed by recoil so that the surgeon cannot be assured of the final orientation of the shaft. As mentioned, Loc Line connectors may work, but a solid shaft that is easy to sterilize is preferred.

The limit on recoil may be quantified by bending different materials and evaluating the force required to bend in conjunction with the amount of recoil. For these tests, the bend force is the peak force needed to bend the malleable handle of a fully assembled delivery system to 90° with a 1.5" radius. The recoil is the degrees of recoil after the malleable handle is bent as such. For instance, a 5° recoil means that the 90° bend angle recovered to a bend angle of 85°. A number of materials are suitable for use as the delivery system handle shaft 130, in particular various biocompatible metals and alloys. Stainless steel (SS) has better recoil property than aluminum (Al), meaning it recoils less, yet requires a much higher bend force due to its higher tensile property. A SS shaft handle will have to be relatively thin to reduce the force required, and could be made with longitudinal slots to reduce the bend force even more. However the cost of a SS handle with slots much more than that of an Al handle. Al is preferred for its low recoil propensity and relative ease to bend it.

FIGS. 30 and 30A are elevational and broken longitudinal sectional views, respectively, of the heart valve delivery system 110 with a balloon 112 in a retracted position, while FIGS. 31 and 31A are similar views with the balloon 112 extended. The balloon catheter of the delivery system 110 has two binary longitudinal positions relative to the handpiece 204 and its associated structures. In a retracted position shown in FIGS. 30 and 30A, the connected end cap 190, balloon displacer 198, inflation tube 199, and balloon 112 are retracted to the left with respect to the handpiece 204. Note the spacing A between a distal shoulder 230 of the balloon displacer 198 and the centering washer 202 within the handpiece 204. The balloon 112 resides partway within the holder adapter 208 in this position. Once the balloon catheter is displaced to the right, as seen in FIGS. 31 and 31A, the spacing A disappears and the balloon 112 projects out from within the handle adapter 208.

The delivery system 110 provides an extremely accurate system for positioning the balloon 112 relative to the heart valve, and in particular the anchoring skirt 26. Because of the simple engagement between the handle adapter 208 and the handle shaft 130, very little tolerance errors are introduced. The handle adapter 208 is fixed to the elongated handle shaft 130, which in turn is fixed to the handpiece 204. Movement of the balloon catheter structures relative to the handpiece 204 thus displaces the balloon 112 in a 1:1 correspondence with respect to the holder 22 and attached heart valve 20. Furthermore, a pair of small resilient detents 232 provided on the balloon displacer 198 engage similarly sized cutouts 234 on the proximal end of the handpiece 204. This locks the position of the balloon catheter with respect to the handpiece 204, or in other words locks the position of the balloon 112 with respect to the anchoring skirt 26.

The balloon inflation tube 199 and balloon extension wire 200 are formed of materials that have column strength but are relatively flexible in bending. As explained further below, the wire may be Nitinol while the inflation tube 199 is desirably formed of a braid reinforced thermoplastic elastomer (TPE) such as a polyether block amide known under the tradename of PEBAX® (Arkema of Colombes, France).

As the delivery system 110 may be subjected to several bends in use, care must be taken to ensure that the concentric tubes and wire do not introduce misalignment. That is, smaller diameter objects tend to travel shorter paths within larger concentric tubes, thus cause them to extend out of the distal end of the tubes after being bent. As such, the balloon inflation tube 199 is desirably closely sized to match the inner diameter of the malleable handle shaft 130. In one embodiment, the outer tube of the malleable handle shaft 130 has an OD of 0.197±0.003" (5.004±0.076 mm), and an ID of 0.153±0.002" (3.886±0.051 mm) The balloon inflation tube 199 has an OD of 0.140±0.002" (3.556±0.051 mm), and an ID of 0.114±0.002" (2.896±0.051 mm). This means the difference in radii between the ID of the larger tube 130 and the OD of the smaller tube 199 is only 0.165 mm [(3.886−3.556)±2], and the OD of the smaller tube is more than 90% (91.5%) of the ID of the larger tube. This close matching of tube sizes ensures that the axial position of the balloon 112, which is affixed to the end of the balloon inflation tube 199, does not shift much relative to the axial position of the prosthetic heart valve 20, which is affixed relative to the end of the malleable handle shaft 130. The balloon extension wire 200 has a size relative to the ID of the balloon inflation tube 199 sufficient to permit good flow of saline when filling the balloon 112. In one embodiment, the wire 200 has an OD of 0.037+0.002/−0.001" (0.94+0.13/−0.025 mm).

The present delivery system advantageously prevents premature advancement of the balloon catheter so that the balloon 112 remains retracted within the confines of the prosthetic heart valve 20 during advancement of the valve into position within the aortic annulus. As will be readily apparent, the surgeon advances the entire delivery system 110 with the heart valve 20 at its distal end through the open chest cavity or port and through the aortic arch and down the ascending aorta into the implant position. Pushing on the proximal end of the delivery system 110 carries the risk of accidentally displacing the balloon catheter relative to the handpiece 204 prior to the desired deployment stage. A protruding balloon 112 may damage the coronary ostia or make insertion difficult by enlarging the device profile. Consequently, the present application contemplates various means for physically preventing movement of the balloon catheter, preferably coupled with a visual reminder not to deploy the catheter prematurely.

Figure 32:
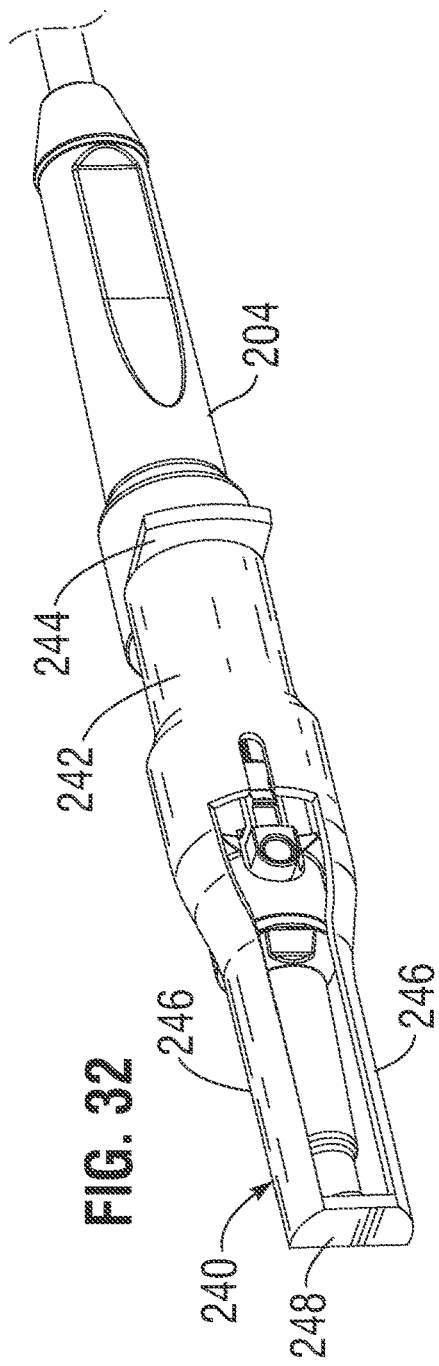
Figure 33A:
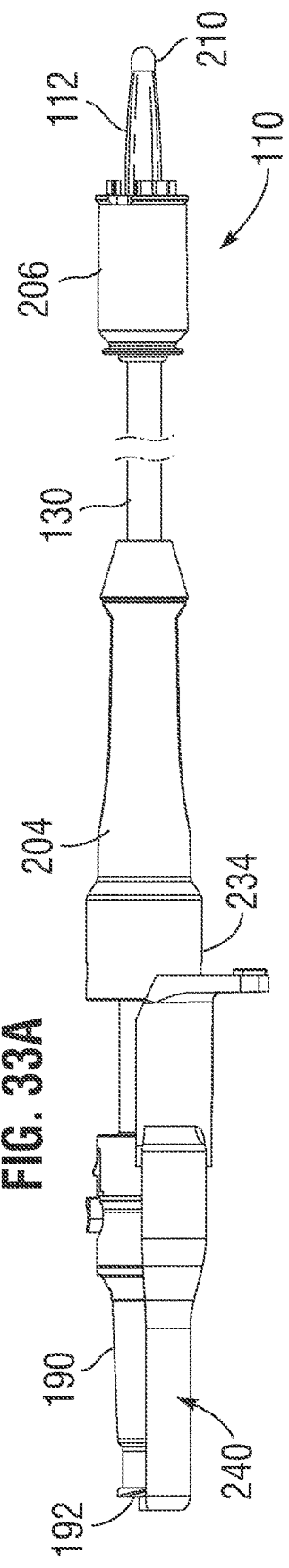
FIGS. 33A and 33B are elevational and broken longitudinal sectional views, respectively, of the heart valve delivery system with a balloon catheter held in the retracted position by the locking clip.
Figure 33B:
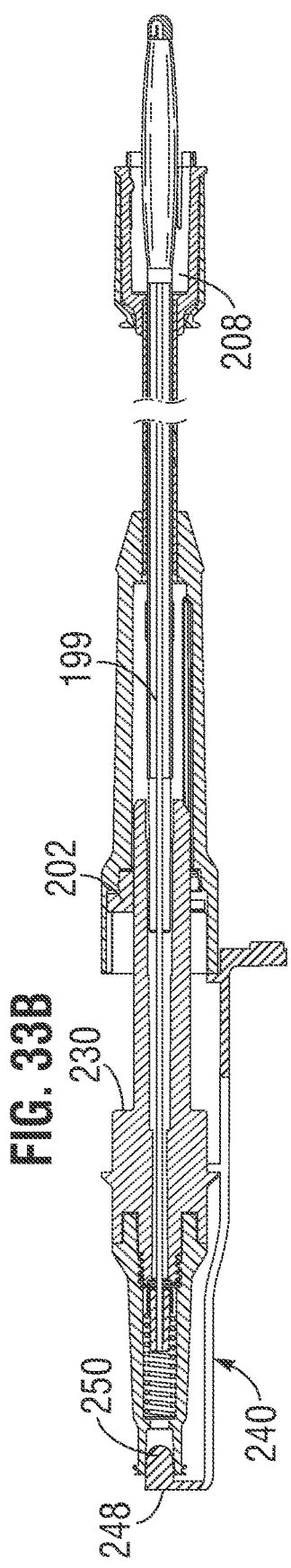

For instance, FIG. 32 is a perspective view of the proximal end of the exemplary heart valve delivery system 110 showing a locking clip 240 exploded therefrom. As seen in FIGS. 33A and 33B, the locking clip 240 snaps to the exterior of the end cap 190 and handpiece 204 and holds the balloon catheter in a retracted position by presenting a physical barrier to relative movement of those two elements. The locking clip 240 includes a semi-tubular body 242 terminating in a thumb ledge 244 on its distal end. The semi-tubular body 242 has internal features that match the external features on the handpiece 204. Specifically, although not shown, the interior of the semi-tubular body 242 has circumferential ridges that engage the proximal end of the handpiece 204 and both frictionally engage the handpiece and provide an impediment to distal axial movement of the clip relative to the handpiece. The locking clip 240 bifurcates into two elongated rails 246 that extend proximally from the body 242 and come together at a proximal bridge 248 having an inwardly-directed node 250 (FIG. 33B). The node 250 fits closely within the lumen of the luer adapter 192 and provides a physical barrier and visual indicator to prevent premature attachment of a balloon inflation source. Further, interior features on the two elongated rails 246 engage matching contours on the balloon catheter end cap 190.

The clip 240 assembles to the delivery system 110 as shown with the balloon catheter in the retracted position. First the node 250 inserts into the luer adapter 192 lumen, and then the clip 240 snaps over the end cap 190 and handpiece 204. The connection between the clip 240 and delivery system 110 is frictional and the clip can easily be removed, but provides a physical barrier and visual reminder to prevent premature distal deployment of the balloon catheter and connection of a balloon inflation source. Furthermore, the thumb ledge 244 on the clip 240 provides a convenient ergonomic feature that facilitates control of the system advancement. After the surgeon advances the system and prosthetic heart valve 20 into position within the aortic annulus, he/she removes the clip 240 to enable deployment of the balloon catheter and connection of an inflation source. The clip 240 is typically plastic and is discarded.

Other possible barriers to premature balloon catheter deployment/balloon inflation are contemplated. In one configuration shown in FIGS. 34 and 35, a toggle lever 260 connects to both the end cap 190 and handpiece 204 and may be displaced in either direction to alternately deploy and retract the balloon catheter. More specifically, the toggle lever 260 includes a thumb piece 262 that projects outward from the delivery system 110, a hinge 264 pivotally mounted to the handpiece 204, and a blocking end 266 that fits in the axial space between the end cap 190 and handpiece 204 in the retracted position of FIG. 34. A cam linkage 268 pivotally attaches midway along the thumb piece 262 and pivotally attaches at its opposite end to the end cap 190.

Figure 34:
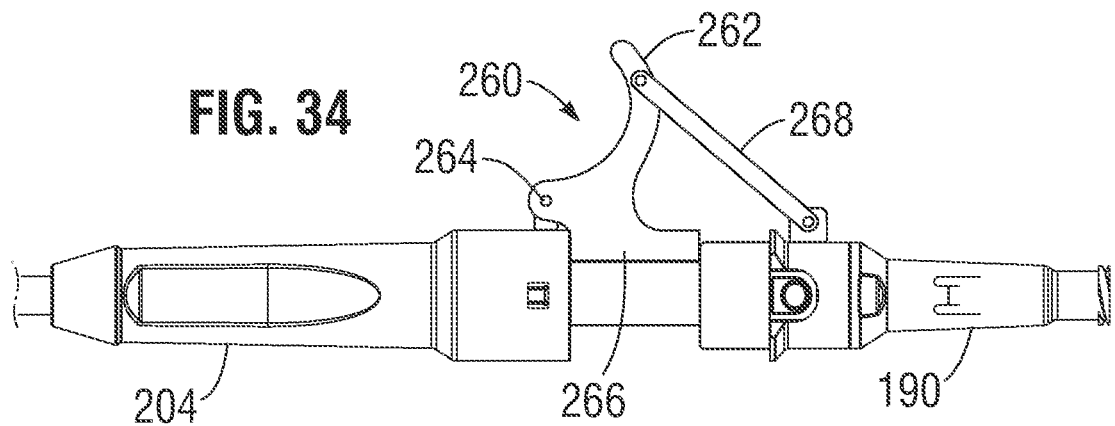
FIGS. 34-36 are views of an alternative embodiment for preventing premature deployment of the balloon catheter in the valve delivery system using a toggle lever.

The retracted position of FIG. 34 corresponds to the retracted position of the balloon catheter in the delivery system 110 as in FIG. 31. In this state, the blocking end 266 fits closely between the facing surfaces of the spaced-apart end cap 190 and handpiece 204, and thus presents a physical barrier to distal advancement of the end cap and balloon catheter within the delivery system 110. At the appropriate moment, the surgeon pivots the toggle lever 260 in the direction of the arrow 270 in FIG. 35 which simultaneously removes the blocking end 266 from between the end cap 190 and handpiece 204 and pulls the end cap toward the handpiece by virtue of the cam linkage 268. Pivoting the toggle lever 260 the full extent of its travel completely deploys the balloon catheter and displaces the balloon 112 to its proper position within the anchoring skirt 26. That is, the distance traveled by the end cap 190 relative to the handpiece 204 is calibrated to be precisely the same distance necessary to advance the balloon 112 to a location for proper expansion of the anchoring skirt 26 that ensures its optimum hemodynamic performance. Consequently, not only does the toggle lever 260 prevent premature deployment of the balloon catheter, but it also ensures advancement thereof prior to balloon inflation, and in so doing ensures accurate advancement. Additionally, due to the connected nature of the toggle lever 260, there are no loose parts to interfere with the procedure or potentially be misplaced during the surgery. Further details on ensuring the correct positioning of the balloon 112 within the skirt 26 are provided below.

Figure 36:
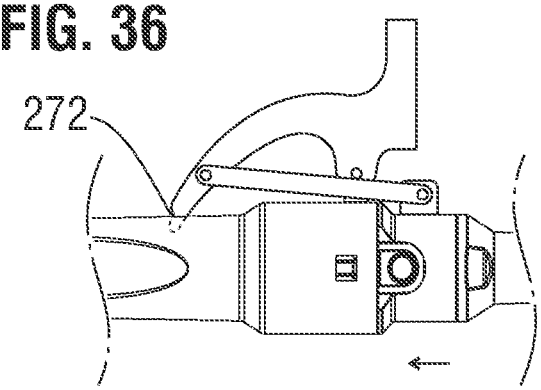

When the surgeon pushes the toggle lever 260 into the advanced position, it desirably snaps into some feature on the handpiece 204 to signal complete deployment and to hold it in place. For instance, FIG. 36 shows a distal tip 272 of the lever 260 captured in a complementary notch or recess in the exterior of the handpiece 204. Of course, numerous other such configurations are possible, and in general the toggle lever 260 and its interaction with the end cap 190 and handpiece 204 are exemplary only. Alternatives such as sliders, rotating knobs or levers, colored or even lighted indicators, etc., are contemplated. The purpose of such alternatives is to prevent premature advancement of the balloon catheter, ensure advancement before balloon inflation, and ensure accurate advancement within the anchoring skirt 26 of the prosthetic heart valve 20.

Figure 52A:
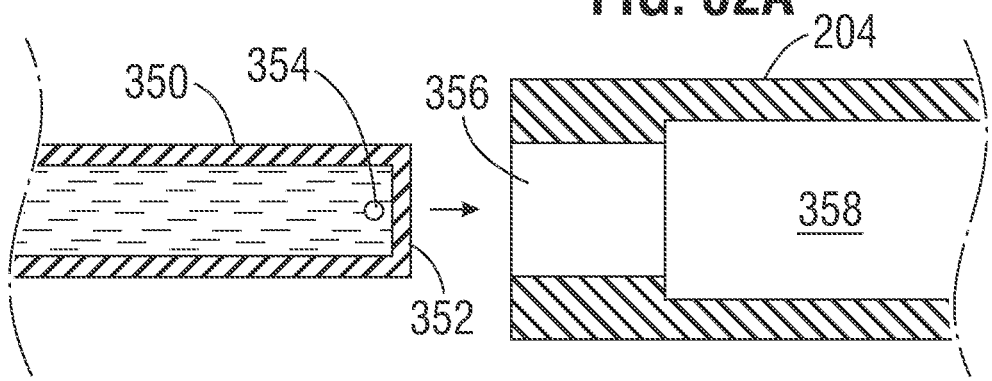
Figure 52B:
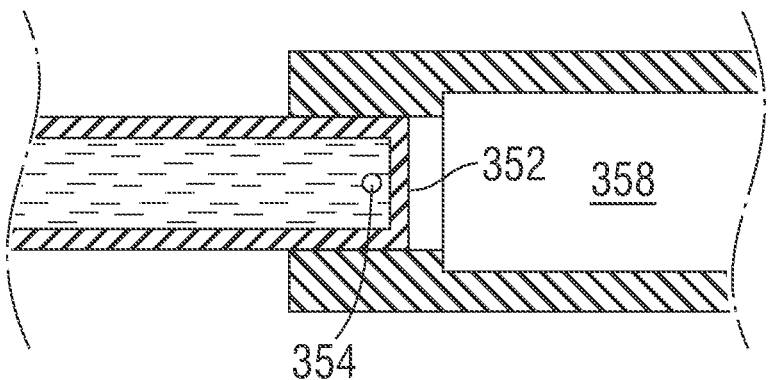
Figure 52C:
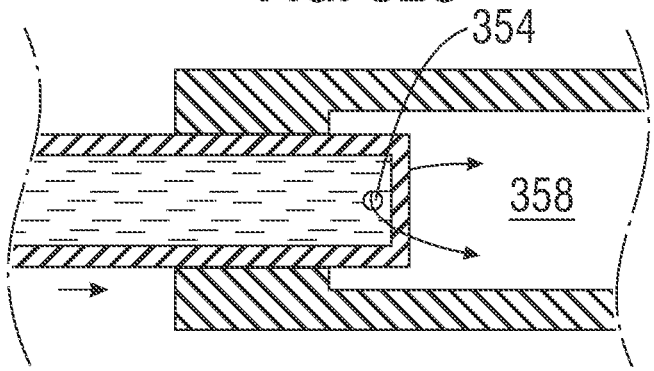
Figure 53:
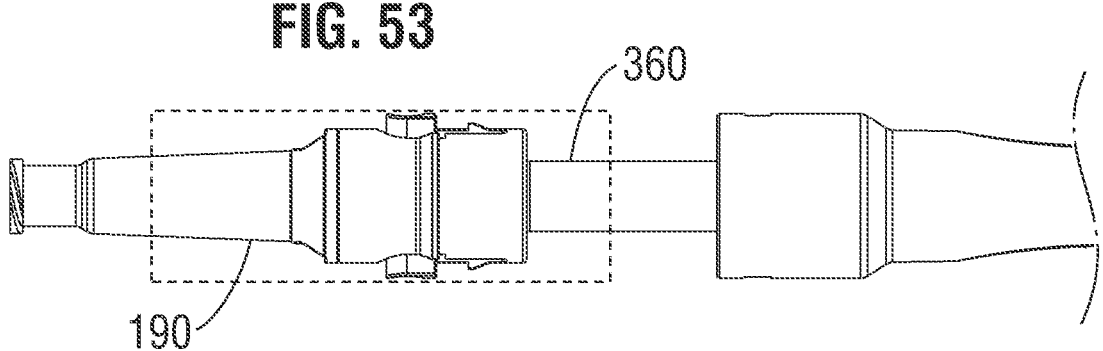
Figure 54A:
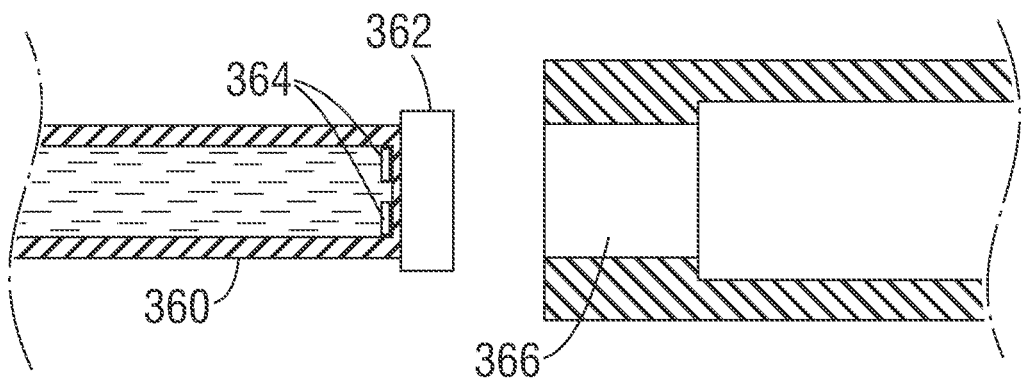

Other devices to prevent premature balloon catheter deployment/balloon inflation are contemplated, including physical impediments such as the toggle lever 260 described above as well as visual or audible indicators to prevent deployment. For instance, an alternative configuration that impedes balloon inflation fluid flow prior to catheter advancement is seen in FIGS. 52-54 and described below.

Figure 37:
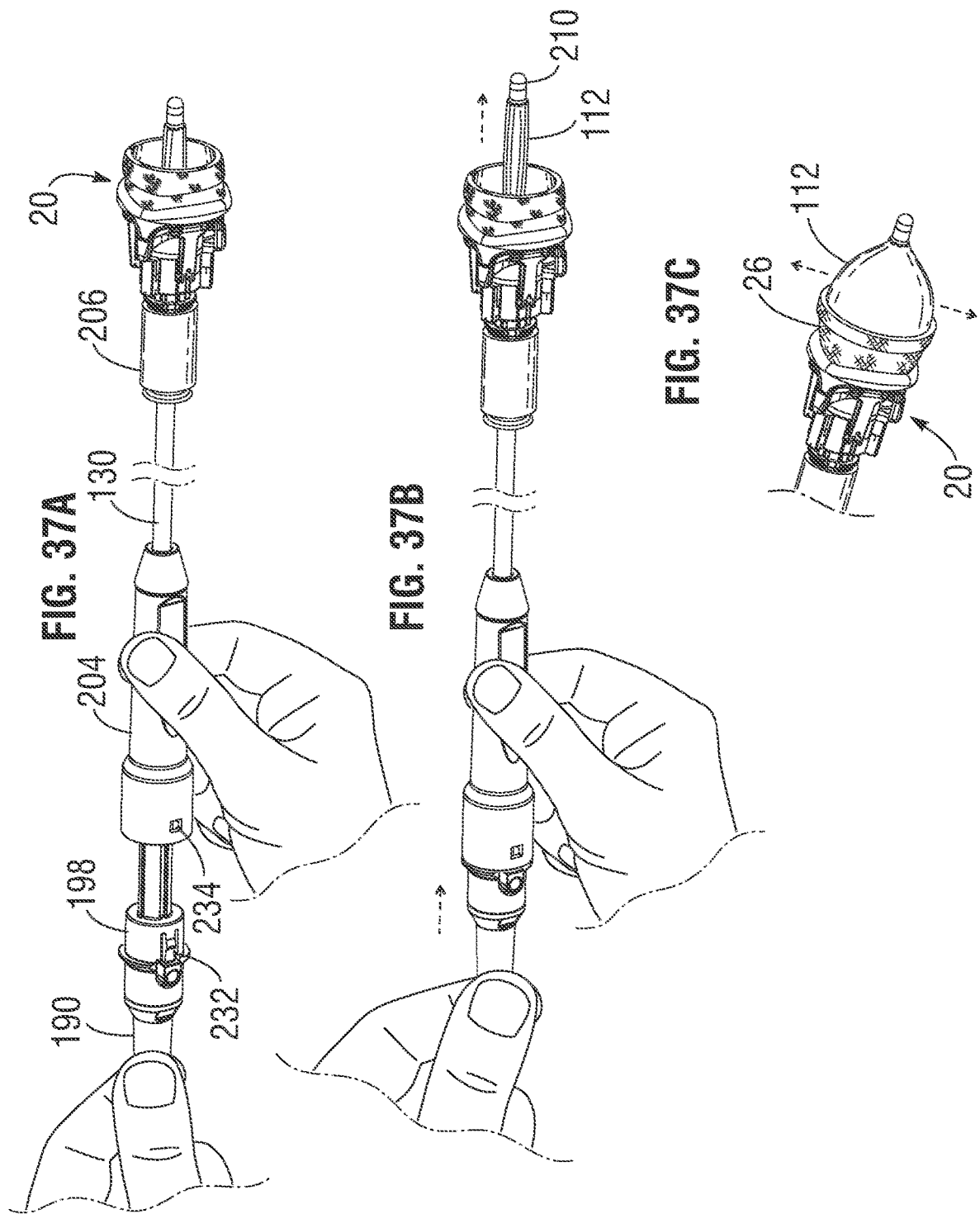
FIGS. 37A-37C are perspective views illustrating deployment of the balloon catheter through the prosthetic heart valve and expansion of the balloon to expand the anchoring skirt, analogous to FIGS. 16E-16G.

FIGS. 37A-37C are perspective views illustrating deployment of the balloon catheter through the prosthetic heart valve and expansion of the balloon to expand the anchoring skirt, analogous to FIGS. 16E-16G.

FIG. 37C shows the balloon 112 inflated to expand and deploy the anchoring skirt 26 against the annulus. The anchoring skirt 26 transitions between its conical contracted state and its generally tubular or slightly conical expanded state. Simple interference between the anchoring skirt 26 and the annulus may be sufficient to anchor the heart valve 20, or interacting features such as projections, hooks, barbs, fabric, etc. may be utilized. For example, a distal end of the anchoring skirt (see lower edge 94 in FIG. 15B) may expand more than the rest of the anchoring skirt so that peaks in the strut row farthest from the prosthetic valve project outward into the surrounding annulus.

Also, the balloon 112 may have a larger distal expanded end than its proximal expanded end so as to apply more force to the free end of the anchoring skirt 26 than to the prosthetic valve member 24. In this way, the prosthetic valve member 24 and flexible leaflets therein are not subject to high expansion forces from the balloon 112.

When assembled as seen in FIG. 30A, an elongated lumen (not numbered) extends from the proximal luer adapter 192 to the interior of the balloon 112. The luer adapter 192 provides an attachment nipple for an inflation system (not shown) for inflation of the balloon 112. The balloon 112 is desirably inflated using controlled, pressurized, sterile physiologic saline. The lumen passes through the end cap 190, balloon displacer 198, and then through the inflation tube 199 which is affixed at one end to the displacer and at another end to a proximal end of the balloon. The balloon displacer 198 thus moves the proximal end of the balloon.

The present application also provides an improved balloon 112 and system for deploying and removing it. As seen in the deflated views, the balloon 112 preferably comprises a plurality of longitudinal pleats which help reduce its radial configuration for passage through the delivery system 110. Furthermore, the balloon extension wire 200 extends through the balloon inflation tube 199, through the dilatation balloon 112, and terminates in a molded balloon wire tip 210 affixed to the distal end of the balloon. The path of the wire 200 is seen in the sectional views of FIGS. 30A and 31A. Although the proximal end of the balloon 112 fastens to the inflation tube 199, and thus from there to the handpiece 204, the distal tip 210 does not. Instead, the wire 200 fastens to the spring compression pin 196 which translates within a lumen in the proximal end cap 190, and engages the balloon extension spring 194 therein. In this regard, the balloon extension wire 200 moves independently within the delivery system 110 instead of being fixedly attached. This, in turn, allows the distal end of the balloon 112 to move with respect to the proximal end. This arrangement is seen best in FIGS. 38-40.

The exemplary delivery system balloon 112 has a relatively high diameter-to-length ratio compared to other surgical balloons, such as those used to expand cardiovascular stents. This makes it particularly difficult for the balloon 112 to return to a small geometry upon deflation after deployment. Balloons of such size ratios tend to "butterfly" by forming wings that prevent removal through the valve holder without the application of high forces, which may cause damage to the valve itself. The exemplary delivery system 110 and balloon 112 include several advances from earlier heart valve delivery systems that facilitate a traumatic removal of the balloon 112. First, as mentioned above, a series of longitudinal pleats are heat set into the wall of the balloon 112 to facilitate self-collapse during deflation. Further, the distal end of the balloon 112 moves relative to the proximal end to enable lengthening of the balloon during deflation. This lengthening occurs automatically by virtue of the wire 200 which is spring-biased to stretch the balloon longitudinally. It should be noted that easy deflation and removal of the balloon 112 permits rapid replacement of the balloon catheter in case of a problem, such as insufficient inflation.

FIG. 38 is a sectional view with the balloon 112 advanced as in FIG. 31A. In this configuration, the spring 194 has a length of $x_1$, and the spring compression pin 196 is all the way to the right within the end cap cavity. In this "resting" state with the balloon 112 deflated, the spring 194 may be relaxed or under a slight compressive preload. Subsequently, saline is introduced via the proximal luer connector 192 and travels distally along the length of the balloon catheter components to inflate the balloon 112. Inflation of the balloon 112 causes radial expansion but axial foreshortening, thus displacing the distal tip 210 to the left as shown in FIG. 39. This, in turn, displaces the balloon extension wire 200 and attached spring compression pin 196 to the left against the resiliency of the spring 194. Ultimately, the spring is compressed to a second shorter length $x_2$. In a preferred embodiment, the spring 194 undergoes complete compression to its solid length so as to provide a positive stop on proximal movement of the wire 200 and attached balloon distal tip 210. This helps ensure proper expansion of the anchoring skirt 26, as will be more fully explained. The proximal movement of the distal tip 210 against the reaction force of the spring 194 places the wire 200 in compression.

Finally, FIG. 40 illustrates deflation of the balloon 112 by pulling a vacuum through the inflation movement and return movement to the right of the distal tip 210 and balloon extension wire 200. This movement is encouraged, and indeed forced, by expansion of the spring 194. The force of the spring 194 is calibrated so as to elongate the pleated balloon 112 so it assumes its previous radially constricted diameter, or as close as possible to it. Furthermore, the wire 200 may be rotated about its axis to further encourage constriction of the balloon 112 by causing the pleats to further fold in a helical fashion. This can be accomplished by extending a portion (e.g., see portion 200' in FIG. 40) of the wire 200 from the proximal end of the Luer connector 192 so as to be grasped and rotated by forceps, or otherwise providing a lever or thumb plunger (not shown) fastened to the wire and projecting laterally from the system. Still further, the spring compression pin 196 may be constrained to translate within a helical track. In the latter case, the pin 196 may include a bayonet-type mount that locks within detents in both ends of the helical track. The spring-biased lengthening and consequent radial contraction of the balloon 112 facilitates its proximal removal through the now-deployed prosthetic heart valve 20.

As mentioned above, the balloon 112 desirably has a frusto-conical profile that expands the anchoring skirt 26 into a frusto-conical expanded state. More typically, and as shown in FIG. 39, the balloon 112 is generally spherical when expanded. Nevertheless, a spherical balloon will outwardly expand the anchoring skirt 26 into a frusto-conical shape due to the connection at one end of the inner stent frame 80 to the heart valve sewing ring 62 (see FIGS. 15A/15B). To ensure sufficient and proper outward expansion of the anchoring skirt 26, the balloon 112 is axially positioned such that a midline 280 indicated around the maximum circumference (equatorial line) thereof registers with the distalmost end 282 of the skirt. In doing so, the widest part of the balloon 112 corresponds to the end of the skirt 26, which tends to expand the skirt conically. A tolerance of 1-2 mm between the location of the midline 280 and the distalmost end 282 of the skirt is acceptable which may occur for different sizes of valves and associated skirt 26.

Figure 41:
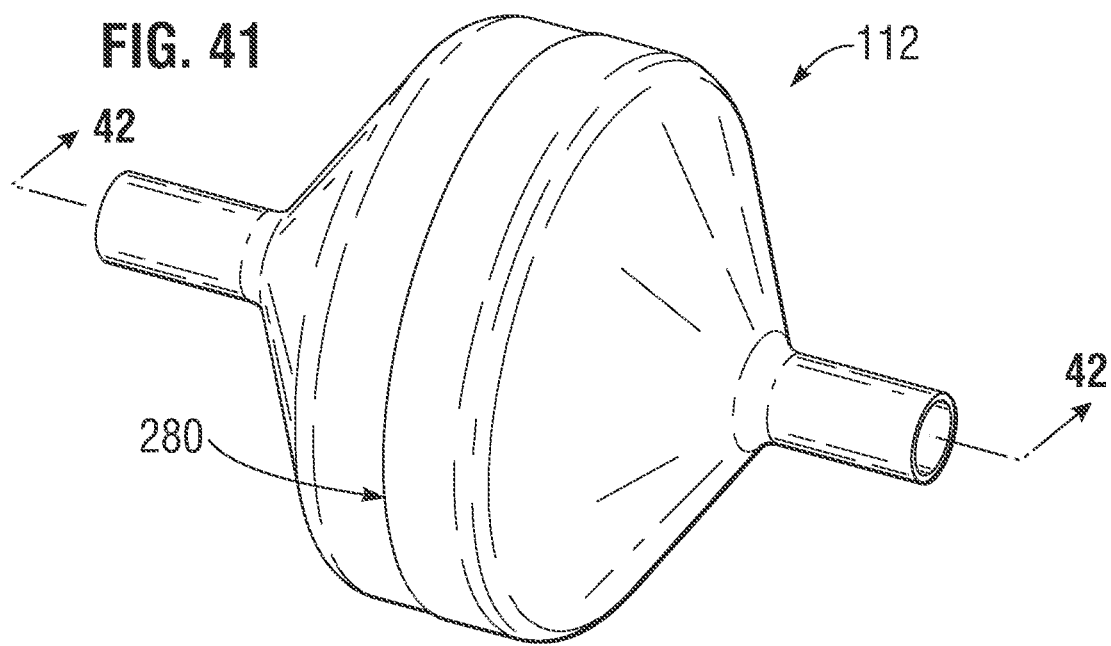
FIGS. 41-42 are perspective and sectional views of an exemplary stepped balloon construction used in the valve delivery system disclosed herein.
Figure 42:
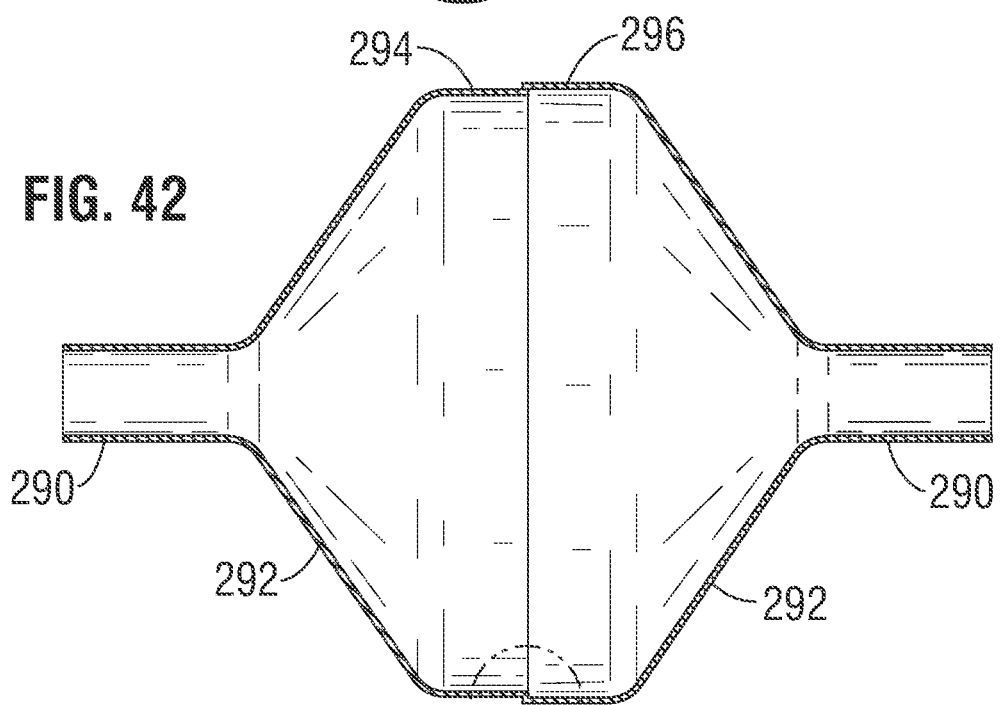
Figure 42A:
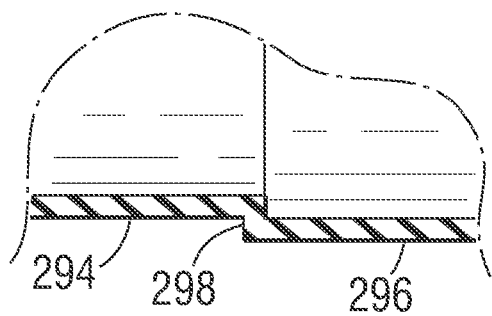
FIG. 42A is a detail of the step.

As seen in FIGS. 41-42 an exemplary stepped balloon construction is shown wherein the balloon 112 is desirably offset molded to form the midline 280 as a small step in the balloon wall. That is, the opposed balloon mold halves will have a slightly different diameter, such that a physical step in the final product is formed—the midline 280. Alternatively, the midline 280 may be formed by a small equatorial rib or indent formed in the mold process, or even with an ink marking, though the latter may not be suitable for surgical application. The midline 280 will be visible on the balloon 112 in both its deflated and inflated states, and is extremely useful as a reference line during assembly and quality control of the delivery system 110. For instance, the components of the system 110 are assembled and the location of the balloon 112 in its advanced position is checked against the anchoring skirt 26. Since the balloon 112 foreshortens when it is inflated, the reference midline 280 should be beyond the distalmost end 282 of the skirt 26 when the balloon is deflated, a location that can easily be inspected during assembly.

Although FIGS. 41 and 42 illustrate a geometric molded shape of the expansion balloon 112, in use, saline or other fluid injected into the balloon cavity will result in a more rounded inflated shape, such as seen in FIG. 39. The exemplary molded shape shown is preferred because of the relatively large diameter to which the distal end of the frame of the anchoring skirt 26 expands. More particularly, the exemplary shape includes proximal and distal tubular ends 290 to which elongated elements of the balloon catheter are secured. A pair of conical sidewalls 292 angle outward toward the midline of the balloon 112 from the tubular ends 290, while a pair of offset axial sidewalls 294, 296 complete the balloon 112, spanning the midline or equator. One or the other of the axial sidewalls 294, 296 has a larger diameter, with the axial sidewalls being joined at a step 298 that indicates the equatorial midline 280 of the balloon 112. Again, this construction may be formed using an offset mold, wherein one mold half is larger than the other.

Another advance regarding the balloon 112 is in the steps for calibrating its fill capacity. Existing balloon catheters are calibrated by monitoring the volume injected to expand the balloon to a desired diameter. In contrast, the balloon 112 for the delivery system 110 is calibrated by pressure. One or more balloons are tested during verification testing to see how much pressure is needed to expand an anchoring skirt 26 to a particular diameter, depending on the final desired size of the skirt. During assembly, each balloon is inflated to see that it expands to within the expected range. In use, a pressure gauge attaches in the fill line to monitor the fill pressure. The surgeon inflates to the target pressure, and as further confirmation can verify the resulting skirt expansion visually or with the aid of a scope or radiographic markers and the like.

It should be noted that the flared shape of the expanded anchoring stent 26 (see FIG. 16H or FIG. 46A, below) may help improve flow through the prosthetic heart valve relative to a valve without the skirt. In some patients, ventricular hypertrophy tends to cause an inward bulging of the left ventricle wall just below the aortic valve. The conical skirt 26 will expand outward against this anomaly, and in doing so will expand the inflow passage to the aortic valve.

The balloon extension wire 200 seen extending the length of the delivery system in FIGS. 38-40 flexes in order to adapt to bending of the surrounding handle shaft 130 (e.g., see FIG. 29). In a preferred embodiment, the wire 200 is Nitinol, though other suitable metals such as stainless steel could be used. Nitinol combines good column strength with excellent flexibility. However, the delivery system 110 will be provided in an array of sizes for different sized orifice prosthetic heart valves, and the largest balloons will exert a significant compressive force on the wire 200 when inflated. To prevent the wire 200 from buckling, and in lieu of stiffening the wire, a short hypotube 201 may be provided, as seen in FIGS. 22 and 39. The hypotube 201 affixes to the wire 200 at its distal end, such as by being molded together with the wire and the balloon catheter tip 210 or other suitable means. The hypotube 201 provides added column strength to the wire 200 along its length that projects out of the inflation tube 199 and within the balloon 112. The hypotube 201 terminates just past the proximal end of the balloon 112 so as not to interfere much with the overall flexibility of the delivery system 110. The hypotube 201 may be made of a suitable metal such as Stainless Steel or a stiff polymer such as Nylon. The hypotube 201 has an OD of 0.059±0.005" (1.5±0.13 mm), an ID of 0.041±0.003" (1.04±0.08 mm), and a length of about 1.77" (45.0 mm).

Figure 43:
FIGS. 43, 44A-44D, and 45A-45C are external and sectional views of a distal end of a balloon extension wire and molded distal tip of the exemplary balloon catheter.
Figure 44A:
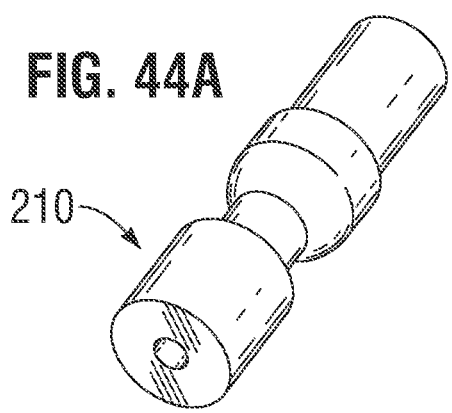
Figure 44C:
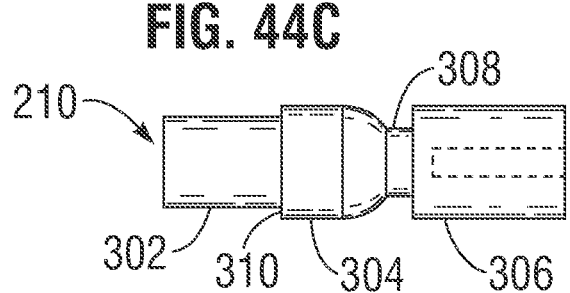
Figure 44B:
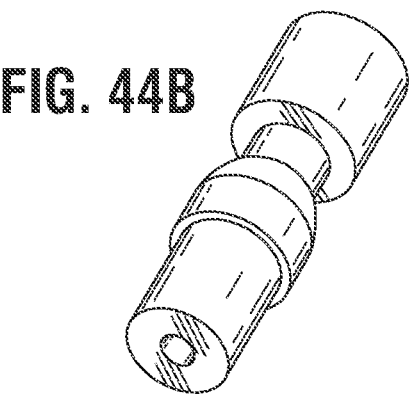
Figure 44D:
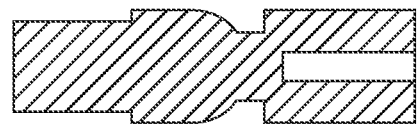
Figure 45A:
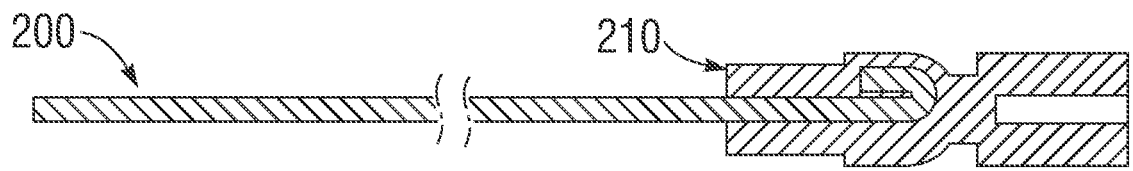
Figure 45B:
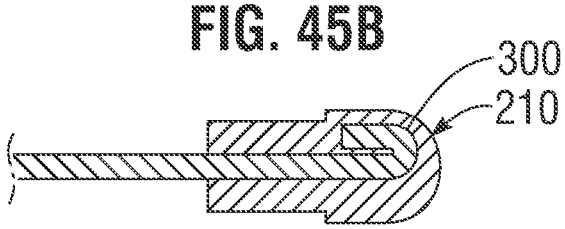

FIGS. 43-45 are external and sectional views of a distal end of the balloon extension wire 200 and distal insert molded tip 210 thereon—FIG. 45B shows the final assembly in section, with the distal end of the wire 200 embedded within the tip 210, while the other views illustrate an assembly process therefore. The insert molded tip 210 provides an anchor for the distal end of the wire 200 which experiences high axial forces during balloon expansion. More particularly, and as explained above with reference to FIG. 39, balloon expansion causes outward expansion and axial foreshortening such that the distal tubular end 290 (see FIG. 42) moves in a proximal direction. The wire 200 attaches to the distal tubular end 290 via the insert molded tip 210, and thus both move proximally as well. As previously described, inflation of the balloon 112 places the wire 200 in compression. Consequently, the connection between the wire 200 and tip 210, and between the tip 210 and tubular end 290 of the balloon 112 must be relatively robust to avoid leakage or the wire breaking free of the tip. Moreover, manufacturing concerns require as few steps as possible to form this important construct.

Accordingly, the distal end of the wire 200 is turned back on itself into a J-shaped bend 300. The bend 300 is then placed within an insert mold within which is injected material to form the molded tip 210, in the combination shown in FIG. 45A. The shape of the tip 210 after molding is seen in FIGS. 44A-44D. The tip 210 after molding includes a proximal portion having a cylindrical shaft region 302 and a hemi-spherical bulb 304, a distal portion including a tubular mandrel alignment conduit 306, and a narrow bridge 308 therebetween, identified in FIG. 44C. The mandrel alignment conduit 306 provides a convenient handle of sorts to hold the tip 210 and wire 200 securely centered within the distal tubular end 290 of the balloon 112 during a heat fusion step, typically with laser bonding. After bonding the balloon 112 to the tip 210, the mandrel alignment conduit 306 is severed at the bridge 308, resulting in the rounded end shape for atraumatic delivery as seen in FIG. 45B. The final tip 210 desirably has a relatively short axial length of between about 6-8 mm. The length of the wire 200 may be 300-400 mm, and has a diameter of 1 mm or less.

Figure 45C:
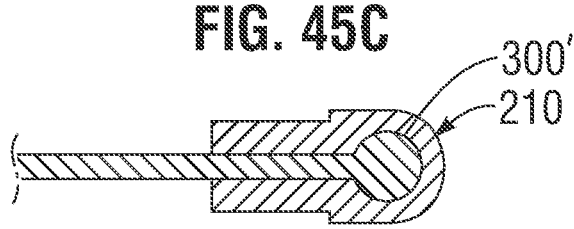

An alternative assembly is seen in FIG. 45C, where the J-shaped bend 300 on the end of the wire 200 has been replaced with a bead 300'. The bead 300' may be fused to the end of the wire 200 or adhered thereto. Indeed, the bead 300' represents numerous other enlargements that could be used on the end of the wire 200 to prevent it pulling free of the molded tip 210. For instance, the end of the wire 200 could be compressed into a bead or a flat head, much like a rivet, or the bead 300' could be a different shape such as square to provide some torsional resistance.

The materials of the balloon 112 and tip 210 are desirably similar to facilitate their bonding from the application of heat to their interface. For example, the balloon 112 and tip 210 may be formed from Nylon or a high durometer thermoplastic elastomer (TPE) such as PEBAX®. The distal tubular end 290 of the balloon 112 fits closely around the shaft region 302 and abuts a small shoulder 310 at the beginning of the hemi-spherical bulb 304. This construction of the heat fusion coupled with the physical engagement between the end of the balloon and the shoulder 310 provides a redundant attachment system with high axial pull strength. That is, the attachment system prevents disengagement of the tip 210 from the balloon 112, and also effectively resists separation leading to leaking. Furthermore, the J-shaped bend 300 presents an anchor of sorts within the material of the molded tip 210. Pull tests have demonstrated that the assembly can withstand 40 lb of pull force without the wire 200 breaking free of the tip 210.

Figure 46A:
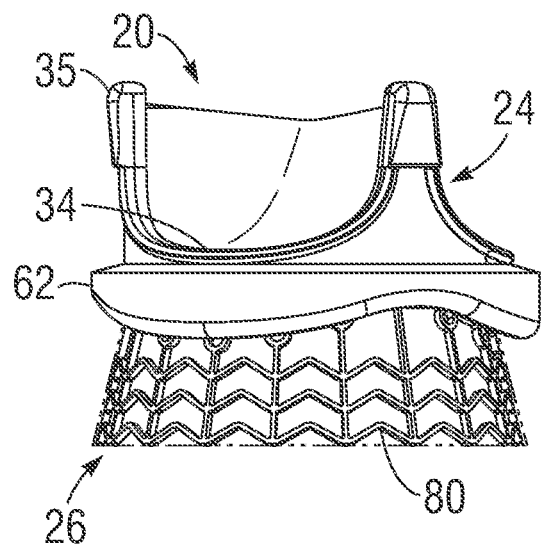
FIGS. 46A and 46B are views of exemplary prosthetic heart valve disclosed herein, shown respectively assembled and with an expandable skirt exploded from a valve component.
Figure 46B:
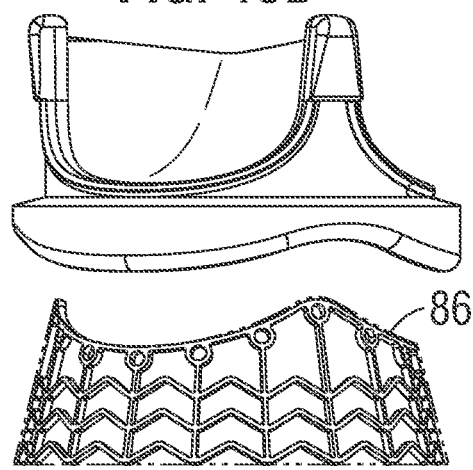

One important aspect of the present heart valve delivery system is the configuration of the expandable anchoring skirt 26 in terms of its construction within the heart valve and also its shape upon expansion. FIGS. 46A and 46B illustrate the exemplary prosthetic heart valve 20 both assembled and with the anchoring skirt 26 exploded from the valve component 24. Again, the valve member 24 may be an "off-the-shelf" commercial prosthetic valve such as the Carpentier-Edwards PERIMOUNT Magna® Aortic Heart Valve available from Edwards Lifesciences. The anchoring skirt 26 primarily includes the inner plastically-expandable frame or stent 80, with a fabric cover not shown for clarity.

As mentioned, the anchoring skirt 26 attaches to an inflow end of the valve member 24, typically via sutures through the upper end 86 of the stent frame 80 connected to fabric on the valve member 24, or to the sewing ring 62. The particular sewing ring 62 shown includes an undulating inflow contour that dips down, or in the inflow direction, in the regions of the valve cusps 34, and arcs up, in the outflow direction, in the regions of the valve commissures 35. This undulating shape generally follows the inflow end of the heart valve member wireform 50 (see FIG. 10) which seats down within the sewing ring 62. The scalloped upper end 86 of the stent frame 80 also conforms to this undulating shape, with peaks aligned with the valve commissures 35 and valleys aligned with the valve cusps 34. Further details on exemplary valve/stent constructions are provided below with reference to FIGS. 55-58.

Figure 47A:
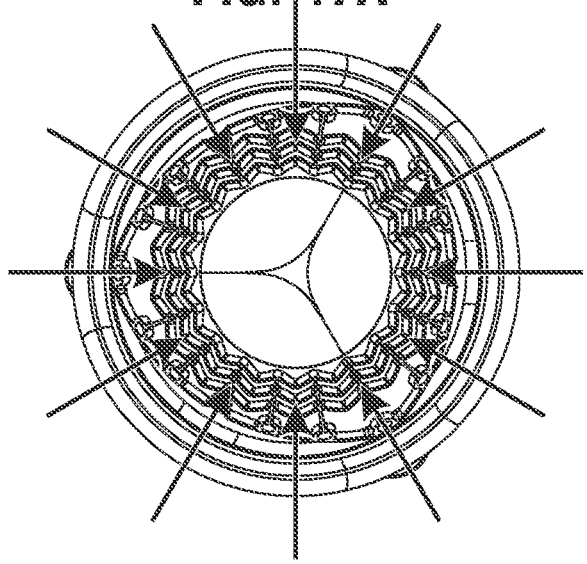
FIGS. 47A, 47B, 48A, and 48B are views of the exemplary prosthetic heart valve schematically showing methods for crimping the expandable skirt into a conical delivery configuration.
Figure 47B:
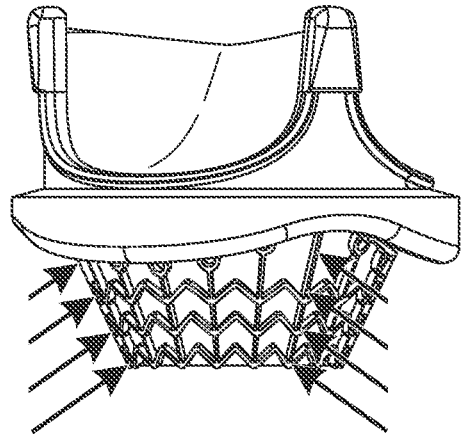
Figure 48A:
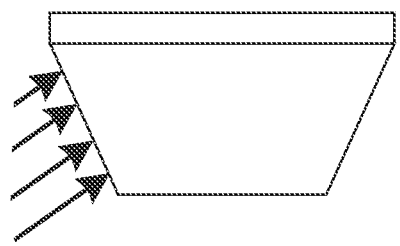

With reference back to FIGS. 46-48, the stent frame 80 of the anchoring skirt 26 may be initially formed in several ways. For instance, a tubular portion of suitable metal such as stainless steel may be laser cut to length and to form the latticework of chevron-shaped interconnected struts. Other methods including wire bending and the like are also possible. The resulting stent frame 80 is initially tubular when attached to the valve member 24, and is then crimped into the conical shape shown in FIGS. 47A and 47B in a first crimping step. Preferably, a distributed inward crimping force is applied at even locations around the stent frame 80, such as indicated by the arrows in the figures. The frame 80 is fixed along and thus pivots inward about its scalloped upper end 86. The crimping forces are applied starting at about the level of the valleys of the uneven upper end 86, as schematically indicated in FIG. 48A, leaving a short axial distance where the stent frame 80 remains cylindrical.

Figure 48B:
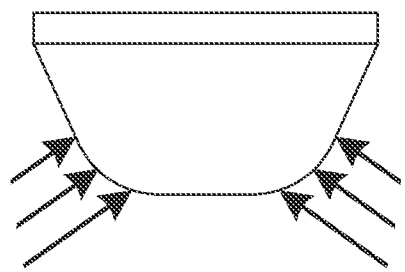

In a preferred second crimping step, shown in FIG. 48B, inward forces are applied unevenly to curl the lower or distal end of the stent frame 80 inward, resulting in a somewhat spherical distal end. To avoid causing overlap between the struts of the plastically-expandable stent frame 80, the forces are desirably applied more at three locations distributed 120° apart so that a bottom plan view (see FIG. 7D) shows the lower end having a trilobular shape rather than circular. This helps reduce the leading end profile of the valve without compromising the ability of the stent frame 80 to freely expand into the shape in FIG. 46A. Regardless of the crimping method, the inflation balloon 112 ultimately outwardly expands the inflow end of the stent frame 80 to form the conical shape of FIGS. 46A and 46B.

It should be mentioned that as an alternative to a balloon, a mechanical expander may be used to expand the anchoring skirt 26 shown above. For instance, a mechanical expander may include a plurality of spreadable fingers actuated by a syringe-like apparatus, as seen in co-pending U.S. Patent Publication No. 2010-0161036, filed Dec. 10, 2009, incorporated above. The fingers are axially fixed but capable of pivoting or flexing with respect to a barrel. The distal end of a plunger has an outer diameter that is greater than the diameter circumscribed by the inner surfaces of the spreadable fingers, such that distal movement of the plunger with respect to the barrel gradually cams the fingers outward within the coupling stent. Therefore, the term "plastically-expandable" encompasses materials that can be substantially deformed by an applied force to assume a different shape. Some self-expanding stents may be deformed to a degree by an applied force beyond their maximum expanded dimension, but the primary cause of the shape change is elastic rebound as opposed to a plastic deformation.

In accordance with one alternative embodiment, FIGS. 49-50 show an expansion system including mechanical fingers 320 in conjunction with an inflatable balloon 322 for expanding the anchoring skirt 26. FIG. 50A illustrates the mechanical fingers 320 surrounding the balloon 322 and extending from a handle attachment member 324 that is partly inserted into the inflow end of a prosthetic heart valve 20 as described herein. The assembly of the attachment member 324, mechanical fingers 320 and balloon 322 is shown in cross-section in FIG. 49. The handle attachment member 324 includes a lumen 326 therethrough having internal threading 328 on a proximal end. A malleable handle such as that described above may be threaded onto the proximal end of the attachment member 324 and supply inflation fluid for the balloon 322.

The mechanical fingers 320 may be hinged about a distal end of the attachment member 324, such with living hinges 330 as seen in FIG. 49 and in the detail of FIG. 50E. In a preferred embodiment, the living hinges 330 are each formed by a V-shaped notch having an included angle—that limits outward movement of the fingers 320. The fingers 320 may be slightly tapered so as to be radially thicker on the distal ends. As the assembly inserts within the heart valve 20, such as from the position in FIG. 50A to the position in FIG. 50B, the inflow aspect of the valve having the anchoring skirt 26 eventually contacts the exterior surfaces of the fingers 320. Further relative movement increases the frictional fit between the interior of the skirt 26 and the exterior of the fingers 320 (biasing the fingers inward against the resiliency of the balloon 322) until a series of outwardly-directed detents 340 engage the struts of the stent frame 80, as seen in FIG. 50E. The detents 340 comprise small angled cutouts that define hooks on the distal ends of the fingers 320, the cutouts being oriented at angle—with the radial that optimally captures the struts of the anchoring skirt 26. This locks the position of the mechanical fingers 320 relative to the anchoring skirt 26. Inflation of the balloon 322, as seen in FIG. 50E, pivots the mechanical fingers 320 outward about the living hinges 330, forcing the distal end of the anchoring stent 26 outward into contact with the surrounding anatomy. The V-shaped notches forming the living hinges 330 limit outward rotation of each of the fingers 320 to a predetermined magnitude so as to avoid over expanding the anchoring stent 26.

In use, the expansion assembly of the mechanical fingers 320, balloon 322, and attachment member 324 are inserted through the inflow aspect of the prosthetic heart valve 20 until locked into position with the detents 340 engage with the distal end of the skirt 26. Subsequently, a hollow-shaft of malleable handle may be attached to the proximal end of the attachment member 324. Alternatively, the prosthetic heart valve 20 can be sutured and parachuted in situ with the expander assembly inserted but without a handle attached. Upon satisfactory placement of the valve 20 in situ, a conventional inflation device along with the handle may be connected to the attachment member 324 for inflating the balloon 322. Deflation of the balloon 322 after installation of the heart valve 20 causes the mechanical fingers 320 to pivot inward again. The fingers 320 may be bonded to the exterior of the balloon 322 to facilitate inward retraction thereof when the vacuum is applied to the balloon.

Alternatives to the expansion assembly of FIGS. 49-50 include mechanical fingers that are not pivotally attached to a handle attachment member. In this way, an inflation balloon causes direct radial expansion of the fingers instead of a pivoting movement. Furthermore, an elongated malleable handle may be provided as one piece with the attachment member 324, rather than as a threaded coupling.

As mentioned previously, the present application contemplates various alternatives for ensuring that the valve inflation balloon does not prematurely inflate. For example, FIGS. 51-54 schematically illustrate systems where a port for fluid used to inflate the balloon on the catheter must be first opened prior to balloon expansion.

Figure 35:
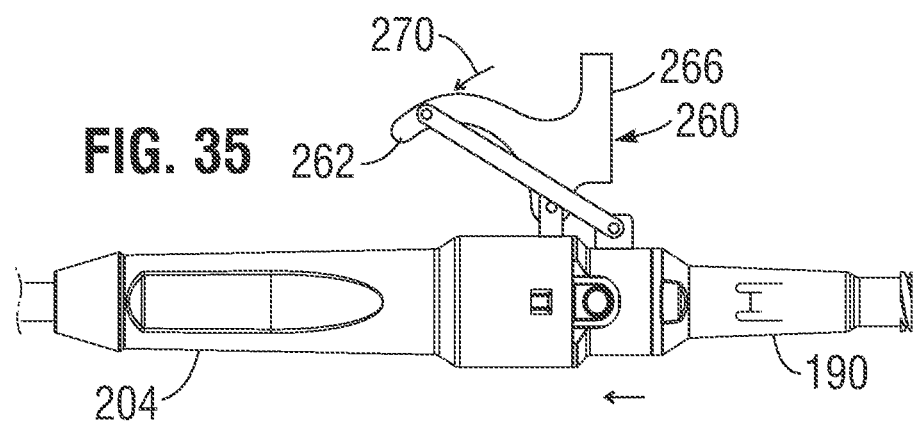
Figure 51:
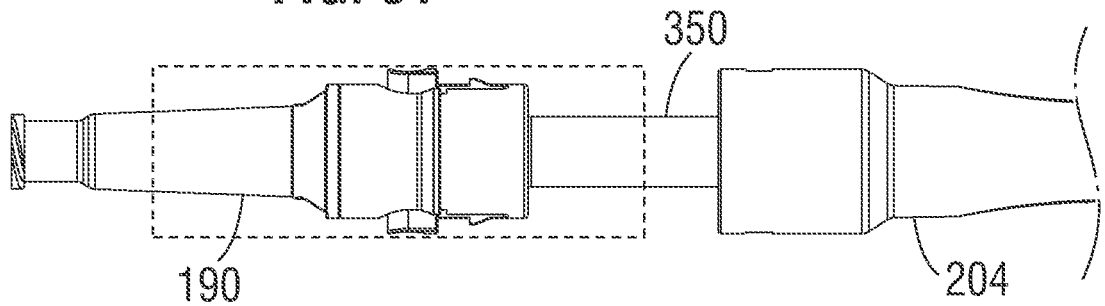
FIGS. 51, 52A-52C, 53, and 54A-54C schematically illustrate alternative valve systems for fluid used to inflate the balloon on the catheter disclosed herein that prevent premature deployment of the balloon.

FIG. 51 is an elevational view of a portion of the proximal end of an alternative delivery system 110 similar to the views of FIGS. 34-36, and showing the relatively movable end cap 190 and handpiece 204. A tubular extension 350 of the end cap 190 shown schematically in FIG. 52A includes a closed distal end 352 and a pair of side ports 354 just proximal to the distal end. The tubular extension 350 fits closely within a bore 356 formed in a proximal end of the handpiece 204. Prior to balloon expansion, the components are positioned as seen in FIG. 52B, with the distal end of the tubular extension 350 positioned within the bore 350 such that the side ports 354 are blocked. Distal movement of the end cap 190 as seen in FIG. 52C causes the tubular extension 350 to project from within the bore 356 into a larger chamber 358, thus exposing the side ports 354 so the fluid may be injected toward the distal balloon. In this configuration, the end cap 190 must first move distally relative to the handpiece 204 before fluid can be injected to inflate the balloon.

Figure 54B:
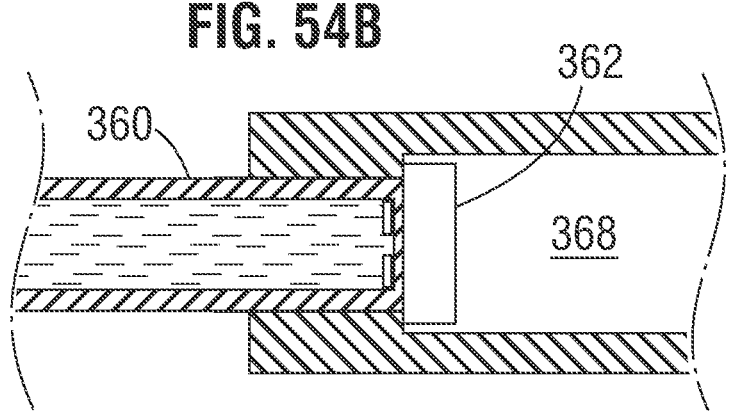
Figure 54C:
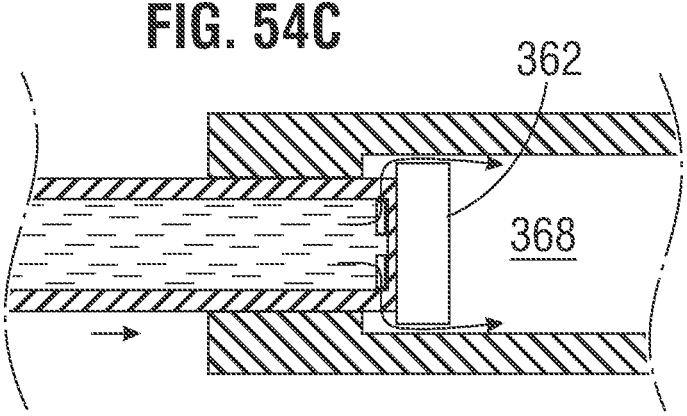

FIG. 53 also shows a portion of the proximal end of an alternative delivery system 110 similar to the views of FIGS. 34-36, with the relatively movable end cap 190 and handpiece 204. A tubular extension 360 of the end cap 190 shown exploded in FIG. 54A again includes a distal end closed by a plunger 362 and has a pair of side ports 364 just proximal to the distal end. The tubular extension 350 fits closely within a bore 366 formed in a proximal end of the handpiece 204. Prior to balloon expansion, the components are positioned as seen in FIG. 54B, with the plunger 362 sealed against the opening to the bore 366 such that the side ports 364 are blocked. Distal movement of the end cap 190 as seen in FIG. 54C causes movement of the plunger 362 into a larger chamber 368, thus opening the side ports 364 so the fluid may be injected toward the distal balloon. Again, this configuration ensures that the end cap 190 must first move distally relative to the handpiece 204 before fluid can be injected to inflate the balloon.

Various heart valves may be utilized in combination with the delivery system components described herein, and any combination not otherwise explicitly described is contemplated. For instance, FIG. 55 is a perspective view of an exemplary prosthetic heart valve 400 having a commercially available valve member 402 coupled with an anchoring stent 404 minus a surrounding fabric cover. FIG. 55A is a radial sectional view through a cusp portion of the heart valve 400 with a fabric cover 406 of the skirt stent 404 shown. Finally, FIG. 56 is an exploded elevational view of the prosthetic heart valve 400 of FIG. 55. The particular valve member 402 shown is the Carpentier-Edwards PERIMOUNT Magna® Aortic Heart Valve available from Edwards Lifesciences of Irvine, Calif. As seen in FIG. 55A, the Magna valve has a structure including a wireform 410 wrapped in a cloth cover 412 and attached to a cloth-covered axial band structure 414 with flexible bioprosthetic leaflets 414 sandwiched therebetween. A highly flexible sewing ring 416 attaches to the outside perimeter of the band structure 414 as shown. Finally, the cloth-covered anchoring skirt 404 is secured at a butt joint to an inflow end of the Magna valve, such as with sutures through the respective cloth covers and desirably through the stent frame of the skirt 404 and through apertures in the band structure 414, as described above. The sewing ring 416 attaches to the band structure 414 along a line of stitching, rendering it easily flexed outward. Further, the sewing ring 416 has a relatively thin-walled silicone insert 418 with a honeycomb structure. That is an advantage for conventional valves, but may not be quite so desirable for valves as described herein.

Figure 57:
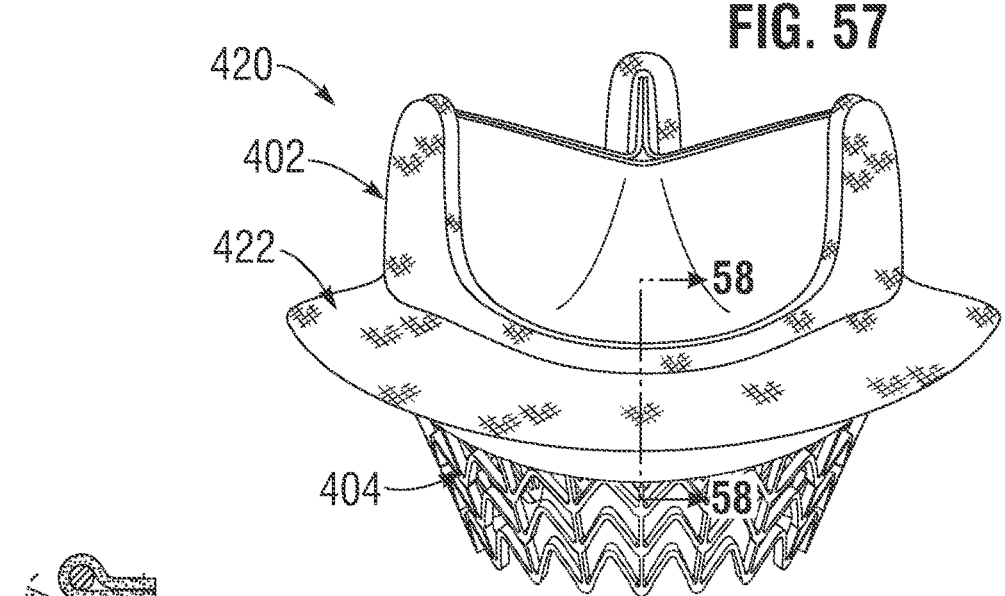
FIG. 57 is a perspective view of an alternative prosthetic heart valve similar to that shown in FIG. 55 but having a different firmer sewing ring.
Figure 58A:
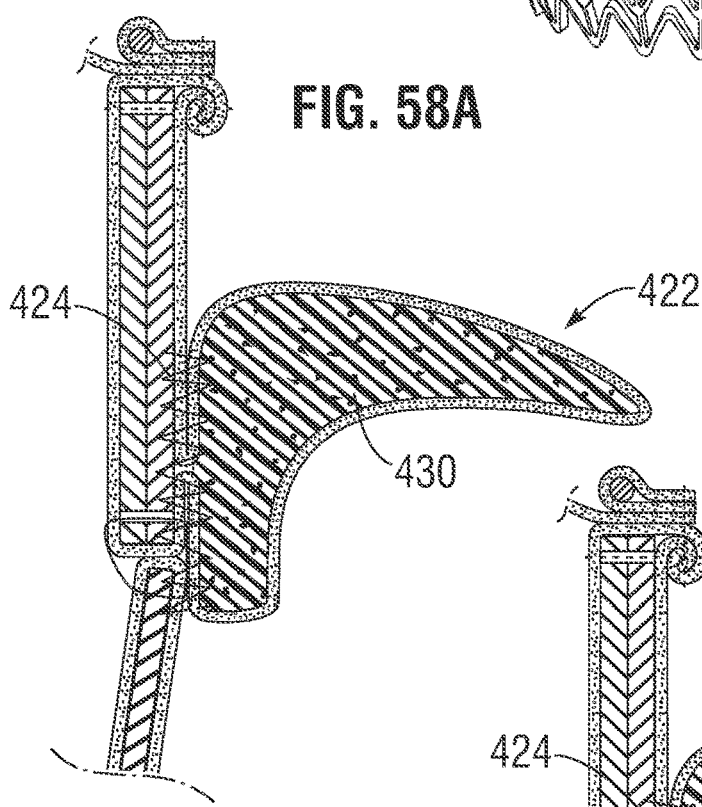
FIGS. 58A and 58B are radial sectional views through the prosthetic heart valve of FIG. 57 illustrating alternative constructions.
Figure 58B:
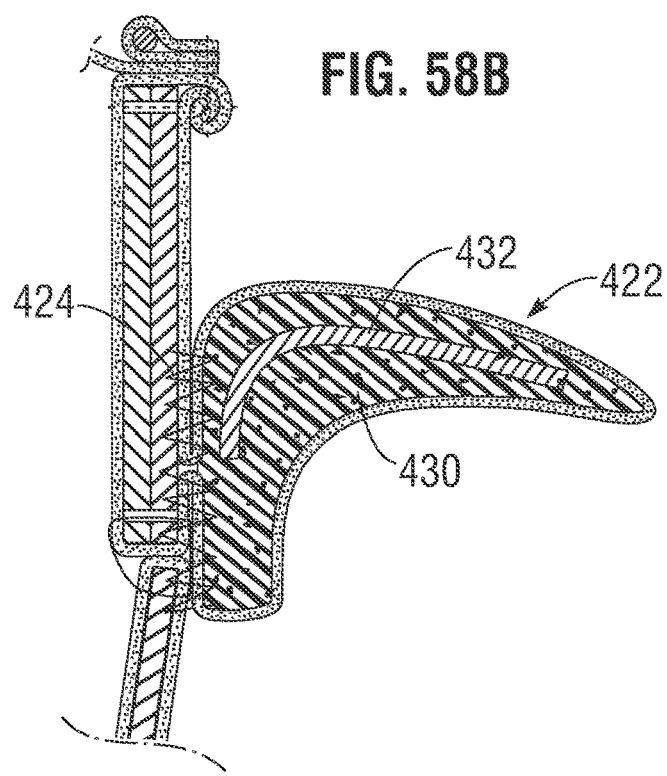

In contrast, FIG. 57 shows an alternative prosthetic heart valve 420 similar to that shown in FIG. 55 but having a different, firmer sewing ring 422. In particular, FIGS. 58A and 58B are radial sectional views through the prosthetic heart valve 420 illustrating alternative constructions of the sewing ring 422. Like elements will be given like numbers.

In both FIGS. 58A and 58B the sewing ring 422 secures to the outside of the band structure 414 along a cylindrical region of stitching 424, which helps reduce up and down flexing of the sewing ring 422. Secondly, the sewing ring 422 in FIG. 58A comprises a solid yet compressible material that is relatively stiff so as to provide a seal against the annulus and has a concave inflow shape that conforms to the annulus. Desirably, the sewing ring 422 includes a closed-cell foam insert 430 within a cloth cover. There are no cavities/cells, which makes the sewing ring 422 soft to the surrounding tissue yet relatively stiff overall. Moreover, the concave inflow side matches that of the annulus for better sealing therebetween. FIG. 58B shows an additional reinforcing member 432 embedded within the insert 430 that stiffens the sewing ring 422 even further. The reinforcing member 432 may be metallic, such as stainless steel or the like. Both sewing rings 422 are stiffer than the Magna sewing ring and thus create a better seal against the aortic valve annulus in opposition to the outwardly expanded anchoring skirt within the left ventricle. The combination provides a relatively secure anchoring structure for the valves disclosed herein, and helps prevent paravalvular leaking around the outside of the valve by matching the shape of and firmly holding the soft material against the annulus.

Once again, the cloth-covered anchoring skirt 404 is secured at a butt joint to an inflow end of the Magna valve, such as with sutures through the stent frame of the skirt 404 and through apertures in the band structure 414. Furthermore, the lower end of the sewing ring 422 desirably overlaps the anchoring skirt 404 by a short distance and the stitching 424 extends down therebetween. This further enhances the stiffness of the assembly, thus improving seating and sealing against the aortic annulus. Although not shown, the sewing ring 422 may be annular but is desirably slightly scalloped so as to better conform to the aortic annulus. The stiff scalloped sewing ring 422 assists the surgeon in rapidly seating the prosthetic valve in place by providing a firm platform to mate against the contours of the undulating aortic annulus.

It should be noted that a sewing ring per se may not be necessary with the present heart valve as the primary function of such a component is to provide a platform through which to pass a number of anchoring sutures around the valve periphery, which is not used here except perhaps for several (e.g., 3) guide sutures. Consequently, the valve members described herein could be coupled to the anchoring skirt directly without a sewing ring. To help prevent paravalvular leaking a peripheral seal such as a fabric skirt may be added in place of the sewing ring. Also, several tabs extending outward from the vale structure could be used for anchoring the guide sutures which take the place of the sewing ring for that purpose.

The system disclosed herein is also desirably used with a particular valve annulus sizing technique. The sizing apparatus (not shown) includes a catheter shaft having a compliant balloon on a distal end that can be inflated with saline. An intravascular ultrasound (IVUS) imaging probe extends through the catheter and within the compliant balloon. After preparing the patient for surgery, but prior to introduction of the delivery system 110, the balloon catheter is introduced into the valve annulus. The balloon is filled to a desired pressure, and the IVUS probe is advanced through the catheter and into the balloon. Because the balloon conforms to the anatomical cavity surrounding it, the IVUS probe measures the size of that cavity.

The advantage of being able to expand the native annulus with the expandable skirt to receive a larger valve size than would otherwise be possible with conventional surgery was mentioned above. Another way to accomplish such enlargement is to utilize a tapered dilator, such as a Hagar dilator. The conical dilator has a maximum diameter that is larger than the anticipated valve diameter. By passing the dilator into the annulus prior to installation of the valve, a larger valve may be selected. Furthermore, the larger valve temporarily fits within the annulus, but the resiliency of the tissue constricts around the valve for a more secure anchor.

While the invention has been described in its preferred embodiments, it is to be understood that the words which have been used are words of description and not of limitation. Therefore, changes may be made within the appended claims without departing from the true scope of the invention.

What is claimed is:

1. A system for delivering a prosthetic heart valve, comprising:
   a heart valve including a prosthetic valve with an expandable frame having a contracted state for delivery to an implant position and an expanded state;
   a valve holder attached to the heart valve and having a through passage;
   a balloon catheter having a balloon, the balloon catheter and a proximal end of the balloon being fixable with respect to the valve holder with the balloon passing through the through passage of the valve holder to a position within the expandable frame, the balloon catheter having a proximal end defining a lumen in which is housed a balloon extension spring and a spring compression pin, wherein the spring compression pin is fixed to a balloon extension wire that extends distally through the balloon catheter and is attached to a distal tip of the balloon, wherein the balloon is configured to axially foreshorten when inflated such that the distal tip is displaced proximally with respect to the proximal end and the balloon extension wire and spring compression pin are also displaced proximally to compress the balloon extension spring, and wherein the balloon extension spring is configured to subsequently expand to axially lengthen the balloon when being deflated.

2. The system of claim 1, wherein the balloon extension spring is configured to undergo complete compression to a solid length when the balloon inflates so as to provide a positive stop on proximal movement of the balloon extension wire, spring compression pin and attached balloon distal tip.

3. The system of claim 1, wherein the proximal end of the balloon catheter has a luer fitting for connection of a source of inflation fluid, and wherein the balloon extension wire extends proximally out of the luer fitting for manual manipulation.

4. The system of claim 1, wherein the spring compression pin is constrained within the lumen of the balloon catheter proximal end to translate within a helical track.

5. The system of claim 1, wherein the prosthetic valve has an inner frame assembly defining a non-expandable, non-collapsible orifice, and the expandable frame extends in series from an inflow end thereof.

6. The system of claim 1, further including a handle shaft having a shaft lumen for sliding passage of the balloon catheter and a distal end configured to mate with a proximal end of the valve holder such that the balloon can be advanced distally through the handle shaft, through the valve holder and within the heart valve, and wherein the distal end of the handle shaft and a proximal end of the valve holder have keyed structures that are unique for different sizes of valves such that a handle shaft for one valve size cannot mate with a valve holder of a different valve size.

7. The system of claim 6, wherein the heart valve includes a plurality of flexible leaflets that provide fluid occluding surfaces across the orifice, the system further including a balloon introducer sleeve coupled to the valve holder that extends through the flexible leaflets and prevents contact between the balloon catheter and the flexible leaflets when the balloon catheter advances within the heart valve.

8. The system of claim 6, wherein the handle shaft is malleable and can be bent and retain its bent shape.

9. The system of claim 8, wherein the malleable handle shaft is made of aluminum.

10. The system of claim 8, wherein the balloon catheter has an inflation tube that extends through the shaft lumen of the handle shaft and an OD of the inflation tube is sized more than 90% the ID of the shaft lumen.

11. A system for delivering a prosthetic heart valve, comprising:
    a heart valve including a prosthetic valve with an expandable frame having a contracted state for delivery to an implant position and an expanded state;
    a valve holder attached to the heart valve and having a through passage;
    a balloon catheter having a balloon, the balloon catheter and a proximal end of the balloon being fixable with respect to the valve holder with the balloon passing through the through passage of the valve holder to a position within the expandable frame, the balloon catheter having a balloon extension wire that extends distally through the balloon catheter and is attached to a molded balloon wire tip on a distal end of the balloon, wherein the balloon is configured to axially foreshorten when inflated such that the distal end is displaced proximally with respect to the proximal end and the balloon extension wire is also displaced proximally to compress a balloon extension spring in the balloon catheter, thus placing the balloon extension wire in compression, and wherein a distal tip of the balloon extension wire has an enlargement embedded within the balloon wire tip that is heat bonded to the distal end of the balloon.

12. The system of claim 11, wherein the balloon extension spring is positioned at a proximal end of the balloon catheter such that the balloon extension wire extends along the length of the balloon catheter, and wherein the balloon extension wire is formed of nitinol.

13. The system of claim 12, further including a hypotube closely surrounding the balloon extension wire so as to stiffen the balloon extension wire, the hypotube extending within the balloon and terminating at or a short distance proximally beyond the proximal end of the balloon to avoid adding stiffness along a majority of the balloon extension wire and balloon catheter.

14. The system of claim 11, wherein the balloon wire tip and balloon are formed of the same material selected from the group consisting of nylon and a high durometer thermoplastic elastomer.

15. The system of claim 14, wherein the balloon wire tip has a proximal cylindrical shaft region around which the distal end of the balloon fits closely, and the proximal cylindrical shaft region terminates at an outwardly stepped shoulder against which the distal end of the balloon abuts.

16. The system of claim 11, wherein the balloon wire tip terminates at a distal hemi-spherical end.

17. The system of claim 11, wherein the balloon wire tip enlargement is formed by a J-shaped bent end.

18. The system of claim 11, wherein the prosthetic valve has an inner frame assembly defining a non-expandable, non-collapsible orifice, and the expandable frame extends in series from an inflow end thereof.

19. The system of claim 11, further including a handle shaft having a shaft lumen for sliding passage of the balloon catheter and a distal end configured to mate with a proximal end of the valve holder such that the balloon can be advanced distally through the handle shaft, and wherein the balloon has a visible midline that, in an advanced position of the balloon, is located within 1-2 mm of the distalmost end of the expandable frame of the heart valve.

20. The system of claim 19, wherein the heart valve includes a plurality of flexible leaflets that provide fluid occluding surfaces across the orifice, the system further including a balloon introducer sleeve coupled to the valve holder that extends through the flexible leaflets and prevents contact between the balloon catheter and the flexible leaflets when the balloon catheter advances within the heart valve.

* * * * *